United States Patent [19]

King et al.

[11] Patent Number: 5,101,074
[45] Date of Patent: Mar. 31, 1992

[54] VICINAL DI(HETRO) ALKYLENE ORGANOMETALATES AND PROCESSES FOR THE PRODUCTION OF AMINES THEREWITH

[75] Inventors: Stephen W. King, Scott Depot; Arthur R. Doumaux, Jr., Charleston; David J. Schreck, Cross Lanes, all of W. Va.; George A. Skoler, White Plains, N.Y.

[73] Assignee: Union Carbide Chemicals & Plastics Technology Corporation, Danbury, Conn.

[21] Appl. No.: 390,828

[22] Filed: Aug. 8, 1989

[51] Int. Cl.$^5$ .................. C07C 209/01; C07C 211/02
[52] U.S. Cl. ..................................... 564/479; 564/512
[58] Field of Search ........................... 564/512, 479

[56] References Cited

U.S. PATENT DOCUMENTS

| | | | |
|---|---|---|---|
| 2,073,671 | 4/1931 | Andrews | 260/127 |
| 2,467,205 | 4/1949 | Gresham et al. | 260/268 |
| 3,734,963 | 5/1973 | Langer, Jr. et al. | 564/512 |
| 4,036,881 | 7/1977 | Brennan et al. | 260/583 P |
| 4,044,053 | 8/1977 | Brennan et al. | 260/583 P |
| 4,301,036 | 11/1981 | Childress et al. | 252/458 |
| 4,314,083 | 2/1982 | Ford et al. | 564/479 |
| 4,316,840 | 2/1982 | Ford et al. | 260/239 BC |
| 4,316,841 | 2/1982 | Ford et al. | 260/239 BC |
| 4,324,917 | 4/1982 | McConnell | 564/479 |
| 4,362,886 | 12/1982 | Ford et al. | 564/479 |
| 4,394,524 | 7/1983 | Ford et al. | 564/479 |
| 4,399,308 | 8/1983 | Ford et al. | 564/479 |
| 4,448,997 | 5/1984 | Brennan | 564/479 |
| 4,463,193 | 7/1984 | Johnson et al. | 564/479 |
| 4,503,253 | 3/1985 | Ford et al. | 564/479 |
| 4,521,600 | 6/1985 | Wells et al. | 544/352 |
| 4,524,143 | 6/1985 | Vanderpool | 502/208 |
| 4,540,822 | 9/1985 | Vanderpool | 564/479 |
| 4,547,591 | 10/1985 | Brennan et al. | 564/479 |
| 4,550,209 | 10/1985 | Unvert et al. | 564/479 |
| 4,552,961 | 11/1985 | Herdle | 544/402 |
| 4,555,582 | 11/1985 | Vanderpool | 564/479 |
| 4,560,798 | 12/1985 | Ford et al. | 564/503 |
| 4,578,517 | 3/1986 | Johnson et al. | 564/479 |
| 4,578,518 | 3/1986 | Vanderpool et al. | 564/479 |
| 4,578,519 | 3/1986 | Larken et al. | 564/479 |
| 4,584,405 | 4/1986 | Vanderpool | 564/479 |
| 4,584,406 | 4/1986 | Vanderpool et al. | 564/479 |
| 4,588,842 | 5/1986 | Vanderpool | 564/479 |
| 4,605,770 | 8/1986 | Ford et al. | 564/479 |
| 4,609,761 | 9/1986 | Watts, Jr. et al. | 564/479 |
| 4,612,397 | 9/1986 | Renken | 564/479 |
| 4,617,418 | 10/1986 | Ford et al. | 564/479 |
| 4,667,045 | 5/1987 | Briggs et al. | 556/20 |
| 4,683,335 | 7/1987 | Knifton et al. | 564/480 |
| 4,698,427 | 10/1987 | Vanderpool | 544/404 |
| 4,720,588 | 1/1988 | Turcotte et al. | 564/479 |
| 4,774,218 | 9/1988 | Shimasaki et al. | 502/202 |
| 4,806,517 | 2/1989 | Vanderpool et al. | 502/208 |
| 4,822,925 | 4/1989 | Briggs et al. | 568/716 |
| 4,833,248 | 5/1989 | Shimasaki et al. | 546/184 |
| 4,841,061 | 6/1989 | Shimasaki et al. | 546/184 |
| 4,922,024 | 5/1990 | Bowman et al. | 564/480 |

FOREIGN PATENT DOCUMENTS

| | | |
|---|---|---|
| 0290960 | 11/1988 | European Pat. Off. |
| 375355 | 6/1990 | European Pat. Off. |
| 78945 | 5/1985 | Japan |
| 236752 | 10/1986 | Japan |
| 236753 | 10/1986 | Japan |
| 63-23744 | 1/1988 | Japan |
| 303964 | 12/1988 | Japan |
| 211246 | 8/1990 | Japan |
| 9003963 | 4/1990 | World Int. Prop. O. |

OTHER PUBLICATIONS

Bradley, D. C. et al., Metal Alkoxides, Academic Press, New York, 1978, pp. 226-281.

Primary Examiner—C. Warren Ivy
Assistant Examiner—Raymond Covington
Attorney, Agent, or Firm—Rose M. Allen

[57] ABSTRACT

This invention relates to vicinal di(hetero)alkylene organometalate compounds comprising one or more metal oxides in association with an alkanolamine, an alkyleneamine, an alkylene glycol or mixtures thereof. This invention also relates to an alkyleneamines producers composition rich in triethylenetetramine (TETA), tetraethylenepentamine (TEPA) and pentaethylenehexamine (PEHA), and to processes for the preparation thereof using the vicinal di(hetero)alkylene organometalates.

65 Claims, No Drawings

VICINAL DI(HETRO) ALKYLENE ORGANOMETALATES AND PROCESSES FOR THE PRODUCTION OF AMINES THEREWITH

RELATED APPLICATIONS

U.S. patent application Ser. No. 136,615, filed Dec. 22, 1987, commonly assigned.

The following are related, commonly assigned applications, filed on an even date herewith: U.S. patent application Ser. No. 390,829; U.S. patent application Ser. No. 390,709; U S. patent application Ser. No. 390,714; U.S. patent application Ser. No. 390,708; and U.S. patent application Ser. No. 390,706; all incorporated herein by reference.

BRIEF SUMMARY OF THE INVENTION

Technical Field

This invention relates to vicinal di(hetero)alkylene organometalate compounds comprising one or more metal oxides in association with an alkanolamine, an alkyleneamine, an alkylene glycol or mixtures thereof.

This invention also relates to an alkyleneamines producers composition rich in higher polyalkylene polyamines such as triethylenetetramine (TETA), tetraethylenepentamine (TEPA) and pentaethylenehexamine (PEHA), and to processes for the preparation thereof using the vicinal di(hetero)alkylene organometalates.

Background of the Invention

There is a substantial body of literature directed to the use of various acid catalysts to effect intramolecular and intermolecular condensation of amino compounds. U.S. Pat. No. 2,073,671 and U.S. Pat. No. 2,467,205 constitute early prior work on the use of acid condensation catalysts to condense amino compounds. U.S. Pat. No. 2,073,671 discusses, in a general fashion, the catalytic intermolecular condensation of alcohols and amines or ammonia using the same phosphate catalysts later favored by U.S. Pat. No. 2,467,205 for the intramolecular condensation of amines. The two patents are not in harmony over the use of other materials as catalysts. To illustrate this point, U.S. Pat. No. 2,073,671 states:

"Alumina, thoria, blue oxide of tungsten, titania, chromic oxide, blue oxide of molybdenum and zirconia have been mentioned in the literature for use as catalysts in carrying out these reactions but their effectiveness is so low that no practical application has been made of their use."

whereas U.S. Pat. No. 2,467,205 in describing the self-condensation of ethylenediamine (EDA) under vapor phase conditions, to initially produce ethyleneamines, but after recycle, eventually generates piperazine through multistep condensation reactions, followed by deamination, recommends "dehydration catalysts" which are thereafter characterized as "silica gel, titania gel, alumina, thoria boron phosphate, aluminum phosphate, and the like."

U.S. Pat. No 2,073,671 describes the condensation catalyst in the following terms:

". . . a heated catalyst or contact mass containing phosphorus and especially one or more of the oxygen acids of phosphorus, their anhydrides, their polymers, and their salts; for example, orthophosphoric acid, metaphosphoric acid, pyrophosphoric acid, phosphorous pentoxide, dimetaphosphoric acid, trimetaphosphoric acid, primary ammonium phosphate, secondary ammonium phosphate, normal ammonium phosphate, ammonium metaphosphate, secondary ammonium pyrophosphate, normal ammonium pyrophosphate, aluminum phosphate, aluminum acid phosphate and mixtures of two or more of such materials."

whereas U.S. Pat. No. 2,467,205 describes one of the preferred catalysts as "basic aluminum phosphate".

U.S. Pat. No. 2,454,404 describes the "catalytic deamination of alkylene polyamines" by reacting diethylenetriamine (DETA) vapor over solid catalysts such as activated alumina, bauxite, certain aluminum silicates such as kaolin and oxides of thorium, titanium and zirconium.

U.S. Pat. Nos. 2,073,671 and 2,467,205 demonstrate a common experience in using aluminum phosphate as a condensation catalyst to produce aliphatic amines, and U.S. Pat. Nos. 2,454,404 and 2,467,205 contemplate the other solid catalysts for deamination of amines to make heterocyclic noncyclic amines. In general, the reaction conditions under which deamination to effect cyclization occurs are more severe than those employed for condensation to generate noncyclic molecules, all other factors being comparable.

U.S. Pat. Nos. 4,540,822, 4,584,406 and 4,588,842 depict the use of Group IVB metal oxides as supports for phosphorus catalysts used to effect the condensation of amino compounds with alkanolamines.

U.S. Pat. No. 4,683,335 describes the use of tungstophosphoric acid, molybdophosphoric acid or mixtures deposited on titania as catalysts for the condensation of amines and alkanolamines to make polyalkylenepolyamines.

U.S. Pat. Nos. 4,314,083, 4,316,840, 4,362,886 and 4,394,524 disclose the use of certain metal sulfates as useful catalysts for the condensation of alkanolamine and an amino compound. No distinction is made between the sulfur compounds in respect to catalytic efficacy. Sulfuric acid is as good as any metal sulfate, and all metal sulfates are treated as equivalents. At column 8 of U.S. Pat. No. 4,314,083, it is noted that boron sulfate "gave extremely high selectivity at a low level" of EDA. However, selectivity in general was shown to increase with an increase of EDA relative to MEA in the feed. The only specific metal sulfates disclosed in the patents are antimony sulfate, beryllium sulfate, iron sulfate and aluminum sulfate.

In the typical case of the manufacture of alkyleneamines, mixtures with other alkyleneamines (including a variety of polyalkylenepolyamines and cyclic alkylenepolyamines) are formed. The same holds true when the object of the process is to produce polyalkylenepolyamines whether acyclic or cyclic, in that a variety of amino compounds are also formed. Each of these cyclic and acyclic alkyleneamines can be isolated from the mixture.

The acid catalyzed condensation reaction involving the reaction of an alkanolamine with an amino compound in the presence of an acidic catalyst is believed to proceed through the mechanism of esterifying free surface hydroxyl groups on the acid catalyst with the alkanolamine and/or by protonating the alkanolamine in the presence of the acid catalyst, followed by loss of water and amine condensation of the ester or the hydrated species, as the case may be, to form the alkyleneamine. Illustrative prior art directed primarily to the cyclic polyalkylenepolyamines (heterocyclic polyamines), but not necessarily limited to the aforementioned acid condensation reaction, are: U.S. Pat. Nos. 2,937,176, 2,977,363, 2,977,364, 2,985,658, 3,056,788, 3,231,573, 3,167,555, 3,242,183, 3,297,701, 3,172,891, 3,369,019, 3,342,820, 3,956,329, 4,017,494, 4,092,316, 4,182,864, 4,405,784 and 4,514,567; European Patent Applications 0 069 322, 0 111 928 and 0 158 319; East German Patent No. 206,896; Japanese Patent Publication No. 51 141895; and French Patent No. 1,381,243. The evolution of the art to the use of the acid catalyzed condensation reaction to generate acyclic alkyleneamines, particularly acyclic polyalkylenepolyamines, as the predominant products stemmed from the initial disclosure in U.S. Pat. No. 4,036,881, though earlier patent literature fairly well characterized such an effect without labeling it so, see U.S. Pat. No. 2,467,205, supra. The acid catalysts are phosphorus compounds and the reaction is carried out in the liquid phase. The trend in this catalyst direction was early set as demonstrated by U.S. Pat. Nos. 2,073,671 and 2,467,205, supra. A modification of this route includes the addition of ammonia to the reaction, see, for example, U.S. Pat. No. 4,394,524 and U.S. Pat. No. 4,463,193 for the purpose of converting alkanolamine such as MEA in situ to alkylene amine such as EDA by reaction with ammonia, and the EDA is in situ reacted with MEA according to the process of U.S. Pat. No. 4,036,881 to form alkyleneamines.

A summary of the prior art employing acid catalysts for making alkyleneamines is set forth in Table 1 below.

TABLE 1

| CITATION | CATALYST TYPE | REACTANTS |
|---|---|---|
| U.S. Pat. No. 2,467,205 | Silica gel, titania gel, alumina, thoria, aluminum phosphate, Preferred catalyst is basic aluminum phosphate. | Vapor phase condensation of EDA over a fixed bed of the catalyst, multipass process shifts from polyethylene-polyamines with the first few cycles. |
| U.S. Pat. No. 4,036,881 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous and phosphoric acids wherein said alkyl groups have from 1 to about 8 carbon atoms and said aryl groups have from 6 to about 20 carbon atoms, alkali metal monosalts of phosphoric acid, the thioanalogs of the foregoing, and mixtures of the above. | Alkanolamine and alkyleneamine in liquid phase reaction. |
| U.S. Pat. No. 4,044,053 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous acids and phosphoric acids wherein said alkyl groups have from 1 to about 8 carbon atoms and said aryl groups have from 6 to about 20 carbon atoms, alkali metal monosalts of phosphoric acid and mixtures of the above. | Alkanepolyols and alkyleneamine in liquid phase reaction. |
| U.S. Pat. No. 4,314,083 | Salt of a nitrogen or sulfur containing substance or the corresponding acid. | Alkanolamine and an alkyleneamine in liquid phase reaction. |
| U.S. Pat. No. 4,316,840 | Metal nitrates and sulfates including zirconium sulfate. | Reforming linear polyamines. |
| U.S. Pat. No. 4,316,841 | Phosphate, preferably boron phosphate. | Reforming linear polyamines. |
| U.S. Pat. No. 4,324,917 | Phosphorus-containing cation exchange resin. | Alkanolamie and an alkyleneamine in liquid phase reaction. |
| U.S. Pat. No. 4,362,886 | Arsenic, antimony or bismuth containing compounds. Antimony sulfate specifically disclosed. | Alkanolamine and an alkyleneamine in liquid phase reaction. |
| U.S. Pat. No. 4,399,308 | Lewis acid halide. | Alkanolamine and an alkyleneamine in liquid phase reaction. |
| U.S. Pat. No. 4,394,524 | Phosphorus-containing substance or salt of a sulfur-containing substance, or the corresponding acid. | Ammonia, alkanolamine and an alkyleneamine in liquid phase reaction. |
| U.S. Pat. No. 4,448,997 | Reacts alumina with phosphoric acid, adds ammonium hydroxide. | EDA with MEA. |
| U.S. Pat. No. 4,463,193 | Group IIIB metal acid phosphate. | Ammonia, alkanolamine and |

TABLE 1-continued

| CITATION | CATALYST TYPE | REACTANTS |
| --- | --- | --- |
| | | an alkyleneamine. |
| U.S. Pat. No. 4,503,253 | Supported phosphoric acid. | Ammonia, alkanolamine and an alkyleneamine. |
| U.S. Pat. No. 4,521,600 | Select hydrogen phosphates and pyrophosphates. | Alkanolamine and an alkyleneamine. |
| U.S. Pat. No. 4,524,143 | Phosphorus impregnated onto zirconium silicate support. | Alkanolamine and an alkyleneamine. |
| U.S. Pat. No. 4,540,822 | Phosphorus compound deposited on a Group IVB metal oxide support. | Alkanolamine and an alkyleneamine, regenerates the catalyst with $O_2$-containing gas. |
| U.S. Pat. No. 4,547,591 | Silica-alumina alone or in combination with an acidic phosphorus cocatalyst. | An ethyleneamine and an alkanolamine; ethyleneamines; or ammonia and an alkanolamine. |
| U.S. Pat. No. 4,550,209 | An intercalatively catalytically active tetravalent zirconium polymeric reaction product of an organo phosphonic acid or an ester thereof with a compound of tetravalent zirconium reactive therewith. | EDA and MEA. |
| U.S. Pat. No. 4,552,961 | Phosphorus amide compound. | Alkyleneamine and alkanolamine and/or alkylene glycol. |
| U.S. Pat. No. 4,555,582 | Phosphorus chemically bonded to a zirconium silicate support. | MEA and EDA. |
| U.S. Pat. No. 4,560,798 | Rare earth metal or strontium acid phosphate. | MEA. |
| U.S. Pat. No. 4,578,517 | Group IIIB metal acid phosphate. | Ammonia or p-/s-amine and alkanolamine. |
| U.S. Pat. No. 4,578,518 | Thermally activated, calcined, pelleted titania containing titanium triphosphate. " . . . the titania that was used was . . . anatase." (Col. 9, lines 18–19). | MEA and EDA. |
| U.S. Pat. No. 4,578,519 | Thermally activated, calcined. pelleted titania with chemically bonded phosphorus derived from polyphosphoric acid. | MEA and EDA with optional recycle of DETA. |
| U.S. Pat. No. 4,584,405 | Activated carbon, optionally treated to incorporate phosphorus. Activated carbon may be washed with strong mineral acid to remove impurities followed by water wash. Optional treatment follows. | MEA and EDA. |
| U.S. Pat. No. 4,584,406 | Pelleted Group IVB metal oxide with chemically bonded phosphorus derived from phosphoryl chloride or bromide. | MEA and EDA. |
| U.S. Pat. No. 4,588,842 | Thermally activated pelleted Group IVB metal oxide with chemically bonded phosphorus. | MEA and EDA. |
| U.S. Pat. No. 4,605,770 | Group IIA or IIIB metal acid phosphate. | Alkanolamine and an alkyleneamine "in liquid phase". |
| U.S. Pat. No. 4,609,761 | Thermally activated pelleted titania with chemically bonded phosphorus. | MEA and EDA. |
| U.S. Pat. No. 4,612,397 | Thermally activated pelleted titania with chemically bonded phosphorus. | MEA and EDA. |
| U.S. Pat. No. 4,617,418 | Acid catalysts, mentions "beryllium sulfate". | Ammonia, alkanolamine and an alkyleneamine "under vapor phase conditions". |
| Japanese Patent Application #1983-185,871, Publication #1985-78,945 | Variety of phosphorus and metal phosphates including Group IVB phosphates. | Ammonia, alkanolamine and ethyleneamine, with ammonia/alkanolamine molar ratio greater than 11. |
| U.S. Pat. No. 4,683,335 | Tungstophosphoric acid, molybdophosphoric acid or mixtures deposited on titania. Examples 2–7 characterize titania surface areas of 51, 60 and 120 $m^2$/gm. | Claims reaction of MEA and EDA, but discloses self-condensation reaction of EDA and DETA. |
| Japanese Patent Application #1985-078,391, Publication #1986-236,752 | Group IVB metal oxide with bonded phosphorus. | Ammonia and MEA. |
| Japanese Patent | Group IVB metal oxide with | Ammonia and MEA. |

TABLE 1-continued

| CITATION | CATALYST TYPE | REACTANTS |
| --- | --- | --- |
| Application #1985-078,392, Publication #1986-236,753 | bonded phosphorus. | |
| U.S. Pat. No. 4,698,427 | Titania having phosphorus thermally chemically bonded to the surface thereof in the form of phosphate bonds. | Diethanolamine and/or hydroxyethyldiethylene-triamine in EDA. |
| U.S. Pat. No. 4,806,517 | Pelleted Group IVB metal oxide with phosphorus thermally chemically bonded to the surface thereof. | MEA and EDA. |

The market demand for higher polyalkylene polyamines such as TETA, TEPA and PEHA has been progressively increasing in recent years. These higher polyalkylene polyamines are desirable co-products with DETA. It would be desirable to satisfy the existing demand from a cost standpoint by modifying slightly the commercial processes directed to the manufacture of DETA from the reaction of MEA and EDA or other suitable starting raw materials such as DETA and AEEA, to the production of TETA, TEPA and PEHA as major products.

It would be desirable to have continuously produced compositions, generated by the reaction of MEA and EDA or other suitable starting raw materials such as DETA and AEEA over a fixed bed of a condensation catalyst under commercial conditions, that are rich in TETA, TEPA and PEHA, and that are not disproportionately high in PIP and other cyclics.

It would be very beneficial to have a process which increases one's ability to generate the manufacture of desirable higher polyalkylene polyamine products such as TETA, TEPA and PEHA without generating large amounts of cyclic alkylenepolyamine products. In addition, it would also be desirable to have a process with raw material flexibility which provides the potential to control congener distribution, linear to cyclic selectivity and linear to branched selectivity of the higher polyalkylene polyamines products. As used herein, congener distribution refers to polyalkylene polyamines containing the same number of nitrogen atoms but not necessarily having the same molecular weight or structure.

The above features are provided by this invention.

SUMMARY OF THE INVENTION

This invention relates in general to vicinal di(-hetero)alkylene organometalates comprising one or more metal oxides in association with one or more amino compounds, glycol compounds or mixtures thereof.

In particular, this invention relates in part to vicinal di(hetero)alkylene organometalates comprising one or more metal oxides in association with one or more alkyleneamines, alkanolamines, alkylene glycols or mixtures thereof.

For purposes of facilitating understanding chemical structures, it has been commonplace in the art to ascribe formula depictions to compounds even though it is well recognized that the actual chemical structure may be different. Using such conventional formula depictions, the vicinal di(hetero)alkylene organometalate compounds of this invention may be represented by the formula:

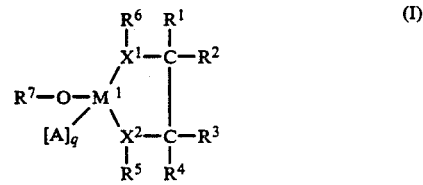
(I)

wherein:

A is independently an oxygen-containing substituent which fills the remaining valencies (g) of $M^1$;

g is independently a value of from 0 to about 4;

$M^1$ is independently a polyvalent metal having a functional positive oxidation state of w wherein the absolute value of w equals the absolute value of (g+2) or (g+3);

$X^1$ and $X^2$ are the same or different and are oxygen or nitrogen;

$R^1$, $R^2$, $R^3$ and $R^4$ are the same or different and are hydrogen or a substituted or unsubstituted hydrocarbyl substituent having from 1 to about 20 carbon atoms;

$R^5$ and $R^6$ are the same or different and are hydrogen, a substituted or unsubstituted hydrocarbyl substituent having from 1 to about 20 carbon atoms, a heteroatom-containing alkylene substituent or a heteroatom-containing alkylene substituent which forms a cyclic structure by linking with $M^1$; and $R^7$ is independently hydrogen, a monovalent metal, a polyvalent metal-containing substituent, a heteroatom-containing alkylene substituent or a vicinal di(-hetero)alkylene organometalate substituent having the formula selected from:

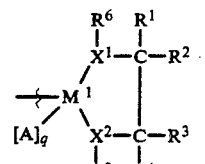

and

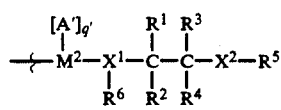

wherein A' is an oxygen-containing substituent which fills the remaining valencies (g') of $M^2$, g' is a value of from 0 to 5, and $M^2$ is a polyvalent metal having a functional positive oxidation state of w' wherein the absolute value of w' equals the absolute value of (g'+2).

The vicinal di(hetero)alkylene organometalate compounds of this invention may also be represented by the formula:

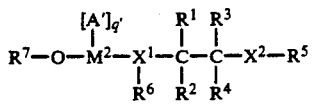

wherein:

A' is independently an oxygen-containing substituent which fills the remaining valencies (g') of $M^2$;

g' is independently a value of from 0 to about 5;

$M^2$ is independently a polyvalent metal having a functional positive oxidation state of w' wherein the absolute value of w' equals the absolute value of (g'+2);

$X^1$ and $X^2$ are the same or different and are oxygen or nitrogen;

$R^1$, $R^2$, $R^3$ and $R^4$ are the same or different and are hydrogen or a substituted or unsubstituted hydrocarbyl substituent having from 1 to about 20 carbon atoms;

$R^5$ and $R^6$ are the same or different and are hydrogen, a substituted or unsubstituted hydrocarbyl substituent having from 1 to about 20 carbon atoms or a heteroatom-containing alkylene substituent; and $R^7$ is independently hydrogen, a monovalent metal, a polyvalent metal-containing substituent, a heteroatom-containing alkylene substituent or a vicinal di(hetero)alkylene organometalate substituent having the formula selected from:

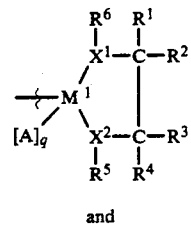

and

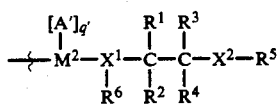

wherein A is an oxygen-containing substituent which fills the remaining valencies (g) of $M^1$, g is a value of from 0 to about 4, and $M^1$ is a polyvalent metal having a functional positive oxidation state of w wherein the absolute value of w equals the absolute value of (g+2) or (g+3).

This invention also relates in part to a process for making vicinal di(hetero)alkylene organometalates which comprises contacting one or more metal oxides with one or more amino compounds, glycol compounds or mixtures thereof at a temperature and pressure sufficient to provide vicinal di(hetero)alkylene organometalates.

In particular, this invention relates in part to a process for making vicinal di(hetero)alkylene organometalates which comprises contacting one or more metal oxides with one or more alkanolamines, alkyleneamines, alkylene glycols or mixtures thereof at a temperature and pressure sufficient to provide vicinal di(hetero)alkylene organometalates.

This invention further relates in part to reaction products prepared by providing in intimate contact one or more metal oxides and one or more amino compounds, glycol compounds or mixtures thereof at a temperature and pressure sufficient for effecting the reaction.

In particular, this invention relates in part to reaction products prepared by providing in intimate contact one or more metal oxides and one or more alkanolamines, alkyleneamines, alkylene glycols or mixtures thereof at a temperature and pressure sufficient for effecting the reaction.

This invention ye further relates in part to a process for making amines which comprises (i) contacting one or more metal oxides with one or more amino compounds, glycol compounds or mixtures thereof at a temperature and pressure sufficient to provide a first vicinal di(hetero)alkylene organometalate compound, (ii) contacting said first vicinal di(hetero)alkylene organometalate compound with one or more amino compounds or mixtures thereof at a temperature and pressure sufficient to provide a second vicinal di(hetero)alkylene organometalate compound, and (iii) displacing the amine from said second vicinal di(hetero)alkylene organometalate compound.

In particular, this invention relates in part to a process for making amines which comprises (i) contacting one or more metal oxides with one or more alkanolamines, alkyleneamines, alkylene glycols or mixtures thereof at a temperature and pressure sufficient to provide a first vicinal di(hetero)alkylene organometalate compound, (ii) contacting said first vicinal di(hetero)alkylene organometalate compound with one or more alkanolamines, alkyleneamines or mixtures thereof at a temperature and pressure sufficient to provide a second vicinal di(hetero)alkylene organometalate compound, and (iii) displacing the amine from said second vicinal di(hetero)alkylene organometalate compound.

More particularly, this invention relates in part to a process of making amines by the (i) intramolecular condensation of an amino compound to an amine having a lower molecular weight or (ii) the intermolecular condensation of an amino compound with one or more of another amino compound or a compound containing an alcoholic hydroxyl group using the vicinal di(hetero)alkylene organometalate compounds of this invention. A preferred process involves the manufacture of alkyleneamines, most desirably higher polyalkylene polyamines, by such condensation reactions utilizing a vicinal di(hetero)alkylene organometalate compound containing tungsten, titanium or mixtures thereof.

The invention further relates in part to a continuously generated alkyleneamines producers composition comprising, based on 100 percent of the weight of the composition and exclusive of any water and/or ammonia present, a) greater than about 3.0 weight percent of the combination of TETA and TEPA, b) greater than about 0.1 weight percent of TEPA, c) greater than about 3.0 weight percent of TETA, d) less than about 90.0 weight percent of DETA and/or EDA, e) less than about 90.0 weight percent of MEA and/or AEEA, f) less than about 12.5 weight percent of the combination of PIP and AEP, g) less than about 15.0 weight percent of other polyalkylene polyamines, h) a TETA+TAEA to PIP+AEP+ DPE weight ratio of greater than about 0.5, i) a TEPA+AETAEA to PIP+AEP+PEEDA+-
DAEP+DPE+AEPEEDA+iAEPEEDA+A-
EDAEP +AEDPE+BPEA weight ratio of greater
than about 0 5, j) a TETA to TAEA weight ratio of greater than
about 6 0, and k) a TEPA to AETAEA weight ratio of greater than
about 1 0.

As used herein, the term "amino compound" embraces ammonia and any compound containing nitrogen to which is bonded an active hydrogen. Also, for purposes of this invention, the term "oxide") embraces oxides, hydroxides and/or mixtures thereof.

For purposes of this invention, the chemical elements are identified in accordance with the Periodic Table of the Elements, CAS version, Handbook of Chemistry and Physics, 67th Ed., 1986-87, inside cover. Also, for purposes of this invention, Group IIIB metal oxides embraces the lanthanides and actinides.

DETAILED DESCRIPTION

The higher polyalkylene polyamines such as TETA, TEPA and PEHA are very useful commercial products for a variety of applications including fuel oil additives, corrosion inhibitors, fabric softeners, fungicides and others. As indicated above, there is lacking a commercial process for the manufacture of enhanced quantities of TETA, TEPA and PEHA especially as significant products of reaction. There is thus a need for the ability to commercially generate larger production quantities of TETA, TEPA and PEHA and that is the direction of this invention. The process of this invention provides for the reaction of MEA and DETA or other suitable starting raw materials such as EDA and AEEA to produce in a continuous manner a reaction product mixture, termed herein an "alkyleneamines producers composition", in which TETA, TEPA and PEHA are principal products of the reaction.

The process of this invention is distinctive insofar as it achieves the generation of high concentrations of TETA, TEPA and PEHA in a manner which can be suitably employed in a commercial process, particularly a continuous process, for the manufacture of alkyleneamines. In particular, the process of this invention allows the production of TETA, TEPA and PEHA in relatively high yields without generating large amounts of cyclic polyalkylene polyamine products. The process of this invention provides starting raw material flexibility thereby allowing the potential to control congener distribution, linear to cyclic selectivity and linear to branched selectivity of the higher polyalkylene polyamine products.

As indicated above, this invention relates in general to vicinal di(hetero)alkylene organometalates comprising one or more metal oxides in association with one or more amino compounds, glycol compounds or mixtures thereof.

In particular, this invention relates in part to vicinal di(hetero)alkylene organometalates comprising one or more metal oxides in association with one or more alkyleneamines, alkanolamines, alkylene glycols or mixtures thereof.

The vicinal di(hetero)alkylene organometalate compounds of this invention may be represented by the formula:

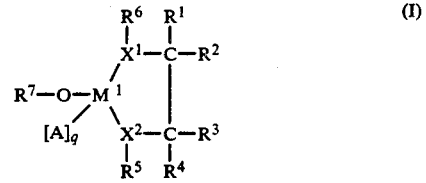

wherein

A is independently an oxygen-containing substituent which fills the remaining valencies (g) of $M^1$;

g is independently a value of from 0 to about 4;

$M^1$ is independently a polyvalent metal having a functional positive oxidation state of w wherein the absolute value of w equals the absolute value of (g+2) or (g+3);

$X^1$ and $X^2$ are the same or different and are oxygen or nitrogen;

$R^1$, $R^2$, $R^3$ and $R^4$ are the same or different and are hydrogen or a substituted or unsubstituted hydrocarbyl substituent having from 1 to about 20 carbon atoms;

$R^5$ and $R^6$ are the same or different and are hydrogen, a substituted or unsubstituted hydrocarbyl substituent having from 1 to about 20 carbon atoms, a heteroatom-containing alkylene substituent or a heteratom-containing alkylene substituent which forms a cyclic structure by linking with $M^1$; and $R^7$ is independently hydrogen, a monovalent metal, a polyvalent metal-containing substituent, a heteroatom-containing alkylene substituent or a vicinal di(hetero)alkylene organometalate substituent having the formula selected from:

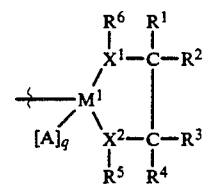

and

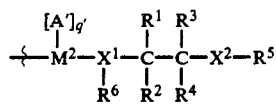

wherein A' is an oxygen-containing substituent which fills the remaining valencies (g') of $M^2$, g' is a value of from 0 to 5, and $M^2$ is a polyvalent metal having a functional positive oxidation state of w' wherein the absolute value of w' equals the absolute value of (g'+2).

The vicinal di(hetero)alkylene organometalate compounds of this invention may also be represented by the formula:

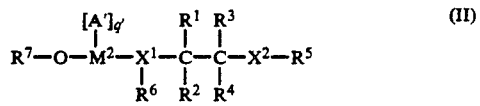

wherein:

A ' is independently an oxygen-containing substituent which fills the remaining valencies (g') of $M^2$;

g' is independently a value of from 0 to about 5;

$M^2$ is independently a polyvalent metal having a functional positive oxidation state of w' wherein the absolute value of w' equals the absolute value of (g'+2);

$X^1$ and $X^2$ are the same or different and are oxygen or nitrogen;

$R^1$, $R^2$, $R^3$ and $R^4$ are the same or different and are hydrogen or a substituted or unsubstituted hydrocarbyl substituent having from 1 to about 20 carbon atoms;

$R^5$ and $R^6$ are the same or different and are hydrogen, a substituted or unsubstituted hydrocarbyl substituent having from 1 to about 20 carbon atoms or a heteroatom-containing alkylene substituent; and $R^7$ is independently hydrogen, a monovalent metal, a polyvalent metal-containing substituent, a heteroatom-containing alkylene substituent or a vicinal di(-hetero)alkylene organometalate substituent having the formula selected from:

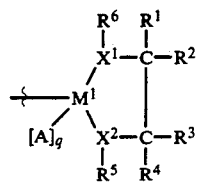

and

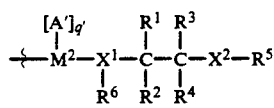

wherein A is an oxygen-containing substituent which fills the remaining valencies (g) of $M^1$, g is a value of from 0 to about 4, and $M^1$ is a polyvalent metal having a functional positive oxidation state of w wherein the absolute value of w equals the absolute value of (g+2) or (g+3).

The A substituent of the vicinal di(hetero)alkylene organometalates depicted in the formulae above includes oxygen-containing substituents which fill the remaining valencies (g) of $M^1$. In particular, the A substituent can be a monovalent metal oxygen-containing substituent, a polyvalent metal oxygen-containing substituent, a hydroxyl substituent, a heteroatom-containing alkylene substituent, a vicinal di(hetero)alkylene organometalate substituent having the formula selected from:

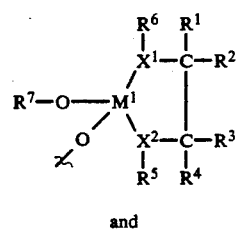

and

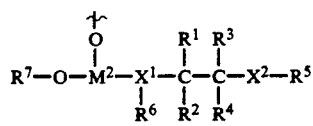

or an oxygen-containing substituent having the formula:

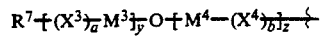

wherein $X^3$ is an oxygen-containing substituent which fills the remaining valencies (a) of $M^3$, $X^4$ is an oxygen-containing substituent which fills the remaining valencies (b) of $M^4$, a is a value of from 1 to about 5, b is a value from 1 to about 5, $M^3$ is a polyvalent metal having a functional positive oxidation state of u wherein the absolute value of u equals the absolute value of (u+2), $M^4$ is a polyvalent metal having a functional positive oxidation state of v wherein the absolute value of v equals the absolute value of (v+2), y is a value of 0 or greater and z is a value of 0 or greater, provided that when y is a value of 1 or greater then at least one of $X^3$ is bonded to $R^7$ and when z is a value of 1 or greater then at least one of $X^4$ is bonded to $M^1$. The substituent A can be bonded to $M^1$ through an ol (hydroxyl) or oxo (oxygen) linkage.

The A' substituent of the vicinal di(hetero)alylene organometalates depicted in the formulae above includes oxygen-containing substituents which fill the remaining valencies (g') of $M^2$. In particular, the A' substituent can be a monovalent metal oxygen-containing substituent, a polyvalent metal oxygen-containing substituent, a hydroxyl substituent, a heteratom-containing alkylene substituent, a vicinal di(hetero)alkylene organometalate substituent having the formula selected from:

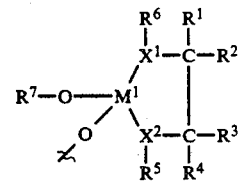

and

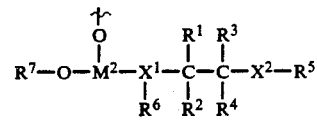

or an oxygen-containing substituent having the formula:

wherein $X^3$ is an oxygen-containing substituent which fills the remaining valencies (a) of $M^3$, $X^4$ is an oxygen-containing substituent which fills the remaining valencies (b) of $M^4$, a is a value of or from 1 to about 5, b is a value from 1 to about 5, $M^3$ is a polyvalent metal having a functional positive oxidation state of u wherein the absolute value of u equals the absolute value of (u+2), $M^4$ is a polyvalent metal having a functional positive oxidation state of v wherein the absolute value of v equals the absolute value of (v+2), y is a value of 0 or greater and z is a value of 0 or greater, provided that when y is a value of 1 or greater then at least one of $X^3$ is bonded to $R^7$ and when z is a value of 1 or greater then at least one of $X^4$ is bonded to $M^2$. The substituent A' can be bonded to $M^2$ through an ol (hydroxyl) or oxo (oxygen) linkage.

It is appreciated that values for y and z may vary over a wide range to include various polymeric forms of the vicinal di(hetero)alkylene organometalates.

For the purposes of this invention, substituents depicted alike in the chemical structures herein can be the same or different except as otherwise indicated.

The $M^1$ substituent of the vicinal di(hetero)alkylene organometalates depicted in the formulae above is a polyvalent metal having a functional positive oxidation state of w wherein the absolute value of w equals the absolute value of $(g+2)$ or $(g+3)$. The absolute value of w can be $(g+2)$ when either $X^1$ or $X^2$ is a coordination bond, and the absolute value of w can be $(g+3)$ when either $X^1$ or $X^2$ is a covalent bond. The $M^2$ substituent of the vicinal di(hetero)alkylene organometalates depicted in the formulae above is a polyvalent metal having a functional positive oxidation state of w wherein the absolute value of w' equals the absolute value of $(g+2)$. The $M^3$ substituent of the vicinal di(hetero)alkylene organometalates depicted in the formulae above is a polyvalent metal having a functional positive oxidation state of u wherein the absolute value of u equals the absolute value of $(u+2)$. The $M^4$ substituent of the vicinal di(hetero)alkylene organometalates depicted in the formulae above is a polyvalent metal having a functional positive oxidation state of v wherein the absolute value of v equals the absolute value of $(v+2)$. Suitable polyvalent metals for use herein have a positive functional oxidation state of at least +2, say +3, +4, +6 or +7. Preferred polyvalent metals include those which provide coordination bonding through the beta-substituted heteroatom to afford the cyclic vicinal di(hetero)alkylene organometalates of formula I above.

Illustrative of polyvalent metals encompassed by $M^1$ and $M^2$ include, for example, Group IIIB metals, Group IVB metals, Group VB metals, Group VIB metals, Group VIIB metals, Group VIII metals, Group IIIA metals, Group IVA metals, Group VA metals and Group VIA metals. Illustrative of polyvalent metals encompassed by $M^3$ and $M^4$ include, for example, the polyvalent metals described above for $M^1$ and $M^2$ in addition to Group IIA metals, Group VIII metals, Group IB metals and Group IIB metals. Preferred polyvalent metals include, for example, tungsten, titanium, vanadium, molybdenum, zirconium, silicon and mixtures thereof.

For polyvalent metal containing substituents, polyvalent metal oxygen containing substituents, monovalent metal substituents and monovalent metal oxygen containing substituents of the vicinal di(hetero)alkylene organometalates, the permissible metals include, as appropriate for the particular valencies, the polyvalent metals described above for $M^3$ and $M^4$ in addition to Group IA metals.

The heteroatom containing alkylene substituent of the vicinal di(hetero)alkylene organometalates includes, for example, alkanolamine substituents, alkyleneamine substituents, polyalkylene polyamine substituents and the like. The heteroatom containing alkylene substituent can contain one or more heteroatoms which can be the same or different.

The $X^1$ and $X^2$ substituents of the vicinal di(hetero)alkylene organometalate depicted in the formulae above include oxygen or nitrogen. The $X^1$ and $X^2$ substituents may vary over the course of reaction, e.g., from oxygen to nitrogen or vice versa, and this degree of substituent interchange will ultimately be governed by the preferred affinity of the metal for oxygen or nitrogen.

The $X^3$ substituent of the vicinal di(hetero)alkylene organometalates depicted in the formulae above includes oxygen containing substituents which fill the remaining valencies (a) of $M^3$. The $X^4$ substituent of the vicinal di(hetero)alkylene organometalates depicted in the formulae above includes oxygen containing substituents which fill the remaining valencies (b) of $M^4$. Preferred oxygen containing substituents include, for example, oxygen and hydroxyl. Bonding can occur through an ol (hydroxyl) or oxo (oxygen) linkage.

The $R^1$, $R^2$, $R^3$, $R^4$, $R^5$ and $R^6$ substituents of the vicinal di(hetero)alkylene organometalates may be the same or different and are hydrogen or hydrocarbyl, including substituted hydrocarbyl, of 1 to 20, preferably 1 to 6 or 8 carbon atoms. Often $R^1$, $R^2$, $R^3$, $R^4$, $R^5$ and $R^6$ are hydrogen, alkyl of between 1 and about 10 carbon atoms, monocyclic or bicyclic aryl having up to about 12 carbon atoms, alkaryl having 7 to about 10 carbon atoms, monocyclic or bicyclic aralkyl having 7 to about 15 carbon atoms, alkenyl having 2 to 3 carbon atoms, cycloalkyl having 3 to about 8 carbon atoms, and cyclic structures joining two of $R^1$, $R^2$, $R^3$, $R^4$, $R^5$ and $R^6$ having 3 to about 8 carbon atoms. In addition, the $R^5$ and $R^6$ substituents may independently be a heteroatom-containing alkylene substituent. For formula I above, the $R^5$ and $R^6$ substituents may independently be a heteroatom-containing alkylene substituent which forms a cyclic structure by linking with $M^1$.

The $R^7$ substituent of the vicinal di(hetero)alkylene organometalates depicted in the formulae above is hydrogen, a monovalent metal, a polyvalent metal-containing substituent, a heteroatom-containing alkylene substituent or a vicinal di(hetero)alkylene organometalate substituent having the formula selected from:

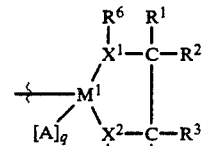

and

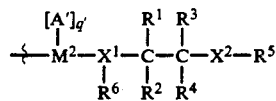

wherein the substituents are as defined above.

It is appreciated that chelation may be provided by certain substituents of the vicinal di(hetero)alkylene organometalates. For purposes of this invention, the formulae depicted herein embrace any permissible coordinate valence forces.

The general structure of the vicinal di(hetero)alkylene organometalates of this invention may be responsible for improved selectivity to acyclic amine products due to increased steric hinderance or chelation to preclude intramolecular cyclic amines formation. The vicinal di(hetero)alkylene organo metalates should be amenable to displacement by a suitable nucleophile such as an alkyleneamine or alkanolamine in order to form the desired amine product. Suitable nucleophiles can react with the vicinal di(hetero)alkylene organometalate compounds from the bulk, i.e., not associated with a catalytic site, or with proximally bound (coordinated) vicinal di(hetero)alkylene organometalates. This nuclophile displacement will be governed by the electronic properties of $M^1$ and $M^2$ including bond energies and electron affinities. It has been found that these properties can be altered by the utilization of other metal oxides in the preparation of vicinal di(hetero) alkylene organometalates, for example, a major metal oxide in association with one or more minor metal oxides.

Particularly preferred major metal oxides for use in this invention include, for example, one or more oxides of titanium, zirconium, hafnium, aluminum, boron, gallium, germanium, tin, iron, vanadium, niobium, tantalum, antimony, uranium, thorium, silicon, zinc and the lanthanides. Representative metalates which readily form the vicinal di(hetero)alkylene organometalates when contacted with an alkanolamine, as alkyleneamine, an alkylene glycol or mixtures thereof include, for example, titanates, aluminates, silicates, stannates, borates and the like. The metalate anion comprises at least one di(hetero)alkylene moiety, however, more than one di(hetero)alkylene moiety is possible since it is recognized that the actual chemical formula under the reaction conditions of the process is subject to change. As indicated above, these complexes should be amenable to reaction with suitable nucleophiles.

Suitable minor metal oxides are selected on the basis of electrophilicity and coordination with the major metal oxide For example, one or more minor metal oxides are chosen which will increase the electropositive nature of the major metal oxide and thus effectuate the formation of the vicinal di(hetero)alkylene organometalates. Preferred minor metal oxides include, for example, any of the major metal oxides described above and additionally bismuth, osmium, iridium, rhenium, molybdenum, chromium and tungsten As described more fully below, the minor metal oxides may be introduced as impregnates on the major metal oxide by conventional procedures known in the art such as incipient wetness or by co precipitation or mulling of the mixed metal oxides which affords a more uniform distribution. The minor metal oxides may also form vicinal di(hetero)alkylene organometalates which alters the product mix vis-a-vis the major metal oxide.

In an embodiment of this invention, an oxyacid having a divalent or polyvalent anion or a divalent or polyvalent metal salt of an oxyacid or mixtures thereof may be introduced as impregnates to improve the metal oxide(s) performance (activity/ selectivity/stability). These polyoxyanions can alter the electronic properties of the metal oxide(s) and thus effectuate the formation of vicinal di(hetero)alkylene organometalates. While not wishing to be bound to any particular theory, it is believed that these polyoxyanions serve as bridging ligands and may not be involved with the formation of the vicinal di(hetero)alkylene organometalate per se. Suitable oxyacids having a divalent or polyvalent anion or a divalent or polyvalent metal salt of an oxyacid include, for example, sulfuric acid, phosphoric acid, tungstic acid, molybdic acid, telluric acid, selenic acid, tunstophosphoric acid, silicotungstic acid, ammonium metatungstate, sodium tetraborate and the like including mixtures thereof.

As indicated above, this invention also relates in part to a process for making vicinal di(hetero)alkylene organometalates which comprises contacting one or more metal oxides with one or more amino compounds, glycol compounds or mixtures thereof at a temperature and pressure sufficient to provide vicinal di(hetero)alkylene organometalates.

In particular, this invention relates in part to a process for making vicinal di(hetero)alkylene organometalates which comprises contacting one or more metal oxides with one or more alkanolamines, alkyleneamines, alkylene glycols or mixtures thereof at a temperature and pressure sufficient to provide vicinal di(hetero)alkylene organometalates.

As indicated above, this invention further relates in part to reaction products prepared by providing in intimate contact one or more metal oxides and one or more amino compounds, glycol compounds or mixtures thereof at a temperature and pressure sufficient for effecting the reaction.

In particular, this invention relates in part to reaction products prepared by providing in intimate contact one or more metal oxides and one or more alkanolamines, alkyleneamines, alkylene glycols or mixtures thereof at a temperature and pressure sufficient for effecting th reaction.

As indicated above, this invention yet further relates in part to a process for making amines which comprises (i) contacting one or more metal oxides with one or more amino compounds, glycol compounds or mixtures thereof at a temperature and pressure sufficient to provide a first vicinal di(hetero)alkylene organometalate compound, (ii) contacting said first vicinal di(hetero)alkylene organometalate compound with one or more amino compounds or mixtures thereof at a temperature and pressure sufficient to provide a second vicinal di(hetero)alkylene organometalate compound, and (iii) displacing the amine from said second vicinal di(hetero)alkylene organometalate compound.

In particular, this invention relates in part to a process for making amines which comprises (i) contacting one or more metal oxides with one or more alkanolamines, alkyleneamines, alkylene glycols or mixtures thereof at a temperature and pressure sufficient to provide a first vicinal di(hetero)alkylene organometalate compound, (ii) contacting said first vicinal di(hetero)alkylene organometalate compound with one or more alkanolamines, alkeneamines or mixtures thereof at a temperature and pressure sufficient to provide a second vicinal di(hetero)alkylene organometalate compound, and (iii) displacing the amine from said second vicinal di(hetero)alkylene organometalate compound.

This invention embraces a process for making alkyleneamines, in particular, polyalkylene polyamines, which comprises (i) contacting one or more metal oxides with one or more alkyleneamines at a temperature and pressure sufficient to provide a first vicinal di(hetero)alkylene organometalate compound, (ii) contacting said first vicinal di(hetero)alkylene organometalate compound with on or more alkanolamines at a temperature and pressure sufficient to provide a second vicinal di(hetero)alkylene organometalate compound, and (iii) displacing the polyalkylene polyamine from said second vicinal di(hetero)alkylene organometalate compound.

This invention also embraces a process for making alkyleneamines, in particular, polyalkylene polyamines, which comprises (i) contacting one or more metal oxides with one or more alkanolamines at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the polyalkylene polyamine from said second vicinal di(hetero)alkylene organometalate compound.

This invention further embraces a process for making alkyleneamines, in particular, polyalkylene polyamines, which comprises (i) contacting one or more metal oxides with one or more alkyleneamines at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the polyalkylene polyamine from said second vicinal di(hetero)alkylene organometalate compound.

This invention yet further embraces a process for making alkanolamines which comprises (i) contacting one or more metal oxides with one or more alkanolamines at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the alkanolamine from said second vicinal di(hetero)alkylene organometalate compound.

The invention embraces a process for making alkanolamines which comprises (i) contacting one or more metal oxides with one or more alkyleneamines at a temperature and pressure sufficient to provide a first vicinal di(hetero)alkylene organometalate compound, (ii) contacting said first vicinal di(hetero)alkylene organometalate compound with one or more alkanolamines at a temperature and pressure sufficient to provide a second vicinal di(hetero)alkylene organometalate compound, and (iii) displacing the alkanolamine from said second vicinal di(hetero)alkylene organometalate compound.

This invention also embraces a process for making alkanolamines which comprises (i) contacting one or more metal oxides with one or more alkanolamines at a temperature and pressure sufficient to provide a first vicinal di(hetero)alkylene organometalate compound, (ii) contacting said first vicinal di(hetero)alkylene organometalate compound with one or more alkanolamines at a temperature and pressure sufficient to provide a second vicinal di(hetero)alkylene organometalate compound, and (iii) displacing the alkanolamine from said second vicinal di(hetero)alkylene organometalate compound.

This invention further embraces a process for making alkanolamines which comprises (i) contacting one or more metal oxides with one or more alkylene glycols at a temperature and pressure sufficient to provide a first vicinal i(hetero)alkylene organometalate compound, (ii) contacting said first vicinal di(hetero)alkylene organometalate compound with one or more alkanolamines at a temperature and pressure sufficient to provide a second vicinal di(hetero)alkylene organometalate compound, and (iii) displacing the alkanolamine from said second vicinal di(hetero)alkylene organometalate compound.

This invention yet further embraces a process for making alkanolamines which comprises (i) contacting on or more metal oxides with one or more alkylene glycols at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the alkanolamine form said second vicinal di(hetero)alkylene organometalate compound This invention yet further embraces a process for making alkyleneamines which comprises (i) contracting one or more metal oxides with one or more alkylene glycols at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the alkyleneamine from said second vicinal di(hetero)alkylene organometalate compound.

For purposes of this invention, it is recognized that the first vicinal di(hetero)alkylene organometalate compound can be contacted with one or more amino compounds or mixtures thereof at a temperature and pressure sufficient to provide an amine with substantially concurrent displacement of the amine from the first vicinal di(hetero)alkylene organometalate compound. Thus, a second vicinal di(hetero)alkylene organometalate compound may or may not be formed in the process of this invention. However, the formation of a second vicinal di(hetero)alkylene organometalate compound may provide improved linear/branched product ratios for the TETA's and higher polyalkylene polyamines. It is also recognized that more than two vicinal di(hetero)alkylene organometalate compounds may be formed in the process of this invention prior to displacing the amine therefrom.

As also indicated above, this invention relates to a continuously generated alkyleneamines producers composition comprising, based on 100 percent of the weight of the composition and exclusive of any water and/or ammonia present, a) greater than about 3.0 weight percent of the combination of TETA and TEPA, 7 b) greater than about 0.1 weight percent of TEPA, c) greater than about 3.0 weight percent of TETA, d) less than about 90.0 weight percent of DETA and/or EDA, e) less than about 90.0 weight percent of MEA and/or AEEA, f) less than about 12.5 weight percent of the combination of PIP and AEP, less than about 15.0 weight percent of other polyalkylene polyamines, h) a TETA+TAEA to PIP+AEP+PEEDA+DAEP+DPE weight ratio of greater than about 0.5, i) a TEPA+AETAEA to PIP+AEP+PEEDA+DAEP+DPE+AEPEEDA+iAEPEEDA+AEDAEP+AEDPE+BPEA weight ratio of greater than about 0.5, j) a TETA to TAEA weight ratio of greater than about 6.0, and k) a TEPA to AETAEA weight ratio of greater than about 1.0.

The alkyleneamines producers composition of this invention can be subjected to conventional separations techniques for recovering the individual components of the composition. Such techniques are well known in the art and include, for example, distillation.

This invention contemplates the catalyzed condensation by (i) intramolecular condensation of an amino compound to an amine having a lower molecular weight, and (ii) intermolecular condensation of an amino compound with one or more of another amino compound or a compound containing an alcohol hydroxyl group to an amine having a lower, same or higher molecular weight than the reactants, using the vicinal di(hetero)alkylene organometalate compounds of this invention.

The vicinal di(hetero)alkylene organometalate compounds of this invention comprise one or more metal oxides in association with an alkanolamine, an alkyleneamine, an alkylene glycol or mixtures thereof. The one or more metal oxides are effective as catalysts in the process of this invention. Preferred metal oxides are amphoteric or slightly acidic or slightly basic. Although acidity is thought to play some role in the activity of these metal oxides, it is believed that the improved activity and selectivity exhibited by these metal oxides cannot be attributed solely to an increase in either Lewis or Bronsted acidity. Illustrative of such metal oxides which may be utilized in the vicinal di(hetero)alkylene organometalates of this invention include, for example, one or more of the following: Group IA metal oxides, Group IIA metal oxides, Group IIIB metal oxides (including lanthanides and actinides), Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides and Group IVB metal oxides or mixtures thereof. Preferred metal oxides which may be utilized in preparing the vicinal di(hetero)alkylene organometalates include, for example, one or more oxides of beryllium, scandium, yttrium, terbium, dysprosium, holmium, erbium, thulium, ytterbium, lutetium, titanium, zirconium, hafnium, vanadium, niobium, tantalum, iron, cobalt, zinc, silver, aluminum, gallium, indium, silicon, tungsten, germanium, tin, lead, arsenic, antimony and bismuth.

Group IVA, IVB and VIB metal oxides such as silica, titanium dioxide, zirconium dioxide and tungsten oxide are preferred for use in this invention. For mixed metal oxides in which at least one of the metals is titanium, suitable metals in association with titanium may include, for example, one or more of the following: Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IIIA metals such as boron, aluminum, gallium and indium, Group IVA metals such as silicon, germanium, tin and lead, Group VA metals such as arsenic, antimony and bismuth, and Group IVB metals such as zirconium and hafnium. For mixed metal oxides in which at least one of the metals is zirconium, suitable metals in association with zirconium may include, for example, one or more of the following: Group IVA metals such as silicon, germanium, tin and lead, Group VB metals such as niobium and tantalum and Group VIB metals such as chromium, molybdenum and tungsten. The virtue of these metal oxides is that they can contribute to product selectivity, reaction activity and/or mechanical or dimensional strength of the support described below.

Illustrative of mixed metal oxides which may be used in the vicinal di(hetero)alkylene organometalates include, for example, $TiO_2$—$SiO_2$, $TiO_2$—$Al_2O_3$, $TiO_2$—$CdO$, $TiO_2$—$Bi_2O_3$, $TiO_2$—$Sb_2O_5$, $TiO_2$—$SnO_2$, $TiO_2$—$ZrO_2$, $TiO_2$—$BeO$, $TiO_2$—$MgO$, $TiO_2$—$CaO$, $TiO_2$—$SrO$, $TiO_2$—$ZnO$, $TiO_2$—$Ga_2O_3$, $TiO_2$—$Y_2O_3$, $TiO_2$—$La_2O_3$, $TiO_2$—$MoO_3$, $TiO_2$—$Mn_2O_3$, $TiO_2$—$Fe_2O_3$, $TiO_2$—$Co_3O_4$, $TiO_2$—$WO_3$, $TiO_2$—$V_2O_5$, $TiO_2$—$CaO$, $TiO_2$—$HfO_2$, $TiO_2$—$Li_2O$, $TiO_2$—$Nb_2O_5$, $TiO_2$—$Ta_2O_5$, $TiO_2$—$Gd_2O_3$, $TiO_2$—$Lu_2O_3$, $TiO_2$—$Yb_2O_3$, $TiO_2$—$CeO_2$, $TiO_2$—$Sc_2O_3$, $TiO_2$—$PbO$, $TiO_2$—$NiO$, $TiO_2$—$CuO$, $TiO_2$—$CoO$, $TiO_2$—$B_2O_3$, $ZrO_2$—$SiO_2$, $Zro_2$—$Al_2O_3$, $ZrO_2$—$SnO$, $ZrO_2$—$PbO$, $ZrO_2$—$Nb_2O_5$, $ZrO_2$—$Ta_2O_5$, $ZrO_2$—$Cr_2O_3$, $ZrO_2$—$MoO_3$, $ZrO_2$—$WO_3$, $ZrO_2$—$TiO_2$, $ZrO_2$—$HfO_2$, $TiO_2$—$SiO_2$—$Al_2O_3$, $TiO_2$—$SiO_2$—$ZnO$, $TiO_2$—$SiO_2$—$ZrO_2$, $TiO_2$—$SiO_2$—$CuO$, $TiO_2$—$SiO_2$—$MgO$, $TiO_2$—$SiO_2$—$Fe_2O_3$, $TiO_2$—$SiO_2$—$B_2O_3$, $TiO_2$—$SiO_2$—$WO_3$, $TiO_2$—$SiO_2$—$Na_2O$, $TiO_2$—$SiO_2$—$MgO$, $TiO_2$—$SiO_2$—$La_2O_3$, $TiO_2$—$SiO_2$—$Nb_2O_5$, $TiO_2$—$SiO_2$—$Mn_2O_3$, $TiO_2$—$SiO_2$—$Co_3O_4$, $TiO_2$—$SiO_2$—$NiO$, $TiO_2$—$SiO_2$—$PbO$, $TiO_2$—$SiO_2$—$Bi_2O_3$, $TiO_2$—$Al_2O_3$—$ZnO$, $TiO_2$—$Al_2O_3$—$ZrO_2$, $TiO_2$—$Al_2O_3$—$Fe_2O_3$, $TiO_2$—$Al_2O_3$—$WO_3$, $TiO_2$—$Al_2O_3$—$La_2O_3$, $TiO_2$—$Al_2O_3$—$Co_3O_4$, $ZrO_2$—$SiO_2$—$Al_2O_3$, $ZrO_2$—$SiO_2$—$SnO$, $ZrO_2$—$SiO_2$—$Nb_2O_5$, $ZrO_2$—$SiO_2$—$WO_3$, $ZrO_2$—$SiO_2$—$TiO_2$, $ZrO_2$—$SiO_2$—$MoO_3$, $ZrO_2$—$SiO_2$—$HfO_2$, $ZrO_2$—$SiO_2$—$Ta_2O_5$, $ZrO_2$—$Al_2O_3$—$SiO_2$, $ZrO_2$—$Al_2O_3$—$PbO$, $ZrO_2$—$Al_2O_3$—$Nb_2O_5$, $ZrO_2$—$Al_2O_3$—$WO_3$, $ZrO_2$—$Al_2O_3$—$TiO_2$, $ZrO_2$—$Al_2O_3$—$MoO_3$, $ZrO_2$—$HfO_2$—$Al_2O_3$, $ZrO_2$—$HfO_2$—$TiO_2$, and the like. Other suitable mixed metal oxides embraced within the scope of this invention are disclosed by Tanabe et al., Bulletin of the Chemical Society of Japan, Vol. 47(5), pp. 1064–1066 (1974).

The metal oxides described herein which can be used in preparing the vicinal di(hetero)alkylene organometalates of this invention may contribute to product selectivity, activity of the reaction and/or stability of the vicinal di(hetero)alkylene organometalate. The vicinal di(hetero)alkylene organometalate structure can comprise from about 0 to about 90 percent or greater by weight of the metal oxide, preferably from about 0 to about 75 percent by weight of the metal oxide, and more preferably from about 0 to about 50 percent by weight of the metal oxide, the remainder being the weight of the alkanolamine, alkyleneamine, alkylene glycol or mixtures thereof. For mixed metal oxides containing titania, higher concentrations of titania can provide very desirable product selectivities including acyclic to cyclic selectivities and linear to branched selectivities of higher polyalkylene polyamine products As discussed hereinafter, the one or more metal oxides used in this invention may also contain support(s), binding agent(s) or other additives to stabilize or otherwise help in the manufacture of the vicinal di(hetero)alkylene organometalates.

The one or more metal oxides used in this invention should have a surface area greater than about 25 $m^2/gm$ to as high as about 260 $m^2/gm$ or greater depending upon which metal oxide described below that is employed. In the case of titanium oxides, the surface area should be greater than about 140 $m^2/gm$ to as high as about 260 $m^2/gm$, more preferably, greater than about 160 $m^2/gm$ to as high as about 260 $m^2/gm$, determined according to the single point $N_2$ method. In the case of zirconia oxides, the surface area should be greater than about 70 $m^2/gm$ to as high as about 150 $m^2/gm$, more preferably, greater than about 90 $m^2/gm$ to as high as about 135 $m^2/gm$, determined according to the single point $N_2$ method. It is appreciated that the performance moderators described below can affect the surface area of the one or more metal oxides. While surface areas described above may be preferred, for purposes of this invention, the surface area of the one or more metal oxides should be sufficient to contribute to product selectivity, reaction activity and/or mechanical or dimensional strength of the support described below.

Though the vicinal di(hetero)alkylene organometalate compounds of the invention are sufficient to effect the condensation reaction, certain combinations of reactants and/or product formation may be benefited by treating the one or more metal oxides with a moderator, hereinafter termed "performance moderator." Moderators can be used to control the performance of certain reaction substances in areas of selectivity to certain products and the repression of a particular reaction substance's proclivity to generate a broad range of reaction products. A range of suitable materials may impact the vicinal di(hetero)alkylene organometalates of this invention in the variety of reaction products. The performance moderator may be any material which impacts the vicinal di(hetero)alkylene organometalate's selection of reaction products or which changes the proportion of any one or more of the reaction products which the vicinal di(hetero)alkylene organometalate compound generates at comparable processing conditions. In addition to contributing to product selectivity, the performance moderator may be any material which contributes to reaction activity and/or stability of the support (mechanical or dimensional strength).

An illustrative performance moderator is a mineral acid or a compound derived from a mineral acid Suitable for use as performance moderators are one or more phosphoric acid or a salt of phosphoric acid. hydrogen fluoride, hydrofluoric acid or a fluoride salt, sulfuric acid or a salt of sulfuric acid, and the like. The moderator may also be organic esters of phosphoric acid or a salt of phosphoric acid, hydrogen fluoride organic complexes, hydrofluoric acid organic complexes or a fluoride salt organic complexes, organic esters of sulfuric acid or a salt of sulfuric acid, and the like. Suitable salts of phosphoric acid include sodium dihydrogen phosphate, disodium hydrogen phosphate, sodium phosphate and the like. Other illustrative performance moderators include the metal oxides described above which can be used in preparing the vicinal di(hetero)alkylene organometalates, metallic phosphates which may or may not have a cyclic structure, metallic polyphosphates which may or may not have a condensed structure, Group VIB metal-containing substances and mixtures of the above.

The metal oxides described hereinabove which can be used in preparing the vicinal di(hetero)alkylene organometalate can also be used as performance moderators in accordance with this invention. The metal oxides can contribute to product selectivity, reaction activity and/or stability of the support (mechanical strength).

As indicated above, other performance moderators which can be used in accordance with this invention include metallic phosphates which may or may not have a cyclic structure and metallic polyphosphates which may or may not have a condensed structure. Corresponding metallic metaphosphimates, metallic phosphoramidates and metallic amido and imidophosphates of the above may also be used as performance moderators in accordance with this invention. Such metallic phosphates and polyphosphates can contribute to product selectivity, reaction activity and/or stability of the support (mechanical strength).

The metallic phosphate and polyphosphate performance moderators may or may not have a cyclic structure and may or may not have a condensed structure. Suitable metallic phosphate performance moderators having a cyclic structure or an acyclic structure are disclosed in U.S. patent application Ser. No. 390,706, filed on an even date herewith and incorporated herein by reference. Suitable metallic polyphosphate performance moderators having a condensed structure are disclosed in U.S. patent application Ser. No. 390,709, filed on an even date herewith and incorporated herein by reference. Illustrative of metallic phosphate and polyphosphate performance moderators include, for example, metallic orthophosphates ($PO_4^{-3}$), metallic pyrophosphates ($P_2O_7^{-4}$), metallic polyphosphate (including tripolyphosphates ($P_3O_{10}^{-5}$), tetrapolyphosphates ($P_4O_{13}^{-6}$), pentapolyphosphates ($P_5O_{16}^{-7}$) and higher polyphosphates), metallic metaphosphates (including trimetaphosphates ($P_3O_9^{-3}$), tetrametaphosphates ($P_4O_{12}^{-4}$) and other lower and higher metaphosphates) and metallic ultraphosphates (condensed phosphates containing more $P_2O_5$ than corresponds to the metaphosphate structure). Corresponding metallic metaphosphimates, metallic phosphoramidates and metallic amido- and imidophosphates of the above may also be used as performance moderators in accordance with this invention. Suitable metals which can be incorporated into the metallic phosphate and polyphosphate performance moderators include, for example, Group IA metals, Group IIA metals, Group IIIB metals, Group IVB metals, Group VB metals, Group VIB metals, Group VIIB metals, Group VIII metals, Group IB metals, Group IIB metals, Group IIIA metals, Group IVA metals, Group VA metals, Group VIA metals, and mixtures thereof.

Illustrative of metallic orthophosphate performance moderators which may be utilized in this invention include, for example, $NaH_2PO_4$, $KH_2PO_4$, $RbH_2PO_4$, $LiH_2PO_4$, $MgHPO_4$, $CaHPO_4$, $YPO_4$, $CePO_4$, $LaPO_4$, $ThPO_4$, $MnPO_4$, $FePO_4$, $BPO_4$, $AlPO_4$, $BiPO_4$, $Mg(H_2PO_4)_2$, $Ba(H_2PO_4)_2$, $Mg(NH_4)_2PO_4$, $Ca(H_2PO_4)_2$, $La(H_2PO_4)_3$ and the like. Illustrative of metallic pyrophosphate performance moderators which may be utilized in this invention include, for example, $Na_2H_2P_2O_7$, $K_2H_2P_2O_7$, $Ca_2P_2O_7$, $Mg_2P_2O_7$, $KMnP_2O_7$, $AgMnP_2O_7$, $BaMnP_2O_7$, $NaMnP_2O_7$, $KCrP_2O_7$, $NaCrP_2O_7$, $Na_4P_2O_7$, $K_4P_2O_7$, $Na_3HP_2O_7$, $NaH_3P_2O_7$, $SiP_2O_7$, $ZrP_2O_7$, $Na_6Fe_2(P_2O_7)_3$, $Na_8Fe_4(P_2O_7)_5$, $Na_6Cu(P_2O_7)_2$, $Na_{32}Cu_{14}(P_2O_7)_{15}$, $Na_4Cu_{18}(P_2O_7)_5$, $Na_2(NH_4)_2P_2O_7$, $Ca(NH_4)_2P_2O_7$, $MgH_2P_2O_7$, $Mg(NH_4)_2P_2O_7$ and the like. Illustrative of metallic polyphosphate performance moderators which may be utilized in this invention include, for example, $NaSr_2P_3O_{10}$, $NaCa_2P_3O_{10}$, $NaNi_2P_3O_{10}$, $Na_5P_3O_{10}$, $K_5P_3O_{10}$, $Na_3MgP_3O_{10}$, $Na_3CuP_3O_{10}$, $Cu_5(P_3O_{10})_2$, $Na_3ZnP_3O_{10}$, $Na_3CdP_3O_{10}$, $Na_6Pb(P_3O_{10})_2$, $Na_3CoP_3O_{10}$, $K_3CoP_3O_{10}$, $Na_3NiP_3O_{10}$, $K_2(NH_4)_3P_3O_{10}$, $Ca(NH_4)_2P_3O_{10}$, $La(NH_4)_2P_3O_{10}$, $NaMgH_2P_3O_{10}$ and the like. Illustrative of metallic metaphosphate performance moderators which may be utilized in this invention include, for example, $Na_3P_3O_9$, $K_3P_3O_9$, $Ag_3P_3O_9$, $Na_4P_4O_{12}$, $K_4P_4O_{12}$, $Na_2HP_3O_9$, $Na_4Mg(P_3O_9)_2$, $NaSrP_3O_9$, $NaCaP_3O_9$, $NaBaP_3O_9$, $KBaP_3O_9$, $Ca_3(P_3O_9)_2$, $Ba(P_3O_9)_2$, $Na_2Ni_2(P_3O_9)_2$, $Na_4Ni(P_3O_9)_2$, $Na_4Co(P_3O_9)_2$, $Na_4Cd(P_3O_9)_2$ and the like. Illustrative of metallic ultraphosphate performance moderators which may be utilized in this invention include, for example, $CaP_4O_{11}$, $Ca_2P_6O_{17}$, $Na_8P_{10}O_{29}$, $Na_6P_8O_{23}$, $Na_2CaP_6O_{17}$, $Na_2P_4O_{11}$, $NaBaP_7O_{18}$, $Na_2P_8O_{21}$, $K_4P_6O_{17}$ and the like. The preferred metallic phosphate and polyphosphate performance moderators for use in this invention include Group IA metal metaphosphates, Group IA metal dihydrogen orthophosphates and Group IA metal dihydrogen pyrophosphates, more preferably $Na_3P_3O_9$, $NaH_2PO_4$ and $Na_2H_2P_2O_7$. Other suitable metallic phosphate and polyphosphate performance moderators embraced within the scope of this invention are disclosed by Van Wazer, J. R., Phosphorus and Its Compounds, Vol. 1, Interscience Publishers, Inc., New York (1958).

Group VIB metal containing substances may be used as performance moderators in accordance with this invention. Suitable Group VIB metal containing substances are disclosed in U.S. patent application Ser. No. 390,708, filed on an even date herewith and incorporated herein by reference. Illustrative of Group VIB metal-containing performance moderators include, for example, one or more oxides of tungsten, chromium, molybdenum or mixtures thereof.

A variety of conventional phosphorus-containing substances may be suitable for use as performance moderators in this invention. As indicated above, the conventional substances should be capable of functioning as a performance moderator. Illustrative of conventional phosphorus containing substances may include, for example, those disclosed in U.S. Pat. No. 4,036,881, U.S. Pat. No. 4,806,517, U.S. Pat. No. 4,617,418, U.S. Pat. No. 4,720,588, U.S. Pat. No. 4,394,524, U.S. Pat. No. 4,540,822, U.S. Pat. No. 4,588,842, U.S. Pat. No. 4,605,770, U.S. Pat. No. 4,683,335, U.S. Pat. No. 4,316,841, U.S. Pat. No. 4,463,193, U.S. Pat. No. 4,503,253. U.S. Pat. No. 4,560,798 and U.S. Pat. No. 4,578,517.

Suitable conventional phosphorus containing substances which may be employed as performance moderators in this invention include acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

The amount of the performance moderator of the mineral acid type used with the one or more metal oxides is not narrowly critical. Generally, the amount does not exceed 25 weight percent of the weight of the one or more metal oxides. As a rule, it is desirable to use at least 0.01 weight percent of the weight of the one or more metal oxides. Preferably, the amount of performance moderator, when used, will range from about 0.2 to about 10 weight percent of the weight of the one or more metal oxides. Most preferably, the amount of performance moderator, when used, will range from about 0.5 to about 5 weight percent of the weight of the one or more metal oxides.

The amount of performance moderator other than the mineral acid type used with the one or more metal oxides is not narrowly critical. Generally, the amount does not exceed 90 weight percent of the weight of the one or more metal oxides. The amount of performance moderator can range from about 0 to about 90 or greater weight percent of the weight of the one or more metal oxides, preferably from about 0 to about 75 weight percent of the weight of the one or more metal oxides, and more preferably from about 0 to about 50 weight percent of the weight of the one or more metal oxides. Most preferably, the amount of performance moderator, when used, will range from about 0.5 to about 25 weight percent of the weight of the one or more metal oxides.

The performance moderator can be provided to the one or more metal oxides by conventional procedures known in the art. For example, the performance moderator can be provided to the one or more metal oxides by impregnating particles or monolithic structures comprising the one or more metal oxides with liquid comprising the performance moderator. This is a well known procedure in the art for incorporating additives to a solid support material. The one or more metal oxides may be utilized as solid powders or as fused, bonded or compressed solid pellets, or larger structures in association with the one or more other metal oxides, or as coated, fused, bonded or compressed solid pellets, or larger structures, composited with one or more support materials, in association with one or more other metal oxides. These solid structures may be treated with the performance moderator by mixing a liquid body of the performance moderator with the solid structure. For example, the one or more metal oxide solids may be slurried in the performance moderator, drained, washed and suctioned to remove excess performance moderator, and then dried with heat to remove any volatiles accompanying the performance moderator. The drying temperature chosen will depend on the nature of the volatiles to be removed. Usually, the time/temperature for effecting drying will be below the conditions for effecting dehydration to remove bound water from the one or more metal oxides. Normally the drying temperature will be greater than about 120° C. and below about 600° C. depending on the thermal stability of the one or more metal oxides. The drying time will generally go down as the drying temperature rises and vice versus, and may extend from 5 seconds to about 24 hours.

Alternatively, the one or more metal oxides may be condensed from their respective hydrolyzable monomers to the desired oxides to form oxide powders which can thereafter be blended and compressed with the performance moderator to form pellets and larger structures. The one or more metal oxides can be provided from metal salts which can be heated to form the metal oxide. It is appreciated that the performance moderator can be incorporated into the molecular bonding configuration of the one or more meta oxides by conventional procedures known in the art.

The one or more metal oxides prior to the optional treatment of the performance moderator may be prepared in a wide variety of ways. For example, one or more metal oxides may be provided as a partial condensate on a support, such as a silica or alpha, beta or gamma alumina, silicon carbide, and the like, and then condensed by heating to effect polymerization to the desired oxide form. The metal oxide(s) may be condensed from hydrolyzable monomers to the desired oxide, indeed, to form an oxide powder which can thereafter be compressed to form pellets and larger structures of the metal oxide(s). The powder can be made into a shapeable paste which can be extruded and cut into pellets according to conventional procedures. The extrudate may thereafter be fired to cure the metal oxide(s) and fix the structure. The cut extrudate may be blended with a support material such as those characterized above, and the blend fired to fuse the metal oxide(s) to the support.

In a preferred embodiment of this invention, a high surface area silica or titania can be slurried with an aqueous solution of ammonium metatungstate, extruded, and calcined at a temperature of about 400° C.

A preferred structure comprises one or more oxides of a Group VIB metal in association with a Group IVA or IVB metal oxide having a surface area of at least a 140 m$^2$/gm which may or may not be bonded to a support material. The term "support," as used herein and in the claims, means a solid structure which does not adversely affect the properties of the vicinal di(hetero)alkylene organometalate and is at least as stable as the one or more metal oxides to the reaction medium. The support may act in concert with the one or more metal oxides to moderate the reaction. Some supports may contribute to the selectivity of the reaction. The structure can comprise from about 2 to about 60 percent by weight or greater of the support, more preferably from about 10 to about 50 percent by weight of the support, the remainder being the weight of the metal oxide(s). Included in the weight of the support is the weight of any binding agent such as phosphates, sulfates, silicates, fluorides, and the like, and any other additive provided to stabilize or otherwise help in the manufacture of the vicinal di(hetero)alkylene organometalate. The support may be particles as large or larger than the metal oxide component and "glued" to the metal oxide by virtue of a binding medium.

The support may constitute a separate phase in the process of extruding the structure. In this embodiment, the support forming material, preferably as a paste is blended with a paste of the one or more metal oxides or a partial condensate thereof. The paste may comprise the oxide forms of the support, which is blended with water and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the metal oxide(s).

The use of supports for the one or more metal oxides provide a number of significant advantages. It has been determined that some of the metal oxides are not as stable in the amines reaction media when utilized over an extended period of time. When the reaction is effected as a batch reaction, this matter is not a problem. However, when the reaction is effected with the one or more metal oxides as part of a fixed bed in a tubular reactor, the preferred procedure for carrying out the invention, it is desirable to have the metal oxide(s) be more stable. When the metal oxide(s) is combined with the support, the metal oxide(s) has greater stability for the reaction medium, and therefore, it is better able to be used in a fixed bed of a continuous reactor. The supported metal oxide(s) suffer from none of the leaching problems that the metal oxides per se may have or the problems that are associated with the prior art substances, such as acidic phosphorus compounds on silica.

The reactants used in the condensation process of the invention may be ammonia or organic compound containing —NH— and any compound possessing an alcoholic hydroxyl group, subject to the following: the intramolecular condensation of an amino compound produces an amine having a lower molecular weight, and the intermolecular condensation of an amino compound with one or more of another amino compound or a compound containing an alcoholic hydroxyl group produces an amine having a lower, same or higher molecular weight than the reactants.

The one or more metal oxides are preferably contacted in situ with one or more alkanolamines, alkyleneamines, alkylene glycols or mixtures thereof to form the vicinal di(hetero)alkylene organometalates of this invention. As indicated above, an oxyacid having a divalent or polyvalent anion or a divalent or polyvalent metal salt of an oxyacid or mixtures thereof may be introduced as impregnates to improve the performance of the one or more metal oxides. These polyoxyanions can alter the electronic properties of the one or more metal oxides and thus effectuate the formation of vicinal di(hetero)alkylene organometalates. The vicinal di(hetero)alkylene organometalates should be amenable to displacement by a suitable nucleophile such as alkyleneamine or alkanolamine in order to form the desired amine products. Illustrative of suitable reactants in effecting the process of the invention, include by way of example:

Ammonia
MEA - monoethanolamine
EDA - ethylenediamine
MeEDA - methylethylenediamine
EtEDA - ethylethylenediamine
AEEA - N-(2-aminoethyl)ethanolamine
HEP - N-(2 hydroxyethyl)piperazine
DETA - diethylenetriamine
AEP - N-(2 aminoethyl)piperazine
TAEA - trisaminoethylamine
TETA - triethylenetetramine
TEPA - tetraethylenepentamine
PEHA - pentaethylenehexamine
  TETA Isomers:
TAEA - trisaminoethylamine
TETA - triethylenetetramine
DPE - dipiperazinoethane
DAEP - diaminoethylpiperazine
PEEDA - piperazinoethylethylenediamine
  TEPA Isomers:
AETAEA - aminoethyltrisaminoethylamine
TEPA - tetraethylenepentamine
AEDPE - aminoethyldipiperazinoethane
AEPEEDA - aminoethylpiperazinoethylethylenediamine
iAEPEEDA - isoaminoethylpiperazinoethylethylenediamine
AEDAEP - aminoethyldiaminoethylpiperazine
BPEA - bispiperazinoethylamine The foregoing also can represent the products of the reaction. For example, MEA and DETA are frequently employed to produce TETA along with a variety of other amines, most of which are set forth above.

Glycol compounds can also be employed in the preparation of vicinal di(hetero)alkylene organometalates of this invention. For purposes of this invention, glycol compounds embrace diols and polyols. Illustrative of suitable glycol compounds include alkylene glycols such as ethylene glycol, propylene glycol, 1,3-propane diol or mixtures thereof.

The process may be effected in the liquid or vapor or supercritical liquid states or mixtures thereof though the actual reaction is believed to occur on the metal oxide's solid surface in the absorbed state. In this context, the vapor phase reaction is intended to refer to the general vapor state of the reactants. Though the reaction conditions may range from subatmospheric to superatmospheric conditions, it is desirable to run the reaction from about 50 psig to about 3,000 psig, preferably from about 200 psig to about 2,000 psig.

The temperature of the reaction may be as low as about 125° C. to about 400° C. Preferably, the reaction temperature ranges from about 150° C. to about 350° C., and most preferably from about 225° C. to about 325° C.

The reaction may be effected by the incremental addition of one of the reactants to the other or by the joint addition of the reactants to the one or more metal oxides. The preferred process effects the reaction in a continuous manner over a fixed bed of one or more metal oxides in a tubular reactor. However, the reaction may be carried out by slurrying one or more metal oxides in the reactants or in a batch mode in an autoclave. An inert such as nitrogen, methane or the like can be used in the reaction process.

The preferred process involves the formation of alkyleneamines from the intermolecular condensation of alkanolamines and alkyleneamines or the intramolecular condensation of alkyleneamines or alkanolamines. Illustrative of such reactions are the following reactant combinations:

| REACTANT | REACTANT | PRODUCTS |
| --- | --- | --- |
| Ammonia | Methanol | Monomethylamine |
|  |  | Dimethylamine |
|  |  | Trimethylamine |

-continued

| REACTANT | REACTANT | PRODUCTS |
| --- | --- | --- |
| Ammonia | MEA | EDA, DETA, AEEA, TETA, TEPA, PIP |
| Ammonia | AEEA | DETA, PIP |
| MEA, Ammonia | EDA | EDA, AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| MEA | EDA | AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| EDA | AEEA | HEP, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| DETA | AEEA | TEPA Isomers, AEP |
| EDA | EDA | DETA, TETA AND TEPA Isomers |

While not wishing to be bound to any particular reaction mechanism, it is believed that the mechanistic pathway for making TETA by the condensation of MEA and DETA in the presence of tungsten oxide or a suitable tungsten salt occurs as follows:

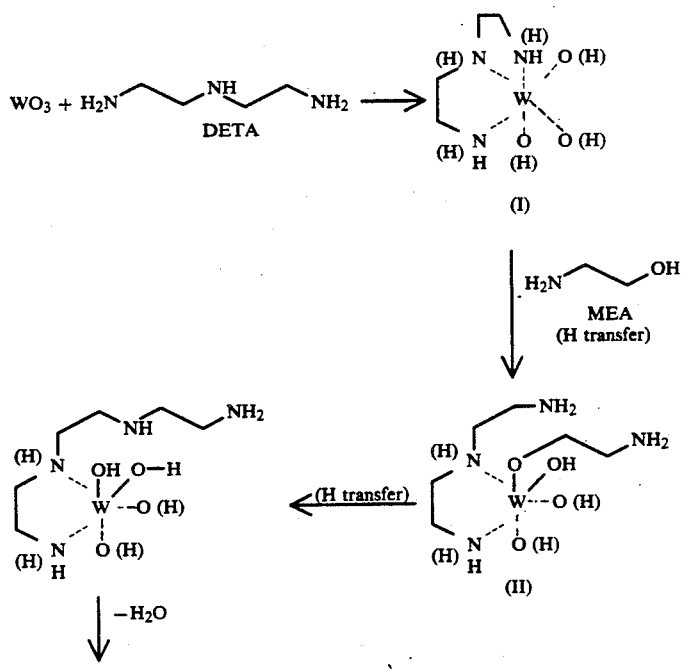

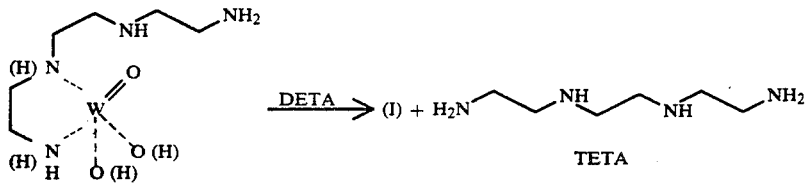

Also, while not wishing to be bound to any particular reaction mechanism it is believed that the mechanistic pathway for making TETA by the condensation of AEEA and EDA in the presence of tungsten oxide or a suitable tungsten salt occurs as follows:

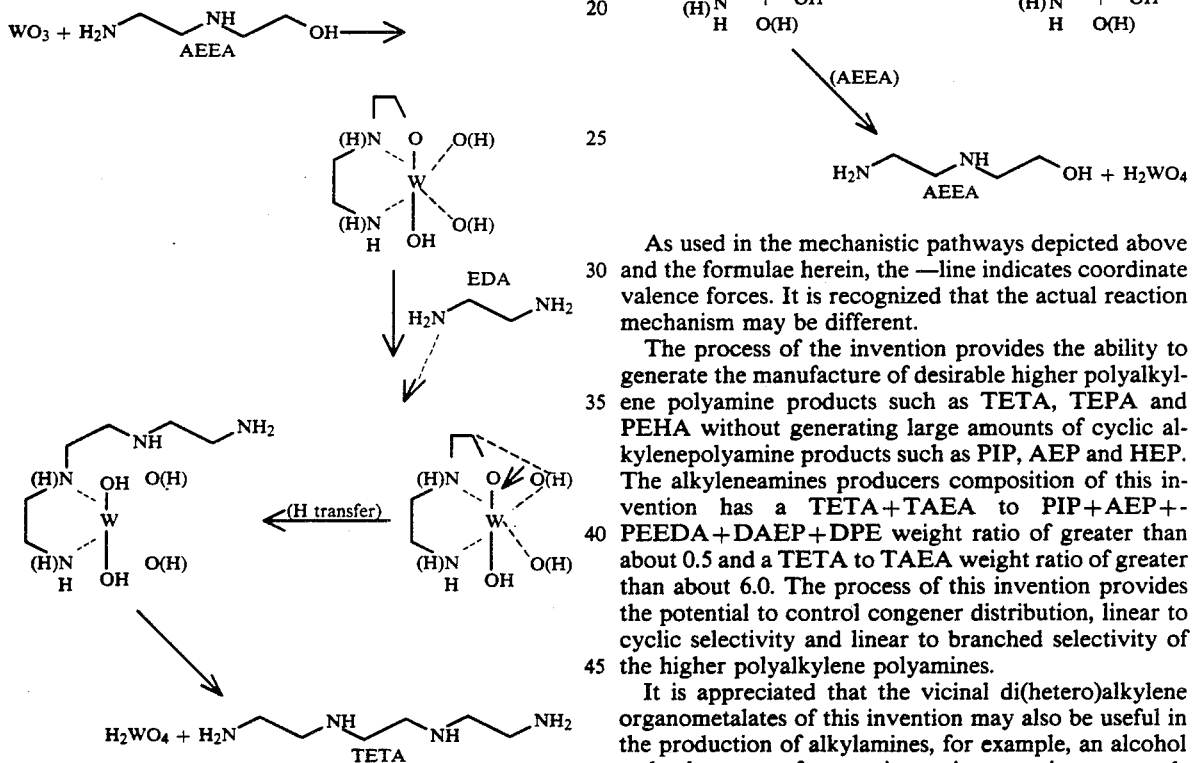

Further, while not wishing to be bound to any particular reaction mechanism, it is believed that the mechanistic pathway for making AEEA by the condensation of MEA in the presence of tungsten oxide or a suitable tungsten salt occurs as follows:

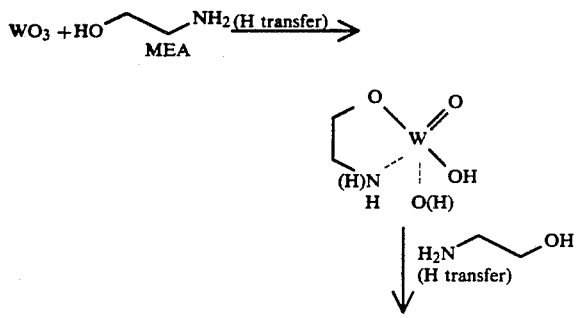

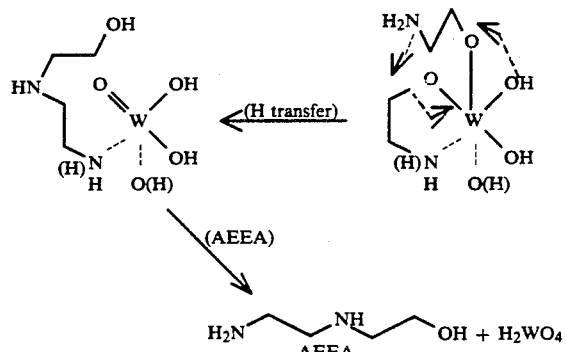

As used in the mechanistic pathways depicted above and the formulae herein, the —line indicates coordinate valence forces. It is recognized that the actual reaction mechanism may be different.

The process of the invention provides the ability to generate the manufacture of desirable higher polyalkylene polyamine products such as TETA, TEPA and PEHA without generating large amounts of cyclic alkylenepolyamine products such as PIP, AEP and HEP. The alkyleneamines producers composition of this invention has a TETA+TAEA to PIP+AEP+PEEDA+DAEP+DPE weight ratio of greater than about 0.5 and a TETA to TAEA weight ratio of greater than about 6.0. The process of this invention provides the potential to control congener distribution, linear to cyclic selectivity and linear to branched selectivity of the higher polyalkylene polyamines.

It is appreciated that the vicinal di(hetero)alkylene organometalates of this invention may also be useful in the production of alkylamines, for example, an alcohol and at least one of ammonia, a primary amine, a secondary amine or a tertiary amine may be contacted in the presence of one or more metal oxides to provide vicinal di(hetero)alkylene organometalates which can be utilized under conditions effective to produce alkylamines This invention is further illustrated by certain of the following examples:

EXAMPLES

In the examples set forth in the tables below, the metal oxide(s) of choice were placed in a tubular reactor having an outside diameter of 1 inch and an overall length of 30 inches. The metal oxide portion of the reactor comprised a length of 24 inches, accommodating 150 cubic centimeters of metal oxide. The reactor was made of 316 stainless steel. As used in the tables below, acyclic (N4)/cyclic (<=N4) refers to the weight ratio of TETA+TAEA to PIP+AEP+PEEDA+DAEP+DPE. The one or more metal oxides employed are identified as follows:

| Designation | Composition | Physical Properties |
|---|---|---|
| A | $TiO_2$ (anatase)/$(NH_4)_6H_6W_{12}O_{40}$ (15 wt. % W). | Particle size: 1/16 inch cylindrical extrudates; $TiO_2$ surface area: 200 $m^2$/gm. |
| B | $TiO_2$ (anatase)/$SiO_2$/$(NH_4)_6H_6W_{12}O_{40}$ (15 wt. % W); $TiO_2$/$SiO_2$ wt. ratio = 88/12. | Particle size: 1/16 inch cylindrical extrudates; $TiO_2$—$SiO_2$ surface area: 175 $m^2$/gm. |
| C | $ZrO_2$/$SiO_2$/$(NH_4)_6H_6W_{12}O_{40}$ (15 wt. % W). | Particle size: 1/16 inch cylindrical extrudates; $ZrO_2$—$SiO_2$ surface area: 127 $m^2$/gm. |
| D | $TiO_2$ (anatase)/$SiO_2$/$(NH_4)_6H_6W_{12}O_{40}$ (7.5 wt. % W); $TiO_2$/$SiO_2$ wt. ratio = 88/12. | Particle size: 1/16 inch cylindrical extrudates; $TiO_2$—$SiO_2$ surface area: 175 $m^2$/gm. |
| E | $TiO_2$ (anatase)/$SiO_2$/$(NH_4)_6H_6W_{12}O_{40}$ (15 wt. % W)/$La_2O_3$ (1 wt. % La): $TiO_2$/$SiO_2$ wt. ratio = 88/12. | Particle size: 1/16 inch cylindrical extrudates; $TiO_2$—$SiO_2$ surface area: 175 $m^2$/gm. |
| F | $TiO_2$ (anatase)/$SiO_2$/$(NH_4)_6H_6W_{12}O_{40}$ (7.5 wt. % W)/$La_2O_3$ (0.5 wt. % La): $TiO_2$/$SiO_2$ wt. ratio = 88/12. | Particle size: 1/16 inch cylindrical extrudates; $TiO_2$—$SiO_2$ surface area: 175 $m^2$/gm. |
| G | $ZrO_2$/$SiO_2$/$(NH_4)_6H_6W_{12}O_{40}$ (15 wt. % W)/$La_2O_3$ (1.0 wt. % La). | Particle size: 1/16 inch cylindrical extrudates; $ZrO_2$—$SiO_2$ surface area: 127 $m^2$/gm. |
| H | $TiO_2$ (anatase)/$SiO_2$/$WO_3$ (3.0 wt. % $WO_3$). | Particle size: 1/16 inch cylindrical extrudates; $TiO_2$—$SiO_2$—$WO_3$ surface area: 234 $m^2$/gm. |
| I | $TiO_2$ (anatase)/$SiO_2$/$WO_3$/$(NH_4)_6H_6W_{12}O_{40}$ (7.5 wt. % W) | Particle size: 1/16 inch cylindrical extrudates; $TiO_2$—$SiO_2$—$WO_3$ surface area: 234 $m^2$/gm. |
| J | $TiO_2$ (anatase)/$SiO_2$/$SiO_2 \cdot 12 WO_3 \cdot 26 H_2O$ (7.5 wt. % W). | Particle size: 1/16 inch cylindrical extrudates; $TiO_2$—$SiO_2$ surface area: 175 $m^2$/gm. |
| K | $TiO_2$ (anatase)/$SiO_2$/$Al_2O_3$/$(NH_4)_6H_6W_{12}O_{40}$ (7.5 wt. % W). | Particle size: 1/16 inch cylindrical extrudates; $TiO_2$—$SiO_2$—$Al_2O_3$ surface area: 175 $m^2$/gm. |
| L | $TiO_2$ (anatase)/$Al_2O_3$/$SiO_2$/$(NH_4)_6H_6W_{12}O_{40}$ (7.5 wt. % W). | Particle size: 1/16 inch cylindrical extrudates: $TiO_2$—$Al_2O_3$—$SiO_2$ surface area: 175 $m^2$/gm. |
| M | $TiO_2$ (anatase)/$SiO_2$/$(NH_4)_6H_6W_{12}O_{40}$ (7.5 wt. % W); $TiO_2$/$SiO_2$ wt. ratio = 70/30. | Particle size: 1/16 inch cylindrical extrudates; $TiO_2$—$SiO_2$ surface area: 195 $m^2$/gm. |
| N | $TiO_2$ (anatase). | Particle size: 1/16 inch cylindrical extrudates; $TiO_2$ surface area: 200 $m^2$/gm. |
| O | $TiO_2$ (anatase)/$SiO_2$; $TiO_2$/$SiO_2$ wt. ratio = 70/30. | Particle size: 1/16 inch cylindrical extrudates; $TiO_2$—$SiO_2$ surface area: 195 $m^2$/gm. |
| P | $TiO_2$ (anatase)/$SiO_2$; $TiO_2$/$SiO_2$ wt. ratio = 88/12. | Particle size: 1/16 inch cylindrical extrudates; $TiO_2$—$SiO_2$ surface area: 175 $m^2$/gm. |
| Q | $ZrO_2$/$SiO_2$. | $SiO_2$ surface area: 175 $m^2$/gm. Particle size: 1/16 inch cylindrical extrudates; $ZrO_2$—$SiO_2$ surface area: 127 $m^2$/gm. |
| R | $\gamma$-$Al_2O_3$/$(NH_4)_6H_6W_{12}O_{40}$ (7.5 wt % W). | Particle size: 1/16 inch cylindrical extrudates; $\gamma$-$Al_2O_3$ surface area: 105 $m^2$/gm. |
| S | $TiO_2$ (anatase)/$SiO_2$/$(NH_4)_6H_6W_{12}O_{40}$ (7.5 wt. % W); $TiO_2$/$SiO_2$ wt. ratio = 70/30. | Particle size: 1/16 inch cylindrical extrudates; $TiO_2$—$SiO_2$ surface area: 195 $m^2$/gm. |
| T | $TiO_2$ (anatase)/$SiO_2$/$WO_3$ (7 wt. % $WO_3$). | Particle size: 1/16 inch cylindrical extrudates; $TiO_2$—$SiO_2$—$WO_3$ surface area: 224 $m^2$/gm. |
| U | $TiO_2$ (anatase)/$SiO_2$/$(NH_4)_6H_6W_{12}O_{40}$ (7.5 wt. % W)/$B_2O_3$ (1.0 wt. % B). | Particle size: 1/16 inch cylindrical extrudates; $TiO_2$—$SiO_2$ surface area: 195 $m^2$/gm. |
| V | $TiO_2$ (anatase)/$SiO_2$/$(NH_4)_6H_6W_{12}O_{40}$ (7.5 wt. % W)/$ZnO$ (1.0 wt. % Zn); $TiO_2$/$SiO_2$ wt. ratio = 70/30. | Particle size: 1/16 inch cylindrical extrudates; $TiO_2$—$SiO_2$ surface area: 195 $m^2$/gm. |
| W | $TiO_2$ (anatase)/$SiO_2$/$(NH_4)_6H_6W_{12}O_{40}$ (7.5 wt. % W)/$ThO_2$ (1.0 wt. % Th); $TiO_2$/$SiO_2$ wt. ratio = 70/30. | Particle size: 1/16 inch cylindrical extrudates; $TiO_2$—$SiO_2$ surface area: 195 $m^2$/gm. |
| X | $TiO_2$ (anatase)/$SiO_2$/$(NH_4)_6H_6W_{12}O_{40}$ (7.5 wt. % W)/$NH_4F$—HF (1.0 wt. % F); $TiO_2$/$SiO_2$ wt. ratio = 70/30. | Particle size: 1/16 inch cylindrical extrudates; $TiO_2$—$SiO_2$ surface area: 195 $m^2$/gm. |
| Y | $TiO_2$ (anatase)/$SiO_2$/$(NH_4)_6H_6W_{12}O_{40}$ (7.5 wt. % W)/$CeO_2$ (1.0 wt. % Ce); $TiO_2$/$SiO_2$ wt. ratio = 70/30. | Particle size: 1/16 inch cylindrical extrudates; $TiO_2$—$SiO_2$ surface area: 195 $m^2$/gm. |
| Z | $TiO_2$ (anatase/$WO_3$ (10 wt. % $WO_3$). | Particle size: 1/16 inch cylindrical extrudates; $TiO_2$—$WO_3$ surface area: 253 $m^2$/gm. |
| AA | $SiO_2$/$WO_3$ (10 wt. % $WO_3$). | Particle size: 1/16 inch cylindrical extrudates; $SiO_2$—$WO_3$ surface area: 144 $m^2$/gm. |
| BB | $TiO_2$ (anatase)/$SiO_2$; $TiO_2$/$SiO_2$ wt. ratio = 40/60 | Particle size: 1/16 inch cylindrical extrudates; $TiO_2$—$SiO_2$ surface area: 201 $m^2$/gm. |

For each run the tubular reaction system was brought up to the designated conditions. The ammonia feed was established first, then the DETA-MEA feed. After a sufficient line out period, a two hour timed run was conducted, then the experiment was run overnight and sampled. The temperature was changed and the above procedure repeated.

The metal oxide-containing compositions employed in the examples hereinafter were prepared as follows:

Composition A Preparation: Ammonium metatungstate (12.14 grams) was dissolved in water (60 grams) and an aliquot sufficient to wet the $TiO_2$ support (140 grams) was used. After wetting, the composition was calcined at a temperature of 350° C. for a period of 1 hour. The impregnation and calcination steps were repeated twice more to give the composition.

Composition B Preparation: Ammonium metatungstate (12.14 grams) was dissolved in water (48 grams) and an aliguot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition C Preparation: Ammonium metatungstate (12.14 grams) was dissolved in water (48 grams) and an aliguot sufficient to wet the $ZrO_2/SiO_2$ support (55 grams) was used. After wetting, the composition was calcined at a temperature of 350° C. for a period of 1 hour. The impregnation and calcination steps were repeated twice more to give the composition.

Composition D Preparation: Ammonium metatungstate (6.07 grams) was dissolved in water (45 grams) and an aliguot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition E Preparation: Ammonium metatungstate (12.14 grams) and lanthanum nitrate (5.0 grams) were dissolved in water (45 grams) and an aliquot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition F Preparation: Ammonium metatungstate (6.07 grams) and lanthanum nitrate (2.5 grams) were dissolved in water (45 grams) and an aliquot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition G Preparation: Ammonium metatungstate (12.14 grams) and lanthanum nitrate (5.0 grams) were dissolved in water (45 grams) and an aliquot sufficient to wet the $ZrO_2/SiO_2$ support (55 grams) was used. After wetting, the composition was calcined at a temperature of 350° C for a period of 1 hour. The impregnation and calcination steps were repeated twice more to give the composition.

Composition H Preparation: Obtained from Norton Company, Akron, Ohio.

Composition I Preparation: Ammonium metatungstate (6.07 grams) was dissolved in water (35 grams) and an aliguot sufficient to wet the $TiO_2/SiO_2/WO_3$ support (55 grams) was used. After wetting, the composition was calcined at a temperature of 350° C. for a period of 1 hour. The impregnation and calcination steps were repeated twice more to give the composition.

Composition J Preparation: Silicotungstic acid (6.8 grams) was dissolved in water (40 grams) and an aliquot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition K Preparation: Ammonium metatungstate (6.07 grams) was dissolved in water (40 grams) and an aliguot sufficient to wet the $TiO_2/SiO_2/Al_2O_3$ support (55 grams) was used. After wetting, the composition was calcined at a temperature of 350° C. for a period of 1 hour The impregnation and calcination steps were repeated twice more to give the composition.

Composition L Preparation: Ammonium metatungstate (6.07 grams) was dissolved in water (40 grams) and an aliguot sufficient to wet the $TiO_2/Al_2O_3/SiO_2$ support was used. After wetting, the composition was calcined at a temperature of 350° C. for a period of 1 hour. The impregnation and calcination steps were repeated twice more to give the composition.

Composition M Preparation: Ammonium metatungstate (6.07 grams) was dissolved in water (40 grams) and an aliguot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition N Preparation: Obtained from LaRoche Chemical Company, Cleveland, Ohio.

Composition O Preparation: Obtained from Norton Company, Akron, Ohio.

Composition P Preparation: Obtained from Norton Company, Akron, Ohio.

Composition Q Preparation: Obtained from Norton Company, Akron, Ohio.

Composition R Preparation: Ammonium metatungsrate (11.42 grams) was dissolved in water (45 grams) and an aliguot sufficient to wet the $\gamma\text{-}Al_2O_3$ support (52 grams) was used. After wetting. The composition was calcined at a temperature of 350° C. for a period of 1 hour The impregnation and calcination steps were repeated twice more to give the composition Composition S Preparation: Ammonium metatungstate (6.07 grams) was dissolved in water (40 grams) and an aliguot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition T Preparation: Obtained from Norton Company, Akron, Ohio.

Composition U Preparation: Ammonium metatungstate (6.07 grams) and boric acid (3.14 grams) were dissolved in water (30 grams) and an aliquot sufficient to wet the $TiO_2/SiO_2$ support (55 grams) was used. After wetting, the composition was calcined at a temperature of 350° C. for a period of 1 hour. The impregnation and calcination steps were repeated twice more to give the composition.

Composition V Preparation: Ammonium metatungstate (6.07 grams) and zinc nitrate (1 6 grams) were dissolved in water (30 grams) and an aliquot sufficient to wet the $TiO_2/SiO_2$ support (55 grams) was used. After wetting, the composition was calcined ar a temperature of 350° C. for a period of 1 hour. The impregnation and calcination steps were repeated twice more to give the composition.

Composition W Preparation: Ammonium metatungstate (6.07 grams) and thorium nitrate (1 31 grams) were dissolved in water (35 grams) and an aliquot sufficient to where the $TiO_2/SiO_2$ support (55 grams) was used. After wetting, the composition was calcined at a temperature cf 350° C. for a period of 1 hour. The impregnation and calcination steps were repeated twice more to give the composition.

Composition X Preparation: Ammonium metatungstate (6.07 grams) and ammonium bifluoride (0.82 grams) were dissolved in water (35 grams) and an aliquot sufficient to wet the TiO$_2$/SiO$_2$ support (55 grams) was used After wetting, the composition was calcined at a temperature of 350° C. for a period of 1 hour. The impregnation and calcination steps were repeated twice more to give the composition.

Composition Y Preparation: Ammonium metatungstate (6.07 grams) and cerium nitrate (1 71 grams) were dissolved in water (35 grams) and an aliguot sufficient to wet the TiO$_2$/SiO$_2$ support (55 grams) was used. After wetting, the composition was calcined ar a temperature of 350° C. for a period of 1 hour. The impregnation and calcination steps were repeated twice more to give the composition.

Composition Z Preparation: Obtained from Norton Company, Akron, Ohio.

Composition AA Preparation: Obtained from Norton Company, Akron, Ohio

Composition BB Preparation: Obtained from Norton Company, Akron, Ohio.

TABLE I

| | Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| Composition Type | A | A | A | A | A | A | A | A | A | A | A |
| Composition weight, gm | 89.3 | 89.3 | 89.3 | 89.3 | 89.3 | 89.3 | 89.3 | 89.3 | 89.3 | 89.3 | 89.3 |
| Pressure, psig | 600 | 600 | 600 | 600 | 600 | 600 | 600 | 600 | 600 | 600 | 600 |
| Temperature, °C. | 270.4 | 271 | 280.8 | 260.7 | 270.6 | 260 | 280 | 251.2 | 260.9 | 246 | 256 |
| Time on organics, hrs. | 6 | 25 | 30 | 49 | 54 | 75 | 98 | 122 | 126 | 146 | 150 |
| Duration of run, hrs. | 2 | 2 | 2 | 2 | 2 | 2 | 2 | 2 | 2 | 2 | 2 |
| MEA SV, gmol/hr/kgcat | 2.58 | 3.38 | 3.44 | 3.51 | 3.60 | 3.57 | 3.24 | 3.36 | 3.38 | 3.39 | 3.40 |
| DETA/MEA mole ratio | 0.99 | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 7.581 | 5.561 | 8.937 | 2.704 | 3.955 | 2.560 | 6.744 | 1.365 | 2.123 | 1.102 | 1.555 |
| MEA | 5.649 | 4.652 | 1.477 | 12.445 | 6.771 | 14.307 | 1.922 | 20.539 | 13.637 | 23.785 | 17.583 |
| PIP | 2.611 | 2.188 | 3.634 | 1.038 | 1.673 | 1.040 | 2.760 | 0.505 | 0.844 | 0.316 | 0.605 |
| DETA | 20.830 | 22.594 | 17.418 | 33.381 | 27.328 | 37.933 | 21.040 | 44.901 | 35.026 | 47.146 | 40.284 |
| AEEA | 0.277 | 0.720 | 0.119 | 1.862 | 1.082 | 2.151 | 0.214 | 2.495 | 2.047 | 2.268 | 2.300 |
| AEP | 4.086 | 3.847 | 6.035 | 1.539 | 2.846 | 1.511 | 4.978 | 0.671 | 1.240 | 0.438 | 0.841 |
| HEP | 0.000 | 0.000 | 0.000 | 0.000 | 0.000 | 0.000 | 0.000 | 0.000 | 0.000 | 0.000 | 0.000 |
| TAEA | 0.417 | 1.005 | 0.410 | 1.722 | 1.235 | 1.843 | 0.687 | 1.801 | 1.866 | 1.600 | 1.913 |
| l-TETA | 6.468 | 10.968 | 6.099 | 13.376 | 11.500 | 13.551 | 8.038 | 12.034 | 13.031 | 10.358 | 13.283 |
| DAEP | 0.214 | 2.647 | 3.666 | 0.817 | 1.651 | 0.668 | 3.053 | 0.199 | 0.603 | 0.134 | 0.303 |
| PEEDA | 1.910 | 2.007 | 3.593 | 0.689 | 1.305 | 0.551 | 2.822 | 0.149 | 0.453 | 0.084 | 0.234 |
| DPE | 0.511 | 0.786 | 0.396 | 0.496 | 0.519 | 0.388 | 0.407 | 0.158 | 0.444 | 0.132 | 0.278 |
| AE-TAEA | 1.200 | 2.252 | 1.072 | 2.980 | 2.621 | 3.187 | 1.564 | 2.189 | 3.092 | 1.688 | 2.780 |
| l-TEPA | 4.021 | 8.850 | 3.847 | 8.247 | 8.806 | 7.806 | 6.952 | 4.035 | 7.515 | 3.427 | 5.980 |
| AE-DAEP | 2.544 | 2.479 | 3.363 | 0.847 | 1.622 | 0.596 | 2.586 | 0.217 | 0.561 | 0.186 | 0.310 |
| AE-PEEDA | 1.209 | 1.148 | 1.857 | 0.301 | 0.275 | 0.127 | 0.657 | 0.082 | 0.144 | 0.229 | 0.085 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.400 | 0.546 | 0.786 | 0.214 | 0.327 | 0.203 | 0.511 | 0.072 | 0.356 | 0.213 | 0.271 |
| BPEA | 0.426 | 0.441 | 0.406 | 0.579 | 0.417 | 0.504 | 0.538 | 0.049 | 0.256 | 0.087 | 0.212 |
| Others | 28.967 | 19.631 | 26.356 | 9.863 | 15.860 | 3.864 | 21.819 | 3.947 | 10.343 | 2.978 | 6.374 |
| MEA Conversion, % | 84.58 | 87.85 | 96.06 | 66.71 | 81.58 | 61.26 | 94.72 | 44.71 | 63.52 | 35.97 | 53.12 |
| DETA Conversion, % | 68.31 | 65.04 | 72.53 | 47.07 | 55.94 | 39.12 | 65.80 | 28.35 | 44.46 | 24.76 | 36.33 |
| Acyclic(N4), % | 72.31 | 68.75 | 48.28 | 88.28 | 78.55 | 90.54 | 58.13 | 96.46 | 90.84 | 97.14 | 94.89 |
| Acyclic(N5), % | 53.27 | 70.63 | 43.41 | 85.24 | 81.21 | 88.47 | 66.48 | 93.63 | 88.94 | 87.72 | 90.87 |
| Σ(N5)/Σ(N4), weight ratio | 1.02 | 0.90 | 0.80 | 0.77 | 0.86 | 0.73 | 0.85 | 0.46 | 0.72 | 0.47 | 0.60 |
| Acyclic(N4)/cyclic (< = N4), weight ratio | 0.73 | 1.04 | 0.37 | 3.29 | 1.59 | 3.70 | 0.62 | 8.20 | 4.15 | 10.80 | 6.71 |

TABLE II

| | Example No. | | | | | | | |
|---|---|---|---|---|---|---|---|---|
| | 12 | 13 | 14 | 15 | 16 | 17 | 18 | 19 |
| Composition Type | B | B | B | B | B | B | B | B |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 249.9 | 259.9 | 270 | 265 | 275 | 280.7 | 245.4 | 255.6 |
| Time on organics, hrs. | 23 | 27 | 48 | 53 | 71 | 96 | 119 | 143 |
| Duration of run, hrs. | 2 | 2 | 2 | 2 | 2 | 2 | 2 | 2 |
| MEA SV, gmol/hr/kgcat | 3.68 | 3.83 | 3.55 | 3.76 | 3.33 | 3.79 | 3.95 | 3.85 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.576 | 2.613 | 3.978 | 3.156 | 5.524 | 6.509 | 0.996 | 1.499 |
| MEA | 17.638 | 11.313 | 5.763 | 9.706 | 3.516 | 3.037 | 24.706 | 19.664 |
| PIP | 0.661 | 1.130 | 1.710 | 1.360 | 2.341 | 2.601 | 0.354 | 0.600 |
| DETA | 39.776 | 31.481 | 24.483 | 30.274 | 23.630 | 21.989 | 47.915 | 42.143 |
| AEEA | 2.240 | 1.704 | 1.039 | 1.469 | 0.510 | 0.312 | 1.910 | 2.051 |
| AEP | 0.977 | 1.950 | 3.062 | 2.204 | 4.152 | 4.514 | 0.487 | 0.818 |
| HEP | 0.000 | 0.000 | 0.000 | 0.000 | 0.000 | 0.000 | 0.000 | 0.000 |
| TAEA | 1.670 | 1.413 | 1.130 | 1.389 | 0.831 | 0.617 | 1.418 | 1.634 |
| l-TETA | 13.251 | 13.353 | 12.483 | 13.317 | 11.047 | 9.109 | 9.280 | 11.618 |
| DAEP | 0.478 | 1.311 | 2.314 | 1.454 | 2.807 | 3.039 | 0.151 | 0.330 |
| PEEDA | 0.351 | 0.887 | 1.565 | 0.988 | 2.444 | 2.697 | 0.112 | 0.237 |
| DPE | 0.312 | 0.494 | 0.685 | 0.566 | 0.162 | 0.218 | 0.143 | 0.272 |

TABLE II-continued

| | Example No. | | | | | | | |
|---|---|---|---|---|---|---|---|---|
| | 12 | 13 | 14 | 15 | 16 | 17 | 18 | 19 |
| AE-TAEA | 2.637 | 2.967 | 2.606 | 2.999 | 0.260 | 0.286 | 1.553 | 2.328 |
| 1-TEPA | 6.180 | 8.339 | 9.381 | 8.829 | 8.372 | 6.929 | 2.536 | 4.917 |
| AE-DAEP | 0.385 | 1.116 | 1.890 | 1.178 | 2.735 | 0.320 | 0.103 | 0.269 |
| AE-PEEDA | 0.094 | 0.460 | 0.627 | 0.505 | 0.663 | 0.684 | 0.051 | 0.063 |
| iAE-PEEDA | 0.000 | 0.000 | 0.000 | 0.000 | 0.000 | 0.000 | 0.000 | 0.000 |
| AE-DPE | 0.203 | 0.336 | 0.071 | 0.097 | 0.053 | 0.192 | 0.186 | 0.135 |
| BPEA | 0.099 | 0.280 | 0.687 | 0.358 | 0.583 | 0.477 | 0.063 | 0.072 |
| Others | 6.086 | 11.972 | 16.987 | 14.062 | 19.743 | 24.147 | 2.010 | 4.512 |
| MEA Conversion, % | 52.70 | 69.92 | 84.56 | 74.53 | 90.51 | 91.63 | 31.61 | 45.99 |
| DETA Conversion, % | 36.77 | 50.39 | 61.12 | 52.92 | 62.23 | 64.10 | 21.37 | 31.38 |
| Acyclic(N4), % | 92.89 | 84.57 | 74.88 | 83.01 | 68.69 | 62.02 | 96.33 | 94.03 |
| Acyclic(N5), % | 91.85 | 83.74 | 78.54 | 84.68 | 68.15 | 81.17 | 91.02 | 93.05 |
| Σ(N5)/Σ(N4), weight ratio | 0.59 | 0.77 | 0.84 | 0.78 | 0.73 | 0.56 | 0.40 | 0.55 |
| Acyclic(N4)/cyclic (< = N4), weight ratio | 5.36 | 2.55 | 1.45 | 2.23 | 0.99 | 0.74 | 8.56 | 5.86 |

TABLE III

| | Example No. | | | | | | | |
|---|---|---|---|---|---|---|---|---|
| | 20 | 21 | 22 | 23 | 24 | 25 | 26 | 27 |
| Composition Type | C | C | C | C | C | C | C | C |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 249.9 | 259.9 | 270 | 265 | 275 | 280.7 | 245.4 | 255.6 |
| Time on organics, hrs. | 23 | 27 | 48 | 53 | 71 | 96 | 119 | 143 |
| Duration of run, hrs. | 2 | 2 | 2 | 2 | 2 | 2 | 2 | 2 |
| MEA SV, gmol/hr/kgcat | 4.13 | 4.06 | 3.61 | 3.95 | 3.59 | 3.73 | 3.92 | 3.85 |
| DETA/MEA mole ratio | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 |
| Crude product composition, wt. % | | | | | | | | |
| EDA | 1.549 | 2.657 | 3.816 | 2.918 | 4.945 | 5.969 | 0.647 | 1.041 |
| MEA | 26.153 | 22.877 | 17.520 | 20.205 | 16.087 | 14.680 | 30.721 | 27.460 |
| PIP | 1.065 | 1.698 | 3.017 | 2.402 | 3.952 | 4.620 | 0.575 | 0.919 |
| DETA | 45.023 | 38.851 | 29.155 | 34.030 | 27.311 | 23.227 | 52.572 | 47.799 |
| AEEA | 1.218 | 0.982 | 0.837 | 1.081 | 0.676 | 0.509 | 1.117 | 1.247 |
| AEP | 1.053 | 1.832 | 3.443 | 2.575 | 4.691 | 5.337 | 0.059 | 0.880 |
| HEP | 0.000 | 0.000 | 0.000 | 0.000 | 0.000 | 0.000 | 0.000 | 0.000 |
| TAEA | 0.900 | 0.792 | 0.594 | 0.766 | 0.491 | 0.319 | 0.738 | 0.840 |
| 1-TETA | 5.944 | 6.306 | 6.128 | 6.849 | 5.723 | 4.369 | 4.214 | 5.237 |
| DAEP | 0.360 | 0.709 | 1.430 | 1.052 | 2.070 | 2.354 | 0.120 | 0.254 |
| PEEDA | 0.397 | 0.866 | 2.099 | 1.325 | 2.733 | 3.018 | 0.131 | 0.289 |
| DPE | 0.253 | 0.301 | 0.310 | 0.288 | 0.386 | 0.613 | 0.086 | 0.156 |
| AE-TAEA | 0.991 | 0.999 | 0.917 | 1.079 | 0.819 | 0.226 | 0.604 | 0.915 |
| 1-TEPA | 4.013 | 4.927 | 5.460 | 5.824 | 4.414 | 3.018 | 2.018 | 2.952 |
| AE-DAEP | 0.401 | 0.835 | 1.545 | 1.161 | 2.224 | 2.681 | 0.112 | 0.278 |
| AE-PEEDA | 0.400 | 0.554 | 0.512 | 0.489 | 0.511 | 0.542 | 0.121 | 0.220 |
| iAE-PEEDA | 0.000 | 0.000 | 0.000 | 0.000 | 0.000 | 0.000 | 0.000 | 0.000 |
| AE-DPE | 0.324 | 0.318 | 0.392 | 0.318 | 0.632 | 0.239 | 0.000 | 0.089 |
| BPEA | 0.176 | 0.309 | 0.369 | 0.281 | 0.202 | 0.202 | 0.054 | 0.073 |
| Others | 7.341 | 11.517 | 13.927 | 12.910 | 15.843 | 20.589 | 2.521 | 3.702 |
| MEA Conversion, % | 30.67 | 40.03 | 52.14 | 46.63 | 57.49 | 60.93 | 15.90 | 24.03 |
| DETA Conversion, % | 29.24 | 39.62 | 52.78 | 46.72 | 57.22 | 63.35 | 14.68 | 21.60 |
| Acyclic(N4), % | 87.11 | 79.08 | 63.63 | 74.06 | 54.49 | 43.92 | 93.59 | 89.67 |
| Acyclic(N5), % | 79.35 | 74.60 | 69.34 | 75.42 | 59.44 | 46.96 | 90.10 | 85.38 |
| Σ(N5)/Σ(N4), weight ratio | 0.80 | 0.88 | 0.87 | 0.89 | 0.77 | 0.64 | 0.55 | 0.66 |
| Acyclic(N4)/cyclic (< = N4), weight ratio | 2.19 | 1.31 | 0.65 | 0.99 | 0.44 | 0.29 | 5.08 | 2.43 |

TABLE IV

| | Example No. | | | | | | | | | |
|---|---|---|---|---|---|---|---|---|---|---|
| | 28 | 29 | 30 | 31 | 32 | 33 | 34 | 35 | 36 | 37 |
| Composition Type | D | D | D | D | D | D | D | D | D | D |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.9 | 259.9 | 270 | 265 | 275 | 280.7 | 245.4 | 255.6 | 250.7 | 249.7 |
| Time on organics, hrs. | 23 | 27 | 48 | 53 | 71 | 96 | 119 | 143 | 4 | 22.5 |
| Duration of run, hrs. | 2 | 2 | 2 | 2 | 2 | 2 | 2 | 2 | 2 | 2 |
| MEA SV, gmol/hr/kgcat | 3.91 | 3.98 | 3.24 | 3.97 | 3.68 | 3.71 | 3.62 | 3.79 | 5.16 | 4.70 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.813 | 1.260 | 2.398 | 1.598 | 2.314 | 2.549 | 0.484 | 0.749 | 1.094 | 0.827 |
| MEA | 21.532 | 15.622 | 10.867 | 13.317 | 7.792 | 5.589 | 27.925 | 23.876 | 20.059 | 23.108 |

TABLE IV-continued

| | | | | | | | | | | |
|---|---|---|---|---|---|---|---|---|---|---|
| PIP | 0.251 | 0.421 | 0.882 | 0.590 | 0.731 | 0.778 | 0.097 | 0.183 | 0.327 | 0.225 |
| DETA | 47.006 | 39.567 | 32.817 | 35.817 | 32.340 | 29.857 | 52.926 | 48.757 | 43.271 | 47.311 |
| AEEA | 2.748 | 2.642 | 1.046 | 2.119 | 1.372 | 1.018 | 1.990 | 2.368 | 2.409 | 2.483 |
| AEP | 0.401 | 0.686 | 1.551 | 0.829 | 1.174 | 1.246 | 0.252 | 0.319 | 0.548 | 0.347 |
| HEP | 0.000 | 0.000 | 0.000 | 0.000 | 0.000 | 0.000 | 0.000 | 0.000 | 0.000 | 0.000 |
| TAEA | 1.801 | 1.987 | 1.375 | 1.958 | 2.017 | 1.874 | 1.232 | 1.615 | 1.501 | 1.592 |
| l-TETA | 12.031 | 14.750 | 10.951 | 12.866 | 14.396 | 13.387 | 6.891 | 9.157 | 11.936 | 10.715 |
| DAEP | 0.111 | 0.253 | 1.051 | 0.455 | 0.782 | 0.853 | 0.046 | 0.075 | 0.225 | 0.098 |
| PEEDA | 0.080 | 0.230 | 0.708 | 0.335 | 0.543 | 0.599 | 0.043 | 0.066 | 0.181 | 0.076 |
| DPE | 0.112 | 0.173 | 0.437 | 0.453 | 0.539 | 0.630 | 0.067 | 0.139 | 0.174 | 0.137 |
| AE-TAEA | 1.968 | 2.920 | 2.711 | 3.016 | 4.316 | 4.170 | 0.874 | 1.511 | 2.199 | 1.958 |
| l-TEPA | 4.549 | 6.175 | 7.240 | 6.904 | 8.891 | 9.110 | 1.270 | 2.338 | 4.246 | 3.296 |
| AE-DAEP | 0.057 | 0.500 | 1.079 | 0.522 | 0.775 | 0.951 | 0.060 | 0.082 | 0.326 | 0.147 |
| AE-PEEDA | 0.000 | 0.477 | 0.256 | 0.215 | 0.250 | 0.299 | 0.000 | 0.000 | 0.181 | 0.127 |
| iAE-PEEDA | 0.000 | 0.000 | 0.000 | 0.000 | 0.000 | 0.000 | 0.000 | 0.000 | 0.000 | 0.000 |
| AE-DPE | 0.058 | 0.314 | 0.301 | 0.358 | 0.368 | 0.496 | 0.053 | 0.099 | 0.286 | 0.112 |
| BPEA | 0.185 | 0.182 | 0.313 | 0.582 | 0.348 | 0.444 | 0.056 | 0.141 | 0.107 | 0.050 |
| Others | 2.088 | 7.250 | 12.439 | 11.787 | 13.042 | 15.672 | 1.167 | 1.829 | 5.810 | 3.174 |
| MEA Conversion, % | 42.08 | 58.67 | 69.47 | 64.44 | 79.13 | 84.73 | 23.07 | 33.43 | 45.87 | 37.58 |
| DETA Conversion, % | 25.04 | 37.95 | 45.35 | 43.31 | 48.67 | 51.65 | 13.57 | 19.42 | 30.78 | 24.24 |
| Acyclic(N4), % | 97.84 | 96.21 | 84.86 | 92.25 | 89.78 | 87.99 | 98.00 | 97.46 | 95.84 | 97.51 |
| Acyclic(N5), % | 95.56 | 86.04 | 83.61 | 85.52 | 88.33 | 85.83 | 92.64 | 92.25 | 87.72 | 92.30 |
| Σ(N5)/Σ(N4), weight ratio | 0.48 | 0.60 | 0.81 | 0.72 | 0.81 | 0.89 | 0.27 | 0.37 | 0.52 | 0.45 |
| Acyclic(N4)/cyclic (< = N4), weight ratio | 14.43 | 9.47 | 2.66 | 5.56 | 4.35 | 3.71 | 16.01 | 13.75 | 9.21 | 13.89 |

| | Example No. | | | | | | | | | |
|---|---|---|---|---|---|---|---|---|---|---|
| | 38 | 39 | 40 | 41 | 42 | 43 | 44 | 45 | 46 | 47 |
| Composition Type | D | D | D | D | D | D | D | D | D | D |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 260 | 255.5 | 265.5 | 260.5 | 270.1 | 250.6 | 250 | 265.2 | 275.2 | 270.3 |
| Time on organics, hrs. | 28 | 46.5 | 52 | 71.5 | 76 | 95.5 | 118 | 145 | 148 | 170 |
| Duration of run, hrs. | 2 | 2 | 2 | 2 | 2 | 2 | 2 | 2 | 2 | 2 |
| MEA SV, gmol/hr/kgcat | 5.01 | 4.40 | 4.64 | 4.92 | 4.88 | 4.87 | 4.45 | 4.02 | 3.87 | 3.87 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 1.292 | 1.045 | 1.658 | 1.287 | 1.756 | 0.653 | 0.658 | 1.445 | 2.153 | 1.729 |
| MEA | 16.448 | 21.025 | 15.267 | 18.822 | 12.662 | 24.836 | 24.781 | 17.208 | 11.166 | 13.488 |
| PIP | 0.399 | 0.287 | 0.516 | 0.337 | 0.537 | 0.161 | 0.156 | 0.414 | 0.698 | 0.492 |
| DETA | 39.380 | 43.930 | 37.874 | 42.302 | 36.372 | 48.917 | 49.188 | 40.090 | 34.966 | 37.519 |
| AEEA | 2.393 | 2.382 | 2.051 | 2.263 | 1.834 | 2.123 | 2.116 | 1.781 | 1.886 | 1.571 |
| AEP | 0.583 | 0.411 | 0.711 | 0.476 | 0.801 | 0.303 | 0.298 | 0.559 | 0.957 | 0.762 |
| HEP | 0.000 | 0.000 | 0.000 | 0.000 | 0.000 | 0.000 | 0.000 | 0.000 | 0.000 | 0.000 |
| TAEA | 1.770 | 1.662 | 1.767 | 1.798 | 1.909 | 1.483 | 1.480 | 1.667 | 1.789 | 1.659 |
| l-TETA | 13.854 | 11.854 | 12.904 | 12.705 | 13.617 | 9.174 | 9.069 | 11.193 | 12.877 | 11.276 |
| DAEP | 0.249 | 0.137 | 0.361 | 0.199 | 0.443 | 0.094 | 0.073 | 0.298 | 0.501 | 0.557 |
| PEEDA | 0.183 | 0.102 | 0.256 | 0.143 | 0.304 | 0.067 | 0.057 | 0.210 | 0.366 | 0.360 |
| DPE | 0.205 | 0.156 | 0.410 | 0.181 | 0.122 | 0.066 | 0.128 | 0.100 | 0.135 | 0.412 |
| AE-TAEA | 3.040 | 2.393 | 3.401 | 2.775 | 3.772 | 1.512 | 1.451 | 2.977 | 3.693 | 3.182 |
| l-TEPA | 5.724 | 4.313 | 6.650 | 4.894 | 6.982 | 2.416 | 2.266 | 5.519 | 7.108 | 5.762 |
| AE-DAEP | 0.392 | 0.289 | 0.446 | 0.324 | 0.477 | 0.105 | 0.070 | 0.367 | 0.112 | 0.680 |
| AE-PEEDA | 0.182 | 0.086 | 0.178 | 0.101 | 0.174 | 0.062 | 0.029 | 0.122 | 0.140 | 0.117 |
| iAE-PEEDA | 0.000 | 0.000 | 0.000 | 0.000 | 0.000 | 0.000 | 0.000 | 0.000 | 0.000 | 0.000 |
| AL-DPE | 0.279 | 0.133 | 0.078 | 0.141 | 0.077 | 0.044 | 0.046 | 0.058 | 0.278 | 0.193 |
| BPEA | 0.278 | 0.178 | 0.626 | 0.192 | 0.706 | 0.129 | 0.129 | 0.572 | 0.680 | 0.209 |
| Others | 7.869 | 5.310 | 8.286 | 5.602 | 9.166 | 2.965 | 2.416 | 7.580 | 9.685 | 10.183 |
| MEA Conversion, % | 55.95 | 43.59 | 58.83 | 49.17 | 65.41 | 32.04 | 31.64 | 52.56 | 68.72 | 62.38 |
| DETA Conversion, % | 37.48 | 30.13 | 39.45 | 32.28 | 41.11 | 20.65 | 19.56 | 34.48 | 41.95 | 37.97 |
| Acyclic(N4), % | 96.06 | 97.15 | 93.45 | 96.51 | 94.69 | 97.89 | 97.60 | 95.47 | 93.59 | 90.67 |
| Acyclic(N5), % | 88.54 | 90.71 | 88.30 | 90.98 | 88.22 | 92.00 | 93.08 | 88.34 | 89.91 | 88.16 |
| Σ(N5)/Σ(N4), weight ratio | 0.60 | 0.53 | 0.72 | 0.56 | 0.74 | 0.39 | 0.36 | 0.71 | 0.76 | 0.71 |
| Acyclic(N4)/cyclic (< = N4), weight ratio | 9.63 | 12.34 | 6.50 | 10.84 | 7.02 | 15.35 | 14.76 | 8.11 | 5.51 | 5.00 |

| | Example No. | | | | | | | | | |
|---|---|---|---|---|---|---|---|---|---|---|
| | 48 | 49 | 50 | 51 | 52 | 53 | 54 | 55 | 56 | |
| Composition Type | D | D | D | D | D | D | D | D | D | |
| Composition weight, gm | 50 | 50 | 50 | 50 | 50 | 50 | 50 | 50 | 50 | |
| Pressure, psig | 600 | 600 | 600 | 600 | 600 | 600 | 600 | 600 | 600 | |
| Temperature, °C. | 280.7 | 250.7 | 265.7 | 259.9 | 270 | 250.4 | 265.5 | 250 | 250 | |
| Time on organics, hrs. | 172 | 191 | 196 | 216 | 220 | 239 | 244 | 262 | 286 | |
| Duration of run, hrs. | 2 | 2 | 2 | 2 | 2 | 2 | 2 | 2 | 2 | |
| MEA SV, gmol/hr/kgcat | 3.95 | 4.44 | 4.42 | 4.32 | 4.52 | 4.32 | 4.59 | 4.28 | 3.96 | |
| DETA/MEA mole ratio | 0.99 | 0.99 | 0.99 | 0.99 | 0.99 | 0.99 | 0.99 | 0.99 | 0.99 | |
| NH$_3$/MEA mole ratio | 5.98 | 5.98 | 5.98 | 5.98 | 5.98 | 5.98 | 5.98 | 5.98 | 5.98 | |
| Crude product composition, wt. % | | | | | | | | | | |
| EDA | 2.487 | 0.562 | 1.308 | 0.998 | 1.594 | 0.620 | 1.133 | 0.494 | 0.560 | |

TABLE IV-continued

| | | | | | | | | | |
|---|---|---|---|---|---|---|---|---|---|
| MEA | 8.016 | 26.365 | 19.043 | 21.551 | 14.399 | 26.157 | 17.426 | 24.474 | 23.986 |
| PIP | 0.837 | 0.141 | 0.371 | 0.259 | 0.462 | 0.139 | 0.304 | 0.127 | 0.146 |
| DETA | 31.719 | 51.019 | 41.915 | 45.886 | 37.620 | 49.403 | 39.117 | 47.899 | 48.509 |
| AEEA | 1.511 | 2.181 | 2.319 | 2.375 | 1.945 | 2.052 | 2.033 | 1.815 | 1.816 |
| AEP | 1.224 | 0.289 | 0.484 | 0.404 | 0.668 | 0.283 | 0.454 | 0.283 | 0.038 |
| HEP | 0.000 | 0.000 | 0.000 | 0.000 | 0.000 | 0.000 | 0.000 | 0.000 | 0.000 |
| TAEA | 1.853 | 1.399 | 1.786 | 1.788 | 1.875 | 1.377 | 1.723 | 1.389 | 1.454 |
| 1-TETA | 13.608 | 8.273 | 11.292 | 10.921 | 12.338 | 7.973 | 10.608 | 7.992 | 8.498 |
| DAEP | 0.762 | 0.078 | 0.234 | 0.143 | 0.335 | 0.095 | 0.209 | 0.102 | 0.104 |
| PEEDA | 0.533 | 0.051 | 0.168 | 0.103 | 0.259 | 0.072 | 0.149 | 0.071 | 0.079 |
| DPE | 0.509 | 0.144 | 0.321 | 0.215 | 0.438 | 0.171 | 0.354 | 0.160 | 0.170 |
| AE-TAEA | 4.179 | 0.1285 | 2.934 | 2.270 | 3.574 | 1.424 | 2.823 | 1.514 | 1.614 |
| 1-TEPA | 8.123 | 2.016 | 4.826 | 3.679 | 6.077 | 2.067 | 4.493 | 2.110 | 2.426 |
| AE-DAEP | 0.938 | 0.067 | 0.268 | 0.108 | 0.461 | 0.171 | 0.264 | 0.267 | 0.166 |
| AE-PEEDA | 0.201 | 0.060 | 0.086 | 0.066 | 0.101 | 0.061 | 0.134 | 0.107 | 0.000 |
| iAE-PEEDA | 0.000 | 0.000 | 0.000 | 0.000 | 0.000 | 0.000 | 0.000 | 0.000 | 0.000 |
| AE-DPE | 0.098 | 0.084 | 0.239 | 0.087 | 0.138 | 0.112 | 0.246 | 0.120 | 0.053 |
| BPEA | 0.850 | 0.042 | 0.137 | 0.075 | 0.193 | 0.046 | 0.175 | 0.053 | 0.056 |
| Others | 12.032 | 2.444 | 6.821 | 4.133 | 9.534 | 2.987 | 7.006 | 3.146 | 3.176 |
| MEA Conversion, % | 77.91 | 28.64 | 48.59 | 41.59 | 60.59 | 28.29 | 49.91 | 30.83 | 33.03 |
| DETA Conversion, % | 48.20 | 18.14 | 32.92 | 26.27 | 38.96 | 19.71 | 33.35 | 19.75 | 19.71 |
| Acyclic(N4), % | 89.54 | 97.24 | 94.75 | 96.48 | 93.21 | 96.49 | 94.53 | 96.56 | 96.56 |
| Acyclic(N5), % | 85.48 | 92.81 | 91.37 | 94.61 | 91.34 | 89.90 | 89.90 | 86.86 | 93.58 |
| Σ(N5)/Σ(N4), weight ratio | 0.83 | 0.35 | 0.61 | 0.47 | 0.69 | 0.40 | 0.62 | 0.42 | 0.41 |
| Acyclic(N4)/cyclic (< = N4), weight ratio | 3.99 | 13.72 | 8.28 | 11.28 | 6.56 | 12.25 | 8.37 | 12.60 | 12.29 |
| | 4.60 | 17.25 | 10.39 | 13.95 | 8.23 | 15.79 | 11.03 | 16.06 | 15.57 |

TABLE V

| | Example No. | | | | | | | | |
|---|---|---|---|---|---|---|---|---|---|
| | 57 | 58 | 59 | 60 | 61 | 62 | 63 | 64 | 65 |
| Composition Type | E | E | E | E | E | E | E | E | E |
| Composition weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 249.2 | 249.8 | 259.9 | 264.9 | 269.9 | 254.8 | 244.9 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 3.05 | 3.45 | 3.71 | 3.37 | 3.66 | 4.11 | 3.75 | 3.37 | 3.61 |
| DETA/MEA mole ratio | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.701 | 1.330 | 2.175 | 2.857 | 3.642 | 1.575 | 0.790 | 2.998 | 4.045 |
| MEA | 16.452 | 20.045 | 13.804 | 10.226 | 7.809 | 18.066 | 25.597 | 9.273 | 6.909 |
| PIP | 0.640 | 0.536 | 0.952 | 1.209 | 1.520 | 0.606 | 0.260 | 1.165 | 1.515 |
| DETA | 35.879 | 42.232 | 35.213 | 31.459 | 28.823 | 40.057 | 48.800 | 31.599 | 29.253 |
| AEEA | 1.848 | 2.310 | 2.025 | 1.615 | 1.216 | 2.188 | 2.179 | 1.469 | 1.067 |
| AEP | 0.845 | 0.661 | 1.314 | 1.822 | 2.394 | 0.806 | 0.375 | 1.797 | 2.395 |
| HEP | 0.000 | 0.000 | 0.000 | 0.000 | 0.000 | 0.000 | 0.000 | 0.000 | 0.000 |
| TAEA | 1.322 | 1.559 | 1.518 | 1.409 | 1.216 | 1.638 | 1.501 | 1.434 | 1.240 |
| 1-TETA | 11.392 | 12.975 | 14.107 | 14.075 | 13.354 | 13.401 | 10.153 | 13.748 | 13.019 |
| DAEP | 0.426 | 0.224 | 0.652 | 1.052 | 1.477 | 0.312 | 0.097 | 1.047 | 1.571 |
| PEEDA | 0.338 | 0.171 | 0.491 | 0.777 | 1.119 | 0.227 | 0.067 | 0.783 | 1.163 |
| DPE | 0.378 | 0.162 | 0.370 | 0.148 | 0.166 | 0.178 | 0.103 | 0.153 | 0.172 |
| AE-TAEA | 2.369 | 2.370 | 3.157 | 3.316 | 3.106 | 2.829 | 1.535 | 3.212 | 3.251 |
| 1-TEPA | 5.829 | 5.299 | 8.162 | 9.154 | 9.766 | 5.998 | 2.509 | 8.811 | 9.487 |
| AE-DAEP | 0.502 | 0.250 | 0.590 | 0.924 | 1.403 | 0.326 | 0.060 | 0.968 | 1.481 |
| AE-PEEDA | 0.347 | 0.087 | 0.124 | 0.292 | 0.486 | 0.090 | 0.044 | 0.282 | 0.455 |
| iAE-PEEDA | 0.000 | 0.000 | 0.000 | 0.000 | 0.000 | 0.000 | 0.000 | 0.000 | 0.000 |
| AE-DPE | 0.232 | 0.275 | 0.287 | 0.246 | 0.088 | 0.181 | 0.082 | 0.038 | 0.044 |
| BPEA | 0.378 | 0.316 | 0.172 | 0.212 | 0.728 | 0.108 | 0.026 | 0.237 | 0.689 |
| Others | 6.553 | 3.689 | 8.018 | 10.689 | 12.800 | 5.245 | 2.365 | 11.008 | 12.985 |
| MEA Conversion, % | 52.34 | 45.74 | 62.87 | 72.31 | 78.98 | 51.01 | 30.96 | 74.50 | 81.34 |
| DETA Conversion, % | 38.38 | 32.23 | 43.85 | 49.50 | 54.02 | 35.61 | 21.97 | 48.49 | 53.19 |
| Acyclic(N4), % | 91.74 | 96.30 | 91.16 | 88.66 | 84.05 | 95.43 | 97.74 | 88.44 | 83.06 |
| Acyclic(N5), % | 84.87 | 89.18 | 90.60 | 88.15 | 82.62 | 92.58 | 94.97 | 88.74 | 82.66 |
| Σ(N5)/Σ(N4), weight ratio | 0.69 | 0.56 | 0.72 | 0.80 | 0.89 | 0.60 | 0.35 | 0.78 | 0.89 |
| Acyclic(N4)/cyclic (< = N4), weight ratio | 4.83 | 8.27 | 4.13 | 3.09 | 2.18 | 7.05 | 12.88 | 3.06 | 2.09 |

TABLE VI

| | Example No. | | | | | | | | |
|---|---|---|---|---|---|---|---|---|---|
| | 66 | 67 | 68 | 69 | 70 | 71 | 72 | 73 | 74 |
| Composition Type | F | F | F | F | F | F | F | F | F |
| Composition weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 249.2 | 249.8 | 259.9 | 264.9 | 269.9 | 254.8 | 244.9 | 269.2 | 274.5 |

TABLE VI-continued

| | Example No. | | | | | | | | |
|---|---|---|---|---|---|---|---|---|---|
| | 66 | 67 | 68 | 69 | 70 | 71 | 72 | 73 | 74 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 2.81 | 3.68 | 3.89 | 3.54 | 3.97 | 4.37 | 3.98 | 3.57 | 3.82 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.087 | 0.784 | 1.159 | 1.518 | 1.787 | 0.898 | 0.427 | 1.694 | 2.168 |
| MEA | 18.000 | 23.201 | 17.032 | 13.812 | 11.331 | 21.539 | 28.009 | 12.798 | 9.998 |
| PIP | 0.304 | 0.215 | 0.374 | 0.499 | 0.603 | 0.261 | 0.099 | 0.550 | 0.705 |
| DETA | 38.387 | 48.461 | 41.116 | 37.786 | 35.688 | 46.385 | 52.406 | 37.936 | 35.454 |
| AEEA | 1.924 | 2.613 | 2.539 | 2.224 | 1.893 | 2.489 | 2.034 | 2.026 | 1.642 |
| AEP | 0.449 | 0.342 | 0.517 | 0.696 | 0.879 | 0.393 | 0.244 | 0.797 | 1.019 |
| HEP | 0.000 | 0.000 | 0.000 | 0.000 | 0.000 | 0.000 | 0.000 | 0.000 | 0.000 |
| TAEA | 1.318 | 1.639 | 1.852 | 1.906 | 1.859 | 1.711 | 1.190 | 1.917 | 1.886 |
| 1-TETA | 10.672 | 10.861 | 13.747 | 14.589 | 13.661 | 10.892 | 7.078 | 13.335 | 13.840 |
| DAEP | 0.198 | 0.087 | 0.200 | 0.337 | 0.533 | 0.121 | 0.037 | 0.403 | 0.653 |
| PEEDA | 0.174 | 0.066 | 0.178 | 0.212 | 0.342 | 0.087 | 0.032 | 0.284 | 0.424 |
| DPE | 0.179 | 0.118 | 0.179 | 0.221 | 0.417 | 0.120 | 0.055 | 0.352 | 0.139 |
| AE-TAEA | 2.140 | 1.768 | 3.096 | 3.996 | 4.461 | 2.295 | 1.015 | 3.949 | 4.557 |
| 1-TEPA | 4.234 | 2.982 | 5.888 | 7.317 | 8.157 | 3.420 | 1.361 | 7.182 | 8.348 |
| AE-DAEP | 0.296 | 0.057 | 0.409 | 0.400 | 0.522 | 0.133 | 0.088 | 0.409 | 0.588 |
| AE-PEEDA | 0.088 | 0.000 | 0.334 | 0.106 | 0.146 | 0.036 | 0.000 | 0.096 | 0.134 |
| iAE-PEEDA | 0.000 | 0.000 | 0.000 | 0.000 | 0.000 | 0.000 | 0.000 | 0.000 | 0.000 |
| AE-DPE | 0.160 | 0.104 | 0.269 | 0.268 | 0.263 | 0.116 | 0.063 | 0.216 | 0.185 |
| BPEA | 0.267 | 0.172 | 0.142 | 0.179 | 0.194 | 0.048 | 0.026 | 0.155 | 0.204 |
| Others | 4.394 | 1.773 | 5.061 | 7.143 | 9.034 | 3.187 | 1.556 | 7.761 | 10.098 |
| MEA Conversion, % | 45.31 | 36.86 | 54.05 | 62.75 | 69.21 | 40.96 | 23.12 | 65.04 | 72.98 |
| DETA Converison, % | 30.85 | 21.83 | 34.25 | 39.59 | 42.51 | 24.63 | 14.72 | 38.57 | 43.21 |
| Acyclic(N4), % | 95.59 | 97.86 | 96.54 | 95.52 | 92.30 | 97.45 | 98.50 | 93.60 | 92.81 |
| Acyclic(N5), % | 88.69 | 93.42 | 88.59 | 92.21 | 91.80 | 94.45 | 93.00 | 92.68 | 92.06 |
| $\Sigma(N5)/\Sigma(N4)$, weight ratio | 0.57 | 0.39 | 0.62 | 0.71 | 0.81 | 0.46 | 0.30 | 0.73 | 0.82 |
| Acyclic(N4)/cyclic ($\leq$ N4), weight ratio | 9.17 | 15.04 | 10.75 | 8.38 | 5.58 | 12.79 | 17.59 | 6.38 | 5.34 |

TABLE VII

| | Example No. | | | | | | | | |
|---|---|---|---|---|---|---|---|---|---|
| | 75 | 76 | 77 | 78 | 79 | 80 | 81 | 82 | 83 |
| Composition Type | G | G | G | G | G | G | G | G | G |
| Composition weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 248.2 | 249.8 | 259.9 | 264.9 | 269.9 | 254.8 | 244.8 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 2.81 | 3.53 | 3.71 | 3.46 | 3.59 | 3.87 | 2.57 | 2.86 | 3.23 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.256 | 0.898 | 1.478 | 1.884 | 2.373 | 1.036 | 0.465 | 1.816 | 2.297 |
| MEA | 25.808 | 27.657 | 23.849 | 20.875 | 18.992 | 27.163 | 30.642 | 19.820 | 18.074 |
| PIP | 0.741 | 0.635 | 1.097 | 1.449 | 1.776 | 0.782 | 0.318 | 1.333 | 1.650 |
| DETA | 46.166 | 50.830 | 44.501 | 41.541 | 37.635 | 48.978 | 54.604 | 40.543 | 39.246 |
| AEEA | 1.262 | 1.412 | 1.399 | 1.264 | 1.114 | 1.392 | 1.370 | 1.307 | 1.228 |
| AEP | 0.698 | 0.614 | 1.115 | 1.609 | 2.034 | 0.761 | 0.370 | 1.447 | 1.897 |
| HEP | 0.000 | 0.000 | 0.000 | 0.000 | 0.000 | 0.000 | 0.000 | 0.000 | 0.000 |
| TAEA | 1.061 | 1.182 | 1.300 | 1.247 | 1.133 | 1.126 | 0.903 | 1.223 | 1.288 |
| 1-TETA | 6.765 | 6.611 | 7.971 | 8.544 | 8.553 | 6.512 | 4.641 | 8.127 | 8.926 |
| DAEP | 0.208 | 0.157 | 0.077 | 0.663 | 0.883 | 0.231 | 0.068 | 0.527 | 0.791 |
| PEEDA | 0.205 | 0.143 | 0.366 | 0.645 | 0.886 | 0.213 | 0.055 | 0.541 | 0.782 |
| DPE | 0.113 | 0.071 | 0.219 | 0.258 | 0.341 | 0.119 | 0.033 | 0.233 | 0.284 |
| AE-TAEA | 1.055 | 1.082 | 1.616 | 1.535 | 1.657 | 1.234 | 0.646 | 1.783 | 1.929 |
| 1-TEPA | 2.631 | 2.675 | 4.495 | 5.280 | 5.850 | 2.897 | 0.093 | 4.793 | 5.840 |
| AE-DAEP | 0.282 | 0.121 | 0.395 | 0.609 | 0.911 | 0.196 | 0.144 | 0.532 | 0.763 |
| AE-PEEDA | 0.292 | 0.151 | 0.092 | 0.119 | 0.165 | 0.038 | 0.053 | 0.122 | 0.135 |
| iAE-PEEDA | 0.000 | 0.000 | 0.000 | 0.000 | 0.000 | 0.000 | 0.000 | 0.000 | 0.000 |
| AE-DPE | 0.145 | 0.056 | 0.248 | 0.182 | 0.222 | 0.075 | 0.051 | 0.226 | 0.172 |
| BPEA | 0.092 | 0.102 | 0.103 | 0.126 | 0.256 | 0.045 | 0.017 | 0.125 | 0.148 |
| Others | 4.080 | 2.114 | 6.330 | 7.633 | 9.871 | 3.590 | 2.398 | 7.053 | 7.859 |
| MEA Conversion, % | 27.62 | 25.05 | 36.44 | 44.22 | 49.24 | 26.50 | 16.41 | 44.75 | 50.95 |
| DETA Converison, % | 23.25 | 18.34 | 29.70 | 34.20 | 40.37 | 21.43 | 11.69 | 33.00 | 36.86 |
| Acyclic(N4), % | 93.68 | 95.43 | 93.13 | 86.19 | 82.11 | 93.10 | 97.23 | 87.77 | 84.60 |
| Acyclic(N5), % | 81.93 | 89.70 | 87.91 | 86.79 | 82.82 | 92.02 | 73.46 | 86.72 | 86.42 |
| $\Sigma(N5)/\Sigma(N4)$, weight ratio | 0.53 | 0.51 | 0.69 | 0.69 | 0.76 | 0.54 | 0.17 | 0.71 | 0.74 |
| Acyclic(N4)/cyclic | 3.97 | 4.80 | 3.20 | 2.11 | 1.63 | 3.62 | 6.55 | 2.28 | 1.88 |

TABLE VII-continued

| | Example No. | | | | | | | | |
|---|---|---|---|---|---|---|---|---|---|
| | 75 | 76 | 77 | 78 | 79 | 80 | 81 | 82 | 83 |

(< = N4), weight ratio

TABLE VIII

| | Example No. | | | | | | | | | |
|---|---|---|---|---|---|---|---|---|---|---|
| | 84 | 85 | 86 | 87 | 88 | 89 | 90 | 91 | 92 | 93 |
| Composition Type | H | H | H | H | H | H | H | H | H | H |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.5 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 92 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.34 | 5.65 | 6.24 | 6.38 | 8.47 | 6.90 | 6.07 | 5.74 | 6.46 | 5.51 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.699 | 0.991 | 0.581 | 0.845 | 0.904 | 1.637 | 0.332 | 0.557 | 0.575 | 0.259 |
| MEA | 30.881 | 26.979 | 30.239 | 25.449 | 23.586 | 17.207 | 30.424 | 27.661 | 28.796 | 31.430 |
| PIP | 0.175 | 0.376 | 0.190 | 0.382 | 0.461 | 0.971 | 0.111 | 0.252 | 0.248 | 0.099 |
| DETA | 54.402 | 53.966 | 56.223 | 52.550 | 52.679 | 47.929 | 58.899 | 56.255 | 55.809 | 58.323 |
| AEEA | 2.275 | 3.020 | 2.563 | 2.952 | 3.082 | 2.508 | 2.232 | 2.891 | 2.746 | 2.097 |
| AEP | 0.295 | 0.411 | 0.323 | 0.398 | 0.511 | 0.939 | 0.287 | 0.368 | 0.336 | 0.287 |
| HEP | 0.000 | 0.000 | 0.000 | 0.000 | 0.000 | 0.000 | 0.000 | 0.000 | 0.000 | 0.000 |
| TAEA | 0.544 | 0.915 | 0.601 | 0.901 | 1.106 | 1.536 | 0.566 | 0.803 | 0.731 | 0.444 |
| l-TETA | 3.185 | 5.582 | 3.529 | 5.218 | 6.542 | 9.101 | 3.328 | 4.694 | 4.368 | 2.706 |
| DAEP | 0.103 | 0.030 | 0.056 | 0.111 | 0.131 | 0.332 | 0.046 | 0.086 | 0.060 | 0.023 |
| PEEDA | 0.033 | 0.040 | 0.046 | 0.025 | 0.026 | 0.319 | 0.036 | 0.039 | 0.032 | 0.026 |
| DPE | 0.079 | 0.078 | 0.059 | 0.071 | 0.094 | 0.191 | 0.047 | 0.059 | 0.058 | 0.000 |
| AE-TAEA | 0.120 | 0.479 | 0.160 | 0.566 | 0.782 | 0.819 | 0.164 | 0.345 | 0.340 | 0.110 |
| l-TEPA | 0.223 | 1.046 | 0.335 | 1.448 | 1.933 | 4.344 | 0.305 | 0.748 | 0.777 | 0.175 |
| AE-DAEP | 0.054 | 0.000 | 0.000 | 0.035 | 0.058 | 0.101 | 0.000 | 0.000 | 0.000 | 0.000 |
| AE-PEEDA | 0.000 | 0.043 | 0.000 | 0.037 | 0.000 | 0.047 | 0.062 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.085 | 0.000 | 0.053 | 0.000 | 0.000 | 0.108 | 0.000 | 0.000 | 0.000 | 0.098 |
| BPEA | 0.000 | 0.060 | 0.000 | 0.078 | 0.052 | 0.141 | 0.000 | 0.000 | 0.000 | 0.000 |
| Others | 1.439 | 1.936 | 1.433 | 2.104 | 2.736 | 5.251 | 1.312 | 1.757 | 1.538 | 0.936 |
| MEA Conversion, % | 13.32 | 26.12 | 16.89 | 28.40 | 35.09 | 53.51 | 17.91 | 24.54 | 21.17 | 13.94 |
| DETA Converison, % | 9.48 | 12.39 | 8.40 | 12.35 | 14.06 | 23.24 | 5.79 | 9.02 | 9.43 | 5.33 |
| Acyclic(N4), % | 94.50 | 97.75 | 96.19 | 96.70 | 96.80 | 92.65 | 96.76 | 96.72 | 97.11 | 98.43 |
| Acyclic(N5), % | 71.06 | 93.57 | 90.33 | 92.98 | 96.07 | 93.91 | 88.20 | 100 | 100 | 74.27 |
| $\Sigma$(N5)/$\Sigma$(N4), weight ratio | 0.12 | 0.24 | 0.12 | 0.34 | 0.35 | 0.57 | 0.13 | 0.19 | 0.21 | 0.12 |
| Acyclic(N4)/cyclic (< = N4), weight ratio | 5.42 | 6.93 | 6.10 | 6.18 | 6.23 | 3.86 | 7.36 | 6.81 | 6.91 | 7.21 |

| | Example No. | | | | | | | | | |
|---|---|---|---|---|---|---|---|---|---|---|
| | 94 | 95 | 96 | 97 | 98 | 99 | 100 | 101 | 102 | 103 |
| Composition Type | H | H | H | H | H | H | H | H | H | H |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.5 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 92 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.31 | 5.47 | 5.77 | 6.00 | 6.06 | 6.55 | 5.78 | 5.50 | 5.21 | 5.66 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.745 | 0.944 | 0.594 | 0.847 | 1.030 | 1.615 | 0.327 | 0.590 | 0.591 | 0.329 |
| MEA | 30.660 | 27.781 | 30.325 | 25.425 | 24.014 | 17.349 | 31.104 | 27.787 | 28.697 | 31.814 |
| PIP | 0.148 | 0.317 | 0.168 | 0.346 | 0.455 | 0.912 | 0.099 | 0.228 | 0.218 | 0.088 |
| DETA | 56.688 | 54.036 | 55.722 | 43.130 | 52.088 | 48.017 | 59.117 | 56.024 | 55.945 | 58.205 |
| AEEA | 2.475 | 3.096 | 2.580 | 3.089 | 3.100 | 2.630 | 2.204 | 2.899 | 2.826 | 2.086 |
| AEP | 0.299 | 0.420 | 0.298 | 0.379 | 0.470 | 0.914 | 0.261 | 0.367 | 0.346 | 0.274 |
| HEP | 0.000 | 0.000 | 0.000 | 0.000 | 0.000 | 0.000 | 0.000 | 0.000 | 0.000 | 0.000 |
| TAEA | 0.588 | 0.879 | 0.588 | 0.969 | 1.022 | 1.530 | 0.489 | 0.798 | 0.714 | 0.410 |
| l-TETA | 3.553 | 5.158 | 3.445 | 5.562 | 5.935 | 8.838 | 2.904 | 4.702 | 4.162 | 2.520 |
| DAEP | 0.105 | 0.125 | 0.051 | 0.095 | 0.114 | 0.319 | 0.031 | 0.066 | 0.065 | 0.018 |
| PEEDA | 0.026 | 0.043 | 0.060 | 0.030 | 0.042 | 0.332 | 0.042 | 0.036 | 0.027 | 0.022 |
| DPE | 0.055 | 0.072 | 0.073 | 0.088 | 0.099 | 0.211 | 0.040 | 0.071 | 0.055 | 0.000 |
| AE-TAEA | 0.066 | 0.361 | 0.137 | 0.513 | 0.679 | 1.746 | 0.102 | 0.299 | 0.261 | 0.078 |
| l-TEPA | 0.144 | 0.806 | 0.322 | 1.126 | 1.742 | 3.970 | 0.183 | 0.650 | 0.621 | 0.101 |
| AE-DAEP | 0.068 | 0.000 | 0.000 | 0.030 | 0.037 | 0.180 | 0.000 | 0.000 | 0.000 | 0.000 |
| AE-PEEDA | 0.000 | 0.000 | 0.000 | 0.000 | 0.056 | 0.080 | 0.164 | 0.030 | 0.092 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.000 | 0.058 | 0.000 | 0.000 | 0.000 | 0.000 | 0.000 | 0.000 | 0.154 |
| BPEA | 0.000 | 0.000 | 0.000 | 0.056 | 0.046 | 0.093 | 0.000 | 0.000 | 0.000 | 0.000 |
| Others | 1.371 | 1.735 | 1.521 | 2.443 | 2.782 | 5.517 | 1.044 | 1.685 | 1.503 | 0.926 |

TABLE VIII-continued

| | | | | | | | | | | |
|---|---|---|---|---|---|---|---|---|---|---|
| MEA Conversion, % | 16.17 | 23.60 | 16.23 | 29.21 | 33.10 | 52.96 | 15.90 | 23.93 | 21.18 | 12.82 |
| DETA Converison, % | 8.12 | 11.91 | 8.75 | 12.31 | 13.98 | 22.83 | 5.25 | 9.08 | 8.91 | 5.45 |
| Acyclic(N4), % | 95.65 | 96.13 | 95.62 | 96.81 | 96.43 | 92.31 | 96.73 | 96.92 | 97.05 | 98.63 |
| Acyclic(N5), % | 75.52 | 100.00 | 88.65 | 94.91 | 94.51 | 94.17 | 63.39 | 96.93 | 90.51 | 53.84 |
| $\Sigma(N5)/\Sigma(N4)$, weight ratio | 0.06 | 0.18 | 0.12 | 0.25 | 0.35 | 0.54 | 0.12 | 0.17 | 0.19 | 0.11 |
| Acyclic(N4)/cyclic ($<=$ N4), weight ratio | 6.50 | 6.15 | 6.19 | 6.93 | 5.88 | 3.85 | 7.13 | 7.13 | 6.83 | 7.26 |

TABLE IX

| | Example No. | | | | | | | |
|---|---|---|---|---|---|---|---|---|
| | 104 | 105 | 106 | 107 | 108 | 109 | 110 | 111 |
| Composition Type | I | I | I | I | I | I | I | I |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.1 | 259.9 | 270.4 | 250 | 250 | 265.4 | 274.9 | 270.4 |
| Time on organics, hrs. | 49 | 69 | 73 | 92 | 117 | 141 | 145 | 164 |
| Duration of run, hrs. | 2 | 2 | 2 | 2 | 2 | 2 | 2 | 2 |
| MEA SV, gmol/hr/kgcat | 6.27 | 5.79 | 6.32 | 6.13 | 5.94 | 5.89 | 5.95 | 6.07 |
| DETA/MEA mole ratio | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 0.646 | 0.996 | 1.453 | 0.520 | 0.455 | 1.300 | 2.007 | 1.580 |
| MEA | 26.654 | 23.680 | 16.639 | 28.140 | 28.547 | 22.094 | 15.810 | 19.303 |
| PIP | 0.159 | 0.228 | 0.386 | 0.099 | 0.087 | 0.283 | 0.468 | 0.350 |
| DETA | 51.837 | 47.809 | 41.131 | 53.445 | 54.624 | 47.199 | 40.533 | 44.569 |
| AEEA | 2.147 | 2.219 | 2.091 | 1.899 | 1.991 | 2.285 | 1.858 | 2.050 |
| AEP | 0.366 | 0.391 | 0.584 | 0.286 | 0.291 | 0.441 | 0.652 | 0.586 |
| HEP | 0.000 | 0.000 | 0.000 | 0.000 | 0.000 | 0.000 | 0.000 | 0.000 |
| TAEA | 1.404 | 1.960 | 2.022 | 1.297 | 1.245 | 1.889 | 1.973 | 1.833 |
| l-TETA | 9.038 | 10.383 | 12.919 | 7.486 | 7.272 | 11.110 | 12.264 | 11.044 |
| DAEP | 0.091 | 0.136 | 0.267 | 0.047 | 0.050 | 0.144 | 0.296 | 0.227 |
| PEEDA | 0.049 | 0.069 | 0.074 | 0.030 | 0.025 | 0.066 | 0.089 | 0.070 |
| DPE | 0.102 | 0.194 | 0.327 | 0.078 | 0.085 | 0.208 | 0.379 | 0.309 |
| AE-TAEA | 1.004 | 1.822 | 3.107 | 0.781 | 0.689 | 1.905 | 3.070 | 2.472 |
| l-TEPA | 1.515 | 2.906 | 5.194 | 1.189 | 1.007 | 2.936 | 5.147 | 4.012 |
| AE-DAEP | 0.043 | 0.106 | 0.253 | 0.000 | 0.000 | 0.051 | 0.422 | 0.311 |
| AE-PEEDA | 0.000 | 0.000 | 0.112 | 0.000 | 0.000 | 0.000 | 0.118 | 0.082 |
| iAE-PEEDA | 0.000 | 0.000 | 0.000 | 0.000 | 0.000 | 0.000 | 0.000 | 0.000 |
| AE-DPE | 0.000 | 0.000 | 0.240 | 0.000 | 0.000 | 0.000 | 0.343 | 0.373 |
| BPEA | 0.085 | 0.242 | 0.492 | 0.078 | 0.000 | 0.281 | 0.275 | 0.212 |
| Others | 1.551 | 4.275 | 6.422 | 1.397 | 1.017 | 3.348 | 7.308 | 5.745 |
| MEA Conversion, % | 27.88 | 35.83 | 54.96 | 23.58 | 22.81 | 40.26 | 56.94 | 48.09 |
| DETA Converison, % | 16.85 | 23.20 | 34.01 | 13.96 | 12.53 | 24.35 | 34.55 | 28.95 |
| Acyclic(N4), % | 97.71 | 96.35 | 95.71 | 98.25 | 98.13 | 96.87 | 94.89 | 95.49 |
| Acyclic(N5), % | 95.12 | 93.12 | 88.30 | 96.16 | 100.00 | 93.55 | 87.63 | 86.86 |
| $\Sigma(N5)/\Sigma(N4)$, weight ratio | 0.24 | 0.46 | 0.60 | 0.22 | 0.19 | 0.38 | 0.62 | 0.55 |
| Acyclic(N4)/cyclic ($<=$ N4), weight ratio | 13.55 | 10.36 | 9.11 | 16.20 | 15.74 | 11.35 | 7.54 | 8.33 |

| | Example No. | | | | | | |
|---|---|---|---|---|---|---|---|
| | 112 | 113 | 114 | 115 | 116 | 117 | 118 |
| Composition Type | I | I | I | I | I | I | I |
| Composition weight, gm | 50 | 50 | 50 | 50 | 50 | 50 | 50 |
| Pressure, psig | 600 | 600 | 600 | 600 | 600 | 600 | 600 |
| Temperature, °C. | 280.5 | 250.3 | 255.6 | 260.5 | 270.5 | 250.4 | 260.4 |
| Time on organics, hrs. | 168 | 187 | 192 | 212 | 216 | 235 | 240 |
| Duration of run, hrs. | 2 | 2 | 2 | 2 | 2 | 2 | 2 |
| MEA SV, gmol/hr/kgcat | 6.15 | 5.94 | 6.33 | 5.99 | 6.27 | 5.90 | 6.53 |
| DETA/MEA mole ratio | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 |
| Crude product composition, wt. % | | | | | | | |
| EDA | 2.469 | 0.514 | 0.593 | 0.846 | 1.480 | 0.481 | 0.783 |
| MEA | 11.900 | 26.000 | 26.235 | 23.790 | 20.254 | 28.197 | 23.941 |
| PIP | 0.631 | 0.090 | 0.105 | 0.152 | 0.302 | 0.082 | 0.131 |
| DETA | 38.430 | 54.672 | 54.260 | 52.317 | 46.643 | 55.162 | 53.334 |
| AEEA | 1.358 | 1.820 | 1.991 | 2.249 | 2.223 | 1.878 | 2.190 |
| AEP | 1.003 | 0.502 | 0.388 | 0.389 | 0.514 | 0.325 | 0.363 |
| HEP | 0.000 | 0.000 | 0.000 | 0.000 | 0.000 | 0.000 | 0.000 |
| TAEA | 2.102 | 1.571 | 1.456 | 1.611 | 1.878 | 1.195 | 1.609 |
| l-TETA | 12.373 | 7.704 | 7.909 | 9.027 | 10.859 | 6.705 | 8.957 |
| DAEP | 0.594 | 0.245 | 0.133 | 0.114 | 0.191 | 0.060 | 0.105 |
| PEEDA | 0.162 | 0.053 | 0.083 | 0.108 | 0.084 | 0.049 | 0.099 |
| DPE | 0.460 | 0.106 | 0.143 | 0.171 | 0.269 | 0.122 | 0.180 |
| AE-TAEA | 3.435 | 0.748 | 0.777 | 1.110 | 2.057 | 0.628 | 1.062 |
| l-TEPA | 5.957 | 0.976 | 1.117 | 1.577 | 3.217 | 0.791 | 1.486 |
| AE-DAEP | 0.280 | 0.045 | 0.028 | 0.041 | 0.083 | 0.000 | 0.032 |
| AE-PEEDA | 0.131 | 0.151 | 0.102 | 0.121 | 0.043 | 0.195 | 0.055 |

TABLE IX-continued

| | | | | | | | |
|---|---|---|---|---|---|---|---|
| iAE-PEEDA | 0.000 | 0.000 | 0.000 | 0.000 | 0.000 | 0.000 | 0.000 |
| AE-DPE | 0.088 | 0.000 | 0.000 | 0.034 | 0.272 | 0.000 | 0.000 |
| BPEA | 0.296 | 0.000 | 0.000 | 0.052 | 0.156 | 0.000 | 0.047 |
| Others | 11.413 | 2.165 | 1.873 | 2.601 | 4.845 | 1.692 | 2.559 |
| MEA Conversion, % | 67.96 | 30.21 | 29.38 | 35.76 | 45.44 | 24.03 | 35.94 |
| DETA Converison, % | 38.66 | 13.00 | 13.42 | 16.25 | 25.48 | 11.90 | 15.05 |
| Acyclic(N4), % | 92.24 | 95.80 | 96.29 | 96.42 | 95.89 | 97.14 | 96.48 |
| Acyclic(N5), % | 92.18 | 89.71 | 93.54 | 91.50 | 90.44 | 87.86 | 94.96 |
| Σ(N5)/Σ(N4), weight ratio | 0.64 | 0.19 | 0.20 | 0.26 | 0.43 | 0.19 | 0.24 |
| Acyclic(N4)/cyclic (< = N4), weight ratio | 5.07 | 9.28 | 10.96 | 11.35 | 9.35 | 12.35 | 12.00 |

TABLE X

| | Example No. | | | | | | | |
|---|---|---|---|---|---|---|---|---|
| | 119 | 120 | 121 | 122 | 123 | 124 | 125 | 126 |
| Composition Type | J | J | J | J | J | J | J | J |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.1 | 259.9 | 270.4 | 250 | 250 | 285.4 | 274.9 | 270.4 |
| Time on organics, hrs. | 4 | 24 | 28 | 47 | 72 | 96 | 100 | 120 |
| Duration of run, hrs. | 2 | 2 | 2 | 2 | 2 | 2 | 2 | 2 |
| MEA SV, gmol/hr/kgcat | 6.18 | 2.34 | 5.82 | 5.84 | 5.69 | 5.51 | 5.75 | 5.84 |
| DETA/MEA mole ratio | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 0.917 | 1.897 | 2.108 | 0.590 | 0.434 | 1.245 | 2.140 | 1.671 |
| MEA | 25.662 | 20.472 | 16.778 | 28.012 | 27.367 | 22.431 | 16.450 | 20.118 |
| PIP | 0.380 | 0.881 | 1.077 | 0.268 | 0.212 | 0.674 | 1.189 | 0.858 |
| DETA | 50.521 | 43.321 | 39.423 | 52.720 | 54.768 | 47.275 | 40.189 | 45.395 |
| AEEA | 2.344 | 2.643 | 1.892 | 2.035 | 2.217 | 2.374 | 1.773 | 2.194 |
| AEP | 0.461 | 0.807 | 1.116 | 0.369 | 0.357 | 0.675 | 1.147 | 0.885 |
| HEP | 0.000 | 0.000 | 0.000 | 0.000 | 0.000 | 0.000 | 0.000 | 0.000 |
| TAEA | 1.220 | 1.437 | 1.468 | 1.065 | 1.114 | 1.421 | 1.395 | 1.422 |
| l-TETA | 9.448 | 11.215 | 12.082 | 7.243 | 7.568 | 10.105 | 11.100 | 10.492 |
| DAEP | 0.115 | 0.274 | 0.481 | 0.069 | 0.062 | 0.210 | 0.438 | 0.310 |
| PEEDA | 0.063 | 0.175 | 0.071 | 0.039 | 0.033 | 0.056 | 0.067 | 0.060 |
| DPE | 0.116 | 0.171 | 0.245 | 0.071 | 0.076 | 0.182 | 0.299 | 0.250 |
| AE-TAEA | 1.057 | 1.803 | 2.308 | 0.672 | 0.602 | 1.534 | 2.154 | 1.795 |
| l-TEPA | 2.317 | 4.207 | 5.775 | 1.422 | 1.227 | 3.460 | 5.412 | 4.306 |
| AE-DAEP | 0.039 | 0.195 | 0.407 | 0.000 | 0.029 | 0.142 | 0.610 | 0.314 |
| AE-PEEDA | 0.000 | 0.037 | 0.039 | 0.000 | 0.000 | 0.000 | 0.119 | 0.043 |
| iAE-PEEDA | 0.000 | 0.000 | 0.000 | 0.000 | 0.000 | 0.000 | 0.000 | 0.000 |
| AE-DPE | 0.000 | 0.000 | 0.042 | 0.000 | 0.000 | 0.000 | 0.184 | 0.112 |
| BPEA | 0.141 | 0.281 | 0.355 | 0.082 | 0.065 | 0.187 | 0.205 | 0.132 |
| Others | 1.669 | 3.555 | 5.886 | 1.375 | 1.291 | 3.662 | 7.822 | 4.954 |
| MEA Conversion, % | 30.62 | 43.66 | 53.48 | 23.36 | 26.31 | 39.42 | 55.00 | 45.87 |
| DETA Converison, % | 19.04 | 29.32 | 35.21 | 14.49 | 12.58 | 24.32 | 34.91 | 27.60 |
| Acyclic(N4), % | 97.30 | 95.31 | 94.43 | 97.87 | 98.05 | 96.24 | 93.94 | 95.04 |
| Acyclic(N5), % | 94.89 | 92.10 | 90.54 | 96.19 | 95.07 | 93.80 | 87.10 | 90.99 |
| Σ(N5)/Σ(N4), weight ratio | 0.32 | 0.49 | 0.62 | 0.25 | 0.21 | 0.44 | 0.65 | 0.53 |
| Acyclic(N4)/cyclic (< = N4), weight ratio | 9.37 | 5.47 | 4.52 | 10.14 | 11.70 | 6.40 | 3.97 | 5.03 |

| | Example No. | | | | | | |
|---|---|---|---|---|---|---|---|
| | 127 | 128 | 129 | 130 | 131 | 132 | 133 |
| Composition Type | J | J | J | J | J | J | J |
| Composition weight, gm | 50 | 50 | 50 | 50 | 50 | 50 | 50 |
| Pressure, psig | 600 | 600 | 600 | 600 | 600 | 600 | 600 |
| Temperature, °C. | 280.5 | 250.3 | 255.6 | 260.5 | 270.5 | 250.4 | 260.4 |
| Time on organics, hrs. | 124 | 143 | 148 | 168 | 172 | 191 | 196 |
| Duration of run, hrs. | 2 | 2 | 2 | 2 | 2 | 2 | 2 |
| MEA SV, gmol/hr/kgcat | 5.73 | 5.72 | 6.20 | 5.68 | 6.10 | 5.61 | 6.22 |
| DETA/MEA mole ratio | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 |
| Crude product composition, wt. % | | | | | | | |
| EDA | 2.735 | 0.568 | 0.601 | 0.717 | 1.279 | 0.432 | 0.659 |
| MEA | 12.411 | 27.232 | 27.065 | 22.943 | 20.079 | 28.096 | 24.621 |
| PIP | 1.490 | 0.215 | 0.248 | 0.334 | 0.685 | 0.190 | 0.305 |
| DETA | 37.922 | 54.809 | 54.903 | 54.289 | 45.849 | 56.154 | 54.216 |
| AEEA | 1.405 | 1.865 | 2.067 | 2.397 | 2.218 | 1.939 | 2.262 |
| AEP | 1.698 | 0.495 | 0.410 | 0.506 | 0.739 | 0.377 | 0.454 |
| HEP | 0.000 | 0.000 | 0.000 | 0.000 | 0.000 | 0.000 | 0.000 |
| TAEA | 1.542 | 1.241 | 1.085 | 1.426 | 1.382 | 0.995 | 1.248 |
| l-TETA | 11.616 | 7.018 | 6.914 | 8.559 | 9.775 | 6.269 | 7.933 |
| DAEP | 0.808 | 0.201 | 0.100 | 0.168 | 0.247 | 0.071 | 0.112 |
| PEEDA | 0.135 | 0.041 | 0.070 | 0.067 | 0.081 | 0.058 | 0.082 |
| DPE | 0.107 | 0.098 | 0.111 | 0.138 | 0.256 | 0.116 | 0.155 |

TABLE X-continued

| | | | | | | | |
|---|---|---|---|---|---|---|---|
| AE-TAEA | 2.349 | 0.572 | 0.555 | 0.788 | 1.643 | 0.476 | 0.783 |
| 1-TEPA | 6.191 | 0.960 | 1.063 | 1.605 | 3.662 | 0.771 | 1.561 |
| AE-DAEP | 0.399 | 0.051 | 0.032 | 0.048 | 0.231 | 0.000 | 0.049 |
| AE-PEEDA | 0.254 | 0.060 | 0.172 | 0.043 | 0.121 | 0.267 | 0.041 |
| iAE-PEEDA | 0.000 | 0.000 | 0.000 | 0.000 | 0.000 | 0.000 | 0.000 |
| AE-DPE | 0.044 | 0.000 | 0.000 | 0.000 | 0.398 | 0.000 | 0.000 |
| BPEA | 0.238 | 0.000 | 0.000 | 0.093 | 0.146 | 0.000 | 0.100 |
| Others | 11.756 | 2.205 | 1.668 | 2.622 | 6.639 | 1.610 | 2.481 |
| MEA Conversion, % | 66.59 | 26.89 | 26.88 | 38.41 | 46.08 | 24.52 | 33.90 |
| DETA Converison, % | 39.49 | 12.77 | 12.07 | 13.61 | 27.01 | 10.57 | 13.72 |
| Acyclic(N4), % | 92.59 | 96.03 | 96.59 | 96.39 | 95.01 | 96.71 | 96.32 |
| Acyclic(N5), % | 90.10 | 93.16 | 88.76 | 92.80 | 85.52 | 82.30 | 92.41 |
| $\Sigma(N5)/\Sigma(N4)$, weight ratio | 0.66 | 0.19 | 0.22 | 0.24 | 0.52 | 0.20 | 0.26 |
| Acyclic(N4)/cyclic (< = N4), weight ratio | 3.10 | 7.85 | 8.50 | 8.21 | 5.55 | 8.91 | 8.26 |

TABLE XI

| | Example No. | | | | | | | |
|---|---|---|---|---|---|---|---|---|
| | 134 | 135 | 136 | 137 | 138 | 139 | 140 | 141 |
| Composition Type | K | K | K | K | K | K | K | K |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.1 | 259.9 | 270.4 | 250 | 250 | 285.4 | 274.9 | 270.4 |
| Time on organics, hrs. | 4 | 24 | 28 | 47 | 72 | 986 | 100 | 120 |
| Duration of run, hrs. | 2 | 2 | 2 | 2 | 2 | 2 | 2 | 2 |
| MEA SV, gmol/hr/kgcat | 5.91 | 5.22 | 5.79 | 5.68 | 5.01 | 4.83 | 3.20 | 4.69 |
| DETA/MEA mole ratio | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.242 | 1.425 | 2.314 | 0.692 | 0.693 | 1.556 | 2.532 | 2.046 |
| MEA | 24.360 | 19.503 | 13.469 | 26.303 | 26.975 | 19.666 | 10.987 | 15.532 |
| PIP | 0.265 | 0.346 | 0.627 | 0.143 | 0.124 | 0.340 | 0.644 | 0.486 |
| DETA | 47.368 | 41.906 | 36.625 | 50.994 | 52.751 | 43.552 | 35.351 | 40.568 |
| AEEA | 2.338 | 2.228 | 1.775 | 2.093 | 2.109 | 2.236 | 1.595 | 2.030 |
| AEP | 0.444 | 0.513 | 0.933 | 0.336 | 0.320 | 0.511 | 0.884 | 0.729 |
| HEP | 0.000 | 0.000 | 0.000 | 0.000 | 0.000 | 0.000 | 0.000 | 0.000 |
| TAEA | 1.585 | 1.779 | 1.946 | 1.465 | 1.421 | 1.853 | 1.907 | 1.979 |
| 1-TETA | 10.818 | 11.971 | 13.853 | 8.981 | 8.541 | 11.616 | 12.837 | 13.039 |
| DAEP | 0.137 | 0.201 | 0.508 | 0.073 | 0.066 | 0.184 | 0.434 | 0.315 |
| PEEDA | 0.048 | 0.063 | 0.083 | 0.041 | 0.045 | 0.070 | 0.105 | 0.089 |
| DPE | 0.147 | 0.053 | 0.357 | 0.113 | 0.106 | 0.275 | 0.379 | 0.354 |
| AE-TAEA | 1.536 | 2.197 | 3.601 | 1.105 | 0.931 | 2.462 | 3.448 | 3.044 |
| 1-TEPA | 2.585 | 3.750 | 6.842 | 1.710 | 1.407 | 4.084 | 62.36 | 5.278 |
| AE-DAEP | 0.039 | 0.075 | 0.609 | 0.000 | 0.000 | 0.281 | 0.507 | 0.443 |
| AE-PEEDA | 0.000 | 0.041 | 0.143 | 0.000 | 0.040 | 0.099 | 0.122 | 0.116 |
| iAE-PEEDA | 0.000 | 0.000 | 0.000 | 0.000 | 0.000 | 0.000 | 0.000 | 0.000 |
| AE-DPE | 0.000 | 0.108 | 0.388 | 0.000 | 0.000 | 0.319 | 0.127 | 0.215 |
| BPEA | 0.201 | 0.347 | 0.305 | 0.127 | 0.079 | 0.340 | 0.272 | 0.259 |
| Others | 2.750 | 3.474 | 9.064 | 1.636 | 1.564 | 5.577 | 8.946 | 7.208 |
| MEA Conversion, % | 33.99 | 44.31 | 63.83 | 28.21 | 27.29 | 47.03 | 68.48 | 58.05 |
| DETA Converison, % | 23.91 | 29.07 | 41.70 | 17.49 | 15.71 | 30.46 | 39.88 | 35.04 |
| Acyclic(N4), % | 97.38 | 97.73 | 94.33 | 97.86 | 97.84 | 96.20 | 94.12 | 95.18 |
| Acyclic(N5), % | 94.47 | 91.20 | 87.83 | 95.68 | 95.12 | 86.28 | 90.39 | 88.94 |
| $\Sigma(N5)/\Sigma(N4)$, weight ratio | 0.34 | 0.46 | 0.70 | 0.27 | 0.24 | 0.54 | 0.68 | 0.59 |
| Acyclic(N4)/cyclic (< = N4), weight ratio | 11.89 | 11.66 | 6.29 | 14.74 | 15.00 | 9.73 | 6.02 | 7.59 |

| | Example No. | | | | | | |
|---|---|---|---|---|---|---|---|
| | 142 | 143 | 144 | 145 | 146 | 147 | 147 |
| Composition Type | K | K | K | K | K | K | K |
| Composition weight, gm | 50 | 50 | 50 | 50 | 50 | 50 | 50 |
| Pressure, psig | 600 | 600 | 600 | 600 | 600 | 600 | 600 |
| Temperature, °C. | 280.5 | 250.3 | 255.6 | 260.5 | 270.5 | 250.4 | 260.4 |
| Time on organics, hrs. | 124 | 143 | 148 | 168 | 172 | 191 | 196 |
| Duration of run, hrs. | 2 | 2 | 2 | 2 | 2 | 2 | 2 |
| MEA SV, gmol/hr/kgcat | 4.67 | 4.55 | 4.85 | 5.47 | 5.78 | 5.58 | 5.91 |
| DETA/MEA mole ratio | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 |
| Crude product composition, wt. % | | | | | | | |
| EDA | 2.610 | 0.781 | 0.770 | 0.851 | 1.497 | 0.588 | 1.026 |
| MEA | 8.187 | 25.538 | 22.350 | 20.873 | 16.503 | 25.282 | 24.673 |
| PIP | 0.714 | 0.126 | 0.140 | 0.170 | 0.328 | 0.089 | 0.177 |
| DETA | 37.477 | 52.133 | 52.645 | 51.089 | 44.349 | 55.299 | 51.223 |
| AEEA | 1.250 | 2.040 | 2.312 | 2.326 | 2.193 | 2.078 | 2.224 |
| AEP | 1.333 | 0.426 | 0.428 | 0.436 | 0.591 | 0.356 | 0.443 |
| HEP | 0.000 | 0.000 | 0.000 | 0.000 | 0.000 | 0.000 | 0.000 |
| TAEA | 2.217 | 1.593 | 1.735 | 1.861 | 1.981 | 1.469 | 1.571 |

TABLE XI-continued

| | | | | | | | |
|---|---|---|---|---|---|---|---|
| 1-TETA | 13.746 | 8.770 | 9.724 | 10.271 | 11.974 | 8.218 | 9.145 |
| DAEP | 0.805 | 0.153 | 0.159 | 0.161 | 0.253 | 0.106 | 0.115 |
| PEEDA | 0.181 | 0.049 | 0.112 | 0.117 | 0.133 | 0.097 | 0.112 |
| DPE | 0.142 | 0.140 | 0.171 | 0.192 | 0.320 | 0.142 | 0.165 |
| AE-TAEA | 3.487 | 1.025 | 1.128 | 1.380 | 2.468 | 0.743 | 1.139 |
| 1-TEPA | 6.468 | 1.452 | 1.623 | 2.028 | 4.244 | 0.949 | 1.722 |
| AE-DAEP | 0.547 | 0.053 | 0.044 | 0.047 | 0.312 | 0.000 | 0.000 |
| AE-PEEDA | 0.102 | 0.079 | 0.041 | 0.037 | 0.094 | 0.106 | 0.000 |
| iAE-PEEDA | 0.000 | 0.000 | 0.000 | 0.000 | 0.000 | 0.000 | 0.000 |
| AE-DPE | 0.099 | 0.000 | 0.000 | 0.000 | 0.050 | 0.000 | 0.000 |
| BPEA | 0.272 | 0.000 | 0.100 | 0.100 | 0.197 | 0.000 | 0.030 |
| Others | 12.055 | 2.433 | 2.776 | 3.266 | 6.788 | 1.812 | 2.887 |
| MEA Conversion, % | 77.82 | 31.14 | 39.18 | 43.37 | 55.46 | 32.14 | 33.50 |
| DETA Converison, % | 39.81 | 16.67 | 15.95 | 17.84 | 29.04 | 12.01 | 18.16 |
| Acyclic(N4), % | 93.39 | 96.78 | 96.26 | 96.26 | 95.17 | 96.54 | 96.46 |
| Acyclic(N5), % | 90.68 | 94.89 | 93.64 | 94.69 | 91.17 | 94.09 | 98.95 |
| Σ(N5)/Σ(N4), weight ratio | 0.64 | 0.24 | 0.24 | 0.28 | 0.50 | 0.17 | 0.26 |
| Acyclic(N4)/cyclic (< = N4), weight ratio | 5.02 | 11.55 | 11.30 | 11.24 | 8.57 | 12.22 | 10.56 |

TABLE XII

| | Example No. | | | | | | | | | | |
|---|---|---|---|---|---|---|---|---|---|---|---|
| | 149 | 150 | 151 | 152 | 153 | 154 | 155 | 156 | 157 | 158 | 159 |
| Composition Type | L | L | L | L | L | L | L | L | L | L | L |
| Composition weight, gm | 50 | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 | 600 |
| Temperature, °C. | 249.3 | 259.6 | 270.3 | 264.7 | 274.8 | 280.3 | 285.1 | 260.4 | 270.3 | 250.7 | 250.8 |
| Time on organics, hrs. | 4 | 24 | 28 | 48 | 52 | 72 | 76 | 86 | 100 | 119.7 | 144.5 |
| Duration of run, hrs. | 2 | 2 | 2 | 2 | 2 | 2 | 2 | 2 | 2 | 2 | 2 |
| MEA SV, gmol/hr/kgcat | 6.40 | 6.33 | 6.28 | 5.72 | 6.02 | 5.58 | 5.65 | 6.24 | 6.17 | 6.94 | 5.93 |
| DETA/MEA mole ratio | 0.99 | 0.99 | 0.99 | 0.99 | 0.99 | 0.99 | 0.99 | 0.99 | 0.99 | 0.99 | 0.99 |
| NH₃/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 0.770 | 0.980 | 1.583 | 1.111 | 1.832 | 2.142 | 3.301 | 0.774 | 1.198 | 0.345 | 0.350 |
| MEA | 25.827 | 23.440 | 17.219 | 22.571 | 16.310 | 16.564 | 10.045 | 27.643 | 21.820 | 30.552 | 30.853 |
| PIP | 0.276 | 0.393 | 0.662 | 0.422 | 0.751 | 0.950 | 1.442 | 0.265 | 0.454 | 0.111 | 0.096 |
| DETA | 51.636 | 48.836 | 42.304 | 48.278 | 40.898 | 42.099 | 35.503 | 52.572 | 47.132 | 55.797 | 55.617 |
| AEEA | 2.334 | 2.504 | 2.372 | 2.475 | 2.126 | 1.936 | 1.055 | 2.172 | 2.317 | 1.696 | 1.611 |
| AEP | 0.412 | 0.494 | 0.838 | 0.522 | 0.865 | 0.963 | 1.612 | 0.359 | 0.551 | 0.258 | 0.247 |
| HEP | 0.000 | 0.000 | 0.000 | 0.000 | 0.000 | 0.000 | 0.000 | 0.000 | 0.000 | 0.000 | 0.000 |
| TAEA | 1.110 | 1.332 | 1.599 | 1.416 | 1.525 | 1.379 | 1.308 | 1.011 | 1.348 | 0.717 | 0.639 |
| 1-TETA | 8.696 | 10.460 | 12.736 | 10.690 | 12.202 | 11.061 | 11.624 | 7.027 | 9.767 | 4.893 | 4.363 |
| DAEP | 0.101 | 0.165 | 0.378 | 0.173 | 0.369 | 0.370 | 0.792 | 0.081 | 0.178 | 0.044 | 0.039 |
| PEEDA | 0.489 | 0.055 | 0.252 | 0.693 | 0.263 | 0.286 | 0.651 | 0.025 | 0.122 | 0.023 | 0.032 |
| DPE | 0.112 | 0.134 | 0.073 | 0.039 | 0.086 | 0.085 | 0.110 | 0.079 | 0.180 | 0.004 | 0.052 |
| AE-TAEA | 0.841 | 1.303 | 2.375 | 1.359 | 2.466 | 2.153 | 2.771 | 0.689 | 1.489 | 0.308 | 0.099 |
| 1-TEPA | 1.854 | 3.003 | 5.582 | 3.165 | 5.909 | 5.377 | 7.397 | 1.584 | 3.350 | 0.591 | 0.239 |
| AE-DAEP | 0.000 | 0.051 | 0.359 | 0.070 | 0.646 | 0.658 | 0.827 | 0.000 | 0.171 | 0.000 | 0.342 |
| AE-PEEDA | 0.000 | 0.000 | 0.040 | 0.031 | 0.109 | 0.115 | 0.423 | 0.032 | 0.042 | 0.000 | 0.000 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.112 | 0.049 | 0.000 | 0.057 | 0.476 | 0.079 | 0.000 | 0.000 | 0.000 | 0.045 |
| BPEA | 0.093 | 0.263 | 0.619 | 0.150 | 0.427 | 0.359 | 0.296 | 0.036 | 0.063 | 0.000 | 0.000 |
| Others | 1.692 | 2.457 | 4.961 | 2.959 | 6.639 | 6.450 | 12.385 | 2.004 | 3.510 | 1.034 | 0.830 |
| MEA Conversion, % | 29.54 | 36.72 | 53.44 | 38.82 | 55.78 | 55.02 | 72.73 | 24.68 | 39.81 | 16.04 | 14.31 |
| DETA Conversion, % | 16.50 | 21.84 | 32.20 | 22.43 | 34.26 | 32.23 | 42.86 | 15.08 | 22.93 | 9.10 | 8.43 |
| Acyclic(N4), % | 97.38 | 97.07 | 95.31 | 97.77 | 95.01 | 94.37 | 89.26 | 97.73 | 95.84 | 98.71 | 97.58 |
| Acyclic(N5), % | 96.65 | 90.95 | 88.16 | 94.71 | 87.09 | 82.38 | 86.19 | 97.08 | 94.57 | 100.00 | 46.54 |
| Σ(N5)/Σ(N4), weight ratio | 0.27 | 0.38 | 0.60 | 0.38 | 0.66 | 0.69 | 0.81 | 0.28 | 0.44 | 0.15 | 0.14 |
| Acyclic(N4)/cyclic (< = N4), weight ratio | 10.30 | 9.49 | 6.49 | 9.91 | 5.87 | 4.68 | 2.80 | 9.90 | 7.47 | 12.67 | 10.70 |

TABLE XIII

| Example No. | 160 | 161 | 162 | 163 | 164 | 165 | 166 | 167 | 168 | 169 |
|---|---|---|---|---|---|---|---|---|---|---|
| Composition Type | M | M | M | M | M | M | M | M | M | M |
| Composition weight, gm | 50 | 50 | 50 | 50 | 50 | 50 | 50 | 50 | 50 | 50 |
| Pressure, psig | 600 | 600 | 600 | 400 | 600 | 600 | 600 | 600 | 600 | 600 |
| Temperature, °C. | 249.3 | 259.6 | 270.3 | 264.7 | 274.8 | 280.3 | 285.1 | 270.3 | 250.7 | 250.8 |
| Time on organics, hrs. | 4 | 24 | 28 | 48 | 52 | 72 | 76 | 100 | 119.7 | 144.5 |
| Duration of run, hrs. | 2 | 2 | 2 | 2 | 2 | 2 | 2 | 2 | 2 | 2 |
| MEA SV, gmol/hr/kgcat | 6.17 | 5.95 | 5.82 | 5.54 | 5.88 | 4.57 | 6.15 | 6.07 | 7.05 | 5.82 |
| DETA/MEA mole ratio | 0.99 | 0.99 | 0.99 | 0.99 | 0.99 | 0.99 | 0.99 | 0.99 | 0.99 | 0.99 |
| NH₃/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.893 | 1.185 | 1.874 | 1.443 | 2.387 | 2.639 | 3.678 | 1.556 | 0.481 | 0.515 |
| MEA | 23.997 | 21.165 | 15.053 | 20.703 | 14.059 | 13.349 | 8.387 | 18.730 | 28.844 | 29.482 |

TABLE XIII-continued

| Example No. | 160 | 161 | 162 | 163 | 164 | 165 | 166 | 167 | 168 | 169 |
|---|---|---|---|---|---|---|---|---|---|---|
| PIP | 0.250 | 0.368 | 0.597 | 0.409 | 0.727 | 0.812 | 1.108 | 0.435 | 0.112 | 0.093 |
| DETA | 50.182 | 46.524 | 39.414 | 45.397 | 38.993 | 39.116 | 35.238 | 42.781 | 53.913 | 53.627 |
| AEEA | 2.411 | 2.498 | 2.085 | 2.340 | 1.699 | 1.499 | 0.681 | 2.101 | 1.876 | 1.810 |
| AEP | 0.422 | 0.510 | 0.810 | 0.527 | 0.904 | 1.012 | 1.488 | 0.535 | 0.274 | 0.244 |
| HEP | 0.000 | 0.000 | 0.000 | 0.000 | 0.000 | 0.000 | 0.000 | 0.000 | 0.000 | 0.000 |
| TAEA | 1.425 | 1.775 | 1.846 | 1.795 | 1.800 | 1.721 | 1.514 | 1.777 | 1.179 | 1.018 |
| l-TETA | 10.191 | 11.986 | 13.100 | 11.628 | 12.524 | 12.091 | 11.574 | 10.990 | 6.600 | 5.769 |
| DAEP | 0.109 | 0.185 | 0.375 | 0.187 | 0.419 | 0.473 | 0.929 | 0.206 | 0.053 | 0.044 |
| PEEDA | 0.063 | 0.051 | 0.228 | 0.118 | 0.266 | 0.306 | 0.601 | 0.128 | 0.026 | 0.066 |
| DPE | 0.125 | 0.171 | 0.107 | 0.060 | 0.110 | 0.107 | 0.462 | 0.286 | 0.080 | 0.066 |
| AE-TAEA | 1.294 | 2.017 | 3.232 | 2.258 | 3.432 | 3.203 | 3.391 | 2.731 | 0.694 | 0.490 |
| l-TEPA | 2.267 | 3.609 | 6.173 | 3.897 | 6.441 | 6.147 | 7.234 | 4.636 | 1.042 | 0.691 |
| AE-DAEP | 0.031 | 0.048 | 0.524 | 0.080 | 0.621 | 0.625 | 0.927 | 0.399 | 0.000 | 0.000 |
| AE-PEEDA | 0.000 | 0.033 | 0.108 | 0.047 | 0.094 | 0.111 | 0.467 | 0.157 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.000 | 0.236 | 0.000 | 0.224 | 0.275 | 0.049 | 0.299 | 0.000 | 0.000 |
| BPEA | 0.045 | 0.106 | 0.552 | 0.282 | 0.617 | 0.594 | 0.195 | 0.235 | 0.000 | 0.000 |
| Others | 1.906 | 3.042 | 6.857 | 3.249 | 7.904 | 8.181 | 13.108 | 5.468 | 1.100 | 0.978 |
| MEA Conversion, % | 34.77 | 42.76 | 59.22 | 43.57 | 62.03 | 63.61 | 77.16 | 48.81 | 21.06 | 17.89 |
| DETA Conversion, % | 19.07 | 25.41 | 36.70 | 26.65 | 37.57 | 36.79 | 43.13 | 30.69 | 12.53 | 11.46 |
| Acyclic(N4), % | 97.49 | 97.11 | 95.45 | 97.33 | 94.73 | 93.96 | 86.78 | 95.35 | 97.98 | 97.44 |
| Acyclic(N5), % | 97.89 | 96.76 | 86.87 | 93.75 | 86.37 | 85.33 | 86.62 | 87.08 | 100.00 | 100.00 |
| Σ(N5)/Σ(N4), weight ratio | 0.30 | 0.41 | 0.69 | 0.47 | 0.75 | 0.74 | 0.81 | 0.63 | 0.21 | 0.16 |
| Acyclic(N4)/cyclic (<=N4), weight ratio | 11.96 | 10.68 | 7.04 | 10.28 | 5.89 | 5.09 | 2.85 | 8.01 | 14.23 | 13.14 |

TABLE XIV

| Comparative Example No. | 170 | 171 | 172 | 173 | 174 | 175 | 176 | 177 | 178 |
|---|---|---|---|---|---|---|---|---|---|
| Composition Type | N | N | N | N | N | N | N | N | N |
| Composition weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 251 | 250.5 | 260.7 | 265.6 | 270.4 | 275.8 | 280.5 | 255.8 | 245.6 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 3.47 | 3.80 | 3.91 | 3.78 | 4.01 | 3.87 | 4.12 | 3.34 | 3.15 |
| DETA/MEA mole ratio | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 2.846 | 1.526 | 2.032 | 1.886 | 2.080 | 2.055 | 2.349 | 0.725 | 0.430 |
| MEA | 20.117 | 22.677 | 18.757 | 16.307 | 13.974 | 13.175 | 11.612 | 25.948 | 29.403 |
| PIP | 0.388 | 0.256 | 0.499 | 0.640 | 0.773 | 0.847 | 0.969 | 0.218 | 0.102 |
| DETA | 38.752 | 46.030 | 41.118 | 41.094 | 35.948 | 37.509 | 34.665 | 52.792 | 56.722 |
| AEEA | 2.423 | 3.036 | 3.076 | 3.058 | 2.464 | 2.253 | 1.745 | 3.079 | 2.412 |
| AEP | 0.532 | 0.351 | 0.611 | 0.804 | 0.961 | 1.106 | 1.326 | 0.327 | 0.250 |
| HEP | 0.000 | 0.000 | 0.000 | 0.000 | 0.000 | 0.000 | 0.000 | 0.000 | 0.000 |
| TAEA | 0.913 | 0.960 | 1.193 | 1.429 | 1.379 | 1.405 | 1.366 | 0.793 | 0.480 |
| l-TETA | 6.883 | 7.323 | 9.136 | 10.360 | 9.961 | 9.612 | 9.046 | 5.680 | 3.493 |
| DAEP | 0.130 | 0.038 | 0.254 | 0.343 | 0.479 | 0.517 | 0.769 | 0.100 | 0.049 |
| PEEDA | 0.188 | 0.076 | 0.217 | 0.124 | 0.154 | 0.084 | 0.662 | 0.074 | 0.036 |
| DPE | 0.150 | 0.132 | 0.325 | 0.319 | 0.397 | 0.361 | 0.120 | 0.153 | 0.089 |
| AE-TAEA | 0.216 | 0.137 | 1.821 | 0.185 | 0.244 | 0.207 | 2.472 | 0.625 | 0.349 |
| l-TEPA | 0.296 | 2.808 | 4.728 | 6.414 | 7.260 | 6.994 | 7.086 | 2.162 | 0.887 |
| AE-DAEP | 0.731 | 0.413 | 0.156 | 0.157 | 0.197 | 0.176 | 1.016 | 0.226 | 0.078 |
| AE-PEEDA | 0.175 | 0.237 | 0.215 | 0.263 | 0.406 | 0.407 | 0.313 | 0.082 | 0.031 |
| iAE-PEEDA | 0.000 | 0.000 | 0.000 | 0.000 | 0.000 | 0.000 | 0.000 | 0.000 | 0.000 |
| AE-DPE | 0.291 | 0.147 | 0.259 | 0.254 | 0.453 | 0.383 | 0.175 | 0.036 | 0.138 |
| BPEA | 0.199 | 0.113 | 0.345 | 0.433 | 0.745 | 0.091 | 0.611 | 0.033 | 0.000 |
| Others | 16.400 | 7.123 | 10.349 | 11.322 | 15.766 | 15.360 | 16.327 | 3.878 | 2.051 |
| MEA Conversion, % | 43.51 | 37.03 | 49.65 | 56.66 | 62.55 | 64.22 | 68.78 | 30.04 | 19.95 |
| DETA Conversion, % | 35.49 | 24.23 | 34.57 | 35.26 | 42.89 | 39.62 | 44.75 | 15.62 | 8.46 |
| Acyclic(N4), % | 94.31 | 97.10 | 92.83 | 93.73 | 91.66 | 91.95 | 87.02 | 95.16 | 95.77 |
| Acyclic(N5), % | 26.85 | 76.39 | 87.03 | 85.62 | 80.62 | 87.19 | 81.87 | 88.03 | 83.29 |
| Σ(N5)/Σ(N4), weight ratio | 0.23 | 0.45 | 0.67 | 0.61 | 0.75 | 0.68 | 0.97 | 0.46 | 0.35 |
| Acyclic(N4)/cyclic (<=N4), weight ratio | 5.60 | 9.69 | 5.41 | 5.27 | 4.09 | 3.77 | 2.70 | 7.39 | 7.51 |

TABLE XV

| Example No. | 179 | 180 | 181 | 182 | 183 | 184 | 185 | 186 | 187 | 188 |
|---|---|---|---|---|---|---|---|---|---|---|
| Composition Type | O | O | O | O | O | O | O | O | O | O |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.5 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 72 | 97 | 116.3 | 138 |

TABLE XV-continued

| Example No. | 179 | 180 | 181 | 182 | 183 | 184 | 185 | 186 | 187 | 188 |
|---|---|---|---|---|---|---|---|---|---|---|
| Duration of run, hrs. | 2 | 2 | 2 | 2 | 2 | 2 | 2 | 2 | 2 | 2 |
| MEA SV, gmol/hr/kgcat | 5.54 | 5.44 | 6.26 | 6.35 | 6.68 | 6.95 | 6.07 | 5.74 | 6.22 | 5.52 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.557 | 0.797 | 0.461 | 0.645 | 0.777 | 1.221 | 0.258 | 0.400 | 0.408 | 0.214 |
| MEA | 32.336 | 29.295 | 31.431 | 27.011 | 27.058 | 20.206 | 31.252 | 29.183 | 29.037 | 32.707 |
| PIP | 0.147 | 0.336 | 0.159 | 0.315 | 0.434 | 0.832 | 0.093 | 0.216 | 0.197 | 0.088 |
| DETA | 56.556 | 55.334 | 57.257 | 55.289 | 54.631 | 50.585 | 59.566 | 57.321 | 57.294 | 59.411 |
| AEEA | 2.101 | 2.829 | 2.340 | 2.851 | 2.944 | 2.743 | 2.003 | 2.673 | 2.620 | 1.871 |
| AEP | 0.307 | 0.366 | 0.271 | 0.435 | 0.440 | 0.778 | 0.285 | 0.332 | 0.318 | 0.272 |
| HEP | 0.000 | 0.000 | 0.000 | 0.000 | 0.000 | 0.000 | 0.000 | 0.000 | 0.000 | 0.000 |
| TAEA | 0.432 | 0.692 | 0.443 | 0.736 | 0.748 | 1.212 | 0.436 | 0.516 | 0.547 | 0.280 |
| l-TETA | 2.629 | 4.380 | 2.617 | 4.340 | 4.427 | 7.328 | 2.476 | 3.221 | 3.344 | 1.831 |
| DAEP | 0.162 | 0.122 | 0.053 | 0.087 | 0.088 | 0.243 | 0.039 | 0.054 | 0.055 | 0.074 |
| PEEDA | 0.052 | 0.024 | 0.046 | 0.028 | 0.021 | 0.247 | 0.029 | 0.027 | 0.030 | 0.025 |
| DPE | 0.000 | 0.064 | 0.078 | 0.068 | 0.075 | 0.145 | 0.031 | 0.045 | 0.039 | 0.000 |
| AE-TAEA | 0.082 | 0.270 | 0.095 | 0.335 | 0.461 | 1.255 | 0.092 | 0.152 | 0.245 | 0.060 |
| l-TEPA | 0.033 | 0.668 | 0.303 | 0.856 | 1.340 | 3.408 | 0.229 | 0.413 | 0.661 | 0.085 |
| AE-DAEP | 0.083 | 0.027 | 0.000 | 0.020 | 0.058 | 0.215 | 0.000 | 0.000 | 0.000 | 0.000 |
| AE-PEEDA | 0.055 | 0.000 | 0.000 | 0.000 | 0.000 | 0.025 | 0.075 | 0.161 | 0.184 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.106 | 0.000 | 0.000 | 0.000 | 0.000 | 0.087 | 0.000 | 0.000 | 0.000 | 0.118 |
| BPEA | 0.000 | 0.000 | 0.000 | 0.000 | 0.036 | 0.100 | 0.000 | 0.000 | 0.000 | 0.000 |
| Others | 1.554 | 1.558 | 1.509 | 1.685 | 2.059 | 3.632 | 1.368 | 1.728 | 1.572 | 0.679 |
| MEA Conversion, % | 11.54 | 20.03 | 14.00 | 24.93 | 25.58 | 44.77 | 15.58 | 20.02 | 20.56 | 10.86 |
| DETA Conversion, % | 8.29 | 10.46 | 7.13 | 8.91 | 10.93 | 18.03 | 4.61 | 6.87 | 7.07 | 4.01 |
| Acyclic(N4), % | 93.44 | 95.99 | 94.48 | 96.48 | 96.52 | 93.06 | 96.66 | 96.71 | 96.87 | 95.47 |
| Acyclic(N5), % | 32.06 | 97.13 | 100.00 | 98.26 | 94.89 | 91.56 | 80.95 | 77.80 | 83.06 | 55.28 |
| $\Sigma(N5)/\Sigma(N4)$, weight ratio | 0.11 | 0.18 | 0.12 | 0.23 | 0.34 | 0.55 | 0.13 | 0.18 | 0.27 | 0.11 |
| Acyclic(N4)/cyclic (<=N4), weight ratio | 4.57 | 5.54 | 5.02 | 5.42 | 4.87 | 3.80 | 6.08 | 5.53 | 6.06 | 4.58 |

TABLE XVI

| Comparative Example No. | 189 | 190 | 191 | 192 | 193 | 194 | 195 | 196 | 197 |
|---|---|---|---|---|---|---|---|---|---|
| Composition Type | P | P | P | P | P | P | P | P | P |
| Composition weight, gm | 50 | 50 | 50 | 50 | 50 | 50 | 50 | 50 | 50 |
| Pressure, psig | 600 | 600 | 600 | 400 | 600 | 600 | 600 | 600 | 600 |
| Temperature, °C. | 251 | 250.5 | 260.7 | 265.6 | 270.4 | 275.8 | 280.5 | 255.8 | 245.5 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 3.46 | 3.96 | 3.89 | 3.66 | 3.88 | 3.96 | 4.00 | 3.97 | 4.04 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. %. | | | | | | | | | |
| EDA | 0.569 | 0.369 | 0.606 | 0.790 | 0.904 | 1.370 | 1.436 | 0.353 | 0.165 |
| MEA | 22.906 | 25.594 | 20.285 | 17.926 | 14.593 | 14.303 | 12.427 | 26.475 | 30.271 |
| PIP | 0.366 | 0.218 | 0.401 | 0.561 | 0.667 | 1.037 | 1.090 | 0.220 | 0.079 |
| DETA | 50.355 | 54.133 | 48.370 | 47.753 | 41.854 | 42.262 | 40.213 | 53.453 | 59.022 |
| AEEA | 2.955 | 3.393 | 3.649 | 3.648 | 2.988 | 2.426 | 1.989 | 2.794 | 2.193 |
| AEP | 0.473 | 0.305 | 0.456 | 0.607 | 0.722 | 1.086 | 1.211 | 0.306 | 0.236 |
| HEP | 0.000 | 0.000 | 0.000 | 0.000 | 0.000 | 0.000 | 0.000 | 0.000 | 0.000 |
| TAEA | 1.254 | 1.114 | 1.436 | 1.582 | 1.518 | 1.586 | 1.556 | 0.732 | 0.447 |
| l-TETA | 7.783 | 6.913 | 9.002 | 9.975 | 9.612 | 10.518 | 10.362 | 4.586 | 2.655 |
| DAEP | 0.122 | 0.065 | 0.137 | 0.196 | 0.312 | 0.449 | 0.543 | 0.081 | 0.040 |
| PEEDA | 0.065 | 0.039 | 0.117 | 0.171 | 0.130 | 0.064 | 0.515 | 0.067 | 0.029 |
| DPE | 0.063 | 0.049 | 0.181 | 0.170 | 0.302 | 0.281 | 0.115 | 0.161 | 0.062 |
| AE-TAEA | 0.161 | 0.112 | 1.712 | 1.846 | 2.488 | 0.152 | 2.426 | 0.607 | 0.179 |
| l-TEPA | 2.457 | 1.842 | 3.712 | 4.439 | 5.404 | 6.285 | 6.578 | 1.410 | 0.198 |
| AE-DAEP | 0.059 | 0.063 | 0.165 | 0.212 | 0.623 | 0.154 | 0.685 | 0.248 | 0.065 |
| AE-PEEDA | 0.059 | 0.025 | 0.138 | 0.103 | 0.359 | 0.325 | 0.207 | 0.152 | 0.036 |
| iAE-PEEDA | 0.000 | 0.000 | 0.000 | 0.000 | 0.000 | 0.000 | 0.000 | 0.000 | 0.000 |
| AE-DPE | 0.044 | 0.028 | 0.236 | 0.276 | 0.341 | 0.169 | 0.351 | 0.184 | 0.138 |
| BPEA | 0.025 | 0.049 | 0.166 | 0.271 | 0.792 | 0.439 | 0.423 | 0.121 | 0.000 |
| Others | 3.746 | 2.581 | 5.592 | 4.546 | 10.542 | 10.867 | 9.666 | 4.479 | 1.866 |
| MEA Conversion, % | 36.31 | 30.93 | 45.92 | 51.83 | 60.98 | 61.53 | 66.10 | 28.20 | 17.97 |
| DETA Conversion, % | 17.00 | 13.40 | 23.56 | 23.94 | 33.65 | 32.63 | 34.97 | 14.06 | 5.18 |
| Acyclic(N4), % | 97.29 | 98.10 | 95.97 | 95.54 | 93.72 | 93.83 | 91.02 | 94.48 | 95.88 |
| Acyclic(N5), % | 93.26 | 92.16 | 88.46 | 87.92 | 78.84 | 85.42 | 84.36 | 74.04 | 61.21 |
| $\Sigma(N5)/\Sigma(N4)$, weight ratio | 0.30 | 0.25 | 0.56 | 0.59 | 0.84 | 0.58 | 0.81 | 0.48 | 0.19 |
| Acyclic(N4)/cyclic (<=N4), weight ratio | 8.28 | 11.82 | 8.06 | 6.76 | 5.21 | 4.14 | 3.42 | 6.35 | 6.89 |

TABLE XVII

| Comparative Example No. | 198 | 199 | 200 | 201 | 202 | 203 | 204 | 205 | 206 |
|---|---|---|---|---|---|---|---|---|---|
| Composition Type | Q | Q | Q | Q | Q | Q | Q | Q | Q |
| Composition weight, gm | 50 | 50 | 50 | 50 | 50 | 50 | 50 | 50 | 50 |
| Pressure, psig | 600 | 600 | 600 | 400 | 600 | 600 | 600 | 600 | 600 |
| Temperature, °C. | 251 | 250.5 | 260.7 | 265.6 | 270.4 | 275.8 | 280.5 | 255.8 | 245.5 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 4.35 | 4.44 | 4.56 | 3.97 | 4.31 | 4.29 | 4.42 | 3.99 | 4.38 |
| DETA/MEA mole ratio | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.129 | 0.034 | 0.081 | 0.130 | 0.184 | 0.319 | 0.432 | 0.086 | 0.044 |
| MEA | 31.011 | 33.961 | 32.995 | 30.431 | 29.013 | 27.475 | 26.166 | 30.793 | 34.503 |
| PIP | 0.136 | 0.085 | 0.172 | 0.302 | 0.423 | 0.645 | 0.863 | 0.155 | 0.069 |
| DETA | 59.305 | 59.998 | 58.455 | 58.206 | 56.825 | 54.579 | 51.202 | 55.790 | 59.775 |
| AEEA | 1.084 | 1.095 | 1.515 | 1.846 | 1.989 | 2.043 | 1.872 | 1.338 | 0.780 |
| AEP | 0.308 | 0.219 | 0.266 | 0.335 | 0.419 | 0.580 | 0.708 | 0.282 | 0.209 |
| HEP | 0.000 | 0.000 | 0.000 | 0.000 | 0.000 | 0.000 | 0.000 | 0.000 | 0.000 |
| TAEA | 0.432 | 0.292 | 0.389 | 0.566 | 0.673 | 0.798 | 0.785 | 0.390 | 0.223 |
| l-TETA | 2.508 | 1.580 | 1.972 | 2.095 | 3.532 | 4.375 | 4.754 | 2.170 | 1.109 |
| DAEP | 0.065 | 0.025 | 0.043 | 0.060 | 0.080 | 0.127 | 0.290 | 0.149 | 0.046 |
| PEEDA | 0.047 | 0.029 | 0.037 | 0.051 | 0.085 | 0.146 | 0.239 | 0.084 | 0.027 |
| DPE | 0.022 | 0.038 | 0.057 | 0.072 | 0.080 | 0.101 | 0.100 | 0.221 | 0.018 |
| AE-TAEA | 0.305 | 0.284 | 0.525 | 0.127 | 0.137 | 1.094 | 0.823 | 0.664 | 0.107 |
| l-TEPA | 0.579 | 0.428 | 0.478 | 1.062 | 1.431 | 1.985 | 2.525 | 1.037 | 0.075 |
| AE-DAEP | 0.063 | 0.194 | 0.053 | 0.066 | 0.116 | 0.232 | 0.666 | 0.600 | 0.000 |
| AE-PEEDA | 0.000 | 0.000 | 0.050 | 0.039 | 0.034 | 0.106 | 0.169 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.053 | 0.078 | 0.027 | 0.063 | 0.028 | 0.045 | 0.037 | 0.417 | 0.201 |
| BPEA | 0.035 | 0.000 | 0.000 | 0.021 | 0.040 | 0.046 | 0.045 | 0.037 | 0.000 |
| Others | 1.348 | 0.783 | 1.767 | 2.309 | 2.800 | 3.375 | 4.038 | 3.468 | 0.757 |
| MEA Conversion, % | 15.65 | 8.73 | 11.34 | 18.47 | 22.00 | 26.74 | 28.82 | 16.92 | 5.92 |
| DETA Conversion, % | 4.38 | 4.41 | 6.89 | 7.56 | 9.44 | 13.72 | 17.43 | 10.77 | 3.38 |
| Acyclic(N4), % | 95.58 | 95.25 | 94.45 | 94.94 | 94.46 | 93.24 | 89.79 | 84.87 | 93.55 |
| Acyclic(N5), % | 85.28 | 72.27 | 88.43 | 86.18 | 87.68 | 87.70 | 78.48 | 61.69 | 47.55 |
| Σ(N5)/Σ(N4), weight ratio | 0.33 | 0.50 | 0.45 | 0.37 | 0.40 | 0.63 | 0.69 | 0.91 | 0.26 |
| Acyclic(N4)/cyclic (<=N4), weight ratio | 5.06 | 4.70 | 4.08 | 4.22 | 3.85 | 3.23 | 2.51 | 2.86 | 3.60 |

TABLE XVIII

| Example No. | 207 | 208 | 209 | 210 | 211 | 212 | 213 | 214 | 215 | 216 | 217 |
|---|---|---|---|---|---|---|---|---|---|---|---|
| Composition Type | R | R | R | R | R | R | R | R | R | R | R |
| Composition weight, gm | 50 | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 | 600 |
| Temperature, °C. | 249.4 | 250.2 | 260.0 | 264.8 | 274.3 | 269.7 | 279.6 | 254.9 | 265.5 | 250.0 | 250.0 |
| Time on organics, hrs. | 3.5 | 22.5 | 27.0 | 46.5 | 50.5 | 70.5 | 74.5 | 94.5 | 98.5 | 118.0 | 142.0 |
| Duration of run, hrs. | 2 | 2 | 2 | 2 | 2 | 2 | 2 | 2 | 2 | 2 | 2 |
| MEA SV, gmol/hr/kgcat | 4.87 | 5.72 | 6.05 | 6.00 | 6.02 | 5.98 | 5.04 | 5.89 | 5.99 | 5.66 | 5.83 |
| DETA/MEA mole ratio | 0.99 | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 1.519 | 0.694 | 1.216 | 1.280 | 2.428 | 1.153 | 2.115 | 0.252 | 0.488 | 0.120 | 0.078 |
| MEA | 31.506 | 32.042 | 30.354 | 30.605 | 27.717 | 30.601 | 23.296 | 33.872 | 32.164 | 35.051 | 35.546 |
| PIP | 0.817 | 0.572 | 1.053 | 1.075 | 1.986 | 0.958 | 1.810 | 0.224 | 0.444 | 0.105 | 0.071 |
| DETA | 49.429 | 53.921 | 50.152 | 49.725 | 43.594 | 50.450 | 38.887 | 57.536 | 55.374 | 59.521 | 60.251 |
| AEEA | 0.896 | 0.966 | 1.015 | 0.991 | 0.957 | 1.013 | 0.855 | 0.774 | 1.009 | 0.339 | 0.338 |
| AEP | 0.642 | 0.422 | 0.770 | 0.803 | 1.591 | 0.760 | 1.481 | 0.293 | 0.430 | 0.243 | 0.206 |
| HEP | 0.000 | 0.000 | 0.000 | 0.000 | 0.000 | 0.000 | 0.000 | 0.000 | 0.000 | 0.000 | 0.000 |
| TAEA | 0.734 | 0.732 | 0.884 | 0.820 | 0.779 | 0.837 | 0.758 | 0.520 | 0.767 | 0.322 | 0.235 |
| l-TETA | 4.465 | 4.271 | 5.695 | 5.262 | 5.911 | 5.274 | 5.499 | 2.760 | 4.241 | 1.727 | 1.284 |
| DAEP | 0.173 | 0.090 | 0.194 | 0.193 | 0.476 | 0.176 | 0.452 | 0.039 | 0.095 | 0.000 | 0.000 |
| PEEDA | 0.153 | 0.064 | 0.187 | 0.199 | 0.589 | 0.178 | 0.544 | 0.025 | 0.099 | 0.000 | 0.000 |
| DPE | 0.059 | 0.026 | 0.052 | 0.062 | 0.131 | 0.056 | 0.168 | 0.000 | 0.044 | 0.000 | 0.000 |
| AE-TAEA | 0.538 | 0.468 | 0.781 | 0.769 | 0.931 | 0.682 | 0.987 | 0.185 | 0.411 | 0.000 | 0.000 |
| l-TEPA | 1.798 | 1.534 | 2.851 | 2.784 | 3.990 | 2.531 | 3.812 | 0.440 | 1.232 | 0.000 | 0.000 |
| AE-DAEP | 0.111 | 0.079 | 0.177 | 0.165 | 0.389 | 0.088 | 0.463 | 0.000 | 0.000 | 0.000 | 0.000 |
| AE-PEEDA | 0.165 | 0.051 | 0.105 | 0.092 | 0.193 | 0.074 | 0.275 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.105 | 0.000 | 0.000 | 0.000 | 0.000 |
| BPEA | 0.000 | 0.000 | 0.090 | 0.098 | 0.188 | 0.085 | 0.308 | 0.000 | 0.000 | 0.000 | 0.000 |
| Others | 2.487 | 1.092 | 2.264 | 2.409 | 4.492 | 2.276 | 5.439 | 0.924 | 1.213 | 0.418 | 0.337 |
| MEA Conversion, % | 12.79 | 12.53 | 18.53 | 17.36 | 25.28 | 17.17 | 30.93 | 7.75 | 13.08 | 4.17 | 3.21 |
| DETA Conversion, % | 18.89 | 12.74 | 20.21 | 20.40 | 30.33 | 19.05 | 31.65 | 7.11 | 11.29 | 3.53 | 2.74 |
| Acyclic(N4), % | 93.08 | 96.49 | 93.79 | 93.03 | 84.81 | 93.68 | 84.30 | 98.06 | 95.42 | 100.00 | 100.00 |
| Acyclic(N5), % | 89.40 | 93.87 | 90.65 | 90.87 | 86.46 | 92.82 | 80.64 | 100.00 | 100.00 | 0.00 | 0.00 |
| Σ(N5)/Σ(N4), weight ratio | 0.46 | 0.41 | 0.57 | 0.59 | 0.72 | 0.53 | 0.80 | 0.18 | 0.31 | 0.00 | 0.00 |

TABLE XVIII-continued

| Example No. | 207 | 208 | 209 | 210 | 211 | 212 | 213 | 214 | 215 | 216 | 217 |
|---|---|---|---|---|---|---|---|---|---|---|---|
| Acyclic(N4)/cyclic (<=N4), weight ratio | 2.81 | 4.25 | 2.91 | 2.60 | 1.40 | 2.86 | 1.46 | 5.63 | 4.49 | 5.88 | 5.47 |

TABLE XIX

| Example No. | 218 | 219 | 220 | 221 | 222 | 223 | 224 | 225 | 226 | 227 |
|---|---|---|---|---|---|---|---|---|---|---|
| Composition Type | S | S | S | S | S | S | S | S | S | S |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.4 | 260.0 | 264.8 | 274.3 | 269.7 | 279.6 | 250.0 | 265.0 | 250.0 | 250.0 |
| Time on organics, hrs. | 3.5 | 27.0 | 46.5 | 50.5 | 70.5 | 74.5 | 94.5 | 98.5 | 118.0 | 142.0 |
| Duration of run, hrs. | 2 | 2 | 2 | 2 | 2 | 2 | 2 | 2 | 2 | 2 |
| MEA SV, gmol/hr/kgcat | 5.19 | 6.09 | 7.07 | 6.15 | 6.06 | 5.36 | 5.94 | 6.02 | 5.71 | 6.05 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 2.846 | 2.162 | 2.521 | 3.371 | 2.410 | 3.708 | 0.958 | 1.667 | 0.727 | 0.656 |
| MEA | 28.451 | 28.405 | 27.689 | 22.373 | 26.870 | 19.491 | 30.997 | 27.854 | 33.177 | 33.332 |
| PIP | 0.292 | 0.311 | 0.356 | 0.675 | 0.375 | 0.711 | 0.117 | 0.226 | 0.073 | 0.061 |
| DETA | 47.215 | 49.052 | 48.027 | 42.085 | 47.503 | 38.192 | 54.844 | 50.639 | 55.737 | 56.938 |
| AEEA | 1.527 | 1.477 | 1.552 | 1.306 | 1.542 | 1.289 | 1.199 | 1.503 | 0.934 | 0.936 |
| AEP | 0.394 | 0.489 | 0.563 | 0.836 | 0.604 | 0.971 | 0.390 | 0.530 | 0.340 | 0.348 |
| HEP | 0.000 | 0.000 | 0.000 | 0.000 | 0.000 | 0.000 | 0.000 | 0.000 | 0.000 | 0.000 |
| TAEA | 0.805 | 0.950 | 0.969 | 1.115 | 1.032 | 1.206 | 0.726 | 1.030 | 0.478 | 0.461 |
| l-TETA | 6.223 | 6.861 | 7.071 | 8.458 | 7.313 | 8.977 | 4.883 | 6.759 | 3.252 | 3.068 |
| DAEP | 0.139 | 0.130 | 0.150 | 0.290 | 0.155 | 0.368 | 0.054 | 0.112 | 0.000 | 0.000 |
| PEEDA | 0.054 | 0.065 | 0.083 | 0.181 | 0.089 | 0.248 | 0.048 | 0.059 | 0.046 | 0.037 |
| DPE | 0.186 | 0.172 | 0.213 | 0.359 | 0.226 | 0.502 | 0.080 | 0.180 | 0.036 | 0.025 |
| AE-TAEA | 0.595 | 0.826 | 0.906 | 1.543 | 0.942 | 1.789 | 0.306 | 0.113 | 0.129 | 0.072 |
| l-TEPA | 1.190 | 1.632 | 1.751 | 3.174 | 1.795 | 3.752 | 0.447 | 1.274 | 0.082 | 0.419 |
| AE-DAEP | 0.075 | 0.104 | 0.098 | 0.253 | 0.091 | 0.309 | 0.000 | 0.036 | 0.000 | 0.000 |
| AE-PEEDA | 0.356 | 0.187 | 0.182 | 0.431 | 0.151 | 0.490 | 0.000 | 0.085 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.079 | 0.083 | 0.070 | 0.063 | 0.065 | 0.158 | 0.101 | 0.121 | 0.309 | 0.000 |
| BPEA | 0.000 | 0.062 | 0.081 | 0.053 | 0.103 | 0.135 | 0.034 | 0.144 | 0.000 | 0.000 |
| Others | 4.635 | 4.013 | 4.427 | 8.254 | 4.444 | 10.424 | 2.167 | 4.231 | 1.493 | 1.571 |
| MEA Conversion, % | 21.20 | 23.10 | 24.95 | 39.09 | 26.53 | 46.19 | 15.71 | 24.30 | 8.77 | 9.35 |
| DETA Conversion, % | 22.48 | 21.28 | 22.83 | 32.08 | 23.00 | 37.50 | 11.59 | 18.42 | 9.14 | 8.20 |
| Acyclic(N4), % | 94.87 | 95.49 | 94.72 | 92.01 | 94.64 | 90.09 | 96.84 | 95.68 | 97.81 | 98.24 |
| Acyclic(N5), % | 77.74 | 84.86 | 85.97 | 85.46 | 86.94 | 83.49 | 84.65 | 78.19 | 40.69 | 100.00 |
| Σ(N5)/Σ(N4), weight ratio | 0.31 | 0.35 | 0.36 | 0.53 | 0.35 | 0.58 | 0.15 | 0.21 | 0.13 | 0.13 |
| Acyclic(N4)/cyclic (<=N4), weight ratio | 6.58 | 6.67 | 5.87 | 4.08 | 5.74 | 3.63 | 8.11 | 7.02 | 7.50 | 7.46 |

TABLE XX

| Example No. | 228 | 229 | 230 | 231 | 232 | 233 | 234 | 235 | 236 | 237 | 238 |
|---|---|---|---|---|---|---|---|---|---|---|---|
| Composition Type | T | T | T | T | T | T | T | T | T | T | T |
| Composition weight, gm | 50 | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 | 600 |
| Temperature, °C. | 249.4 | 250.2 | 260.0 | 264.8 | 274.3 | 269.7 | 279.6 | 254.9 | 265.5 | 250.0 | 250.0 |
| Time on organics, hrs. | 3.5 | 22.5 | 27.0 | 46.5 | 50.5 | 70.5 | 74.5 | 94.5 | 98.5 | 118.0 | 142.0 |
| Duration of run, hrs. | 2 | 2 | 2 | 2 | 2 | 2 | 2 | 2 | 2 | 2 | 2 |
| MEA SV, gmol/hr/kgcat | 4.96 | 5.31 | 5.56 | 5.64 | 5.56 | 5.51 | 5.09 | 5.43 | 5.54 | 5.23 | 5.37 |
| DETA/MEA mole ratio | 0.99 | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 0.654 | 0.449 | 0.757 | 0.960 | 1.686 | 1.190 | 2.015 | 0.476 | 0.898 | 0.343 | 0.351 |
| MEA | 27.386 | 29.344 | 25.472 | 23.704 | 17.028 | 22.148 | 12.850 | 28.641 | 23.935 | 30.296 | 30.702 |
| PIP | 0.229 | 0.158 | 0.318 | 0.417 | 0.765 | 0.526 | 0.925 | 0.165 | 0.377 | 0.111 | 0.109 |
| DETA | 53.639 | 55.586 | 52.752 | 50.945 | 45.979 | 49.847 | 40.504 | 56.024 | 51.376 | 57.092 | 57.637 |
| AEEA | 2.419 | 2.339 | 2.764 | 2.728 | 2.360 | 2.672 | 1.772 | 2.377 | 2.731 | 2.066 | 2.049 |
| AEP | 0.319 | 0.268 | 0.391 | 0.468 | 0.851 | 0.568 | 1.059 | 0.297 | 0.452 | 0.262 | 0.268 |
| HEP | 0.000 | 0.000 | 0.000 | 0.000 | 0.000 | 0.000 | 0.000 | 0.000 | 0.000 | 0.000 | 0.000 |
| TAEA | 1.067 | 0.826 | 1.226 | 1.323 | 1.677 | 1.416 | 1.728 | 0.900 | 1.406 | 0.710 | 0.675 |
| l-TETA | 6.467 | 4.920 | 7.114 | 7.589 | 9.995 | 8.115 | 10.503 | 4.990 | 7.814 | 3.954 | 3.695 |
| DAEP | 0.088 | 0.062 | 0.117 | 0.137 | 0.317 | 0.176 | 0.437 | 0.057 | 0.137 | 0.044 | 0.052 |
| PEEDA | 0.054 | 0.044 | 0.081 | 0.083 | 0.227 | 0.154 | 0.396 | 0.040 | 0.081 | 0.029 | 0.052 |
| DPE | 0.045 | 0.029 | 0.068 | 0.096 | 0.188 | 0.128 | 0.297 | 0.045 | 0.106 | 0.037 | 0.032 |
| AE-TAEA | 0.685 | 0.395 | 1.040 | 1.239 | 2.283 | 1.495 | 2.774 | 0.419 | 1.182 | 0.238 | 0.195 |
| l-TEPA | 1.252 | 0.683 | 2.067 | 2.357 | 4.522 | 2.895 | 5.506 | 0.703 | 2.253 | 0.393 | 0.295 |
| AE-DAEP | 0.000 | 0.000 | 0.099 | 0.104 | 0.276 | 0.134 | 0.596 | 0.000 | 0.079 | 0.000 | 0.000 |
| AE-PEEDA | 0.031 | 0.000 | 0.000 | 0.034 | 0.087 | 0.038 | 0.220 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.089 | 0.000 | 0.165 | 0.000 | 0.000 | 0.525 | 0.202 |
| BPEA | 0.098 | 0.000 | 0.136 | 0.132 | 0.363 | 0.186 | 0.107 | 0.000 | 0.130 | 0.000 | 0.000 |

TABLE XX-continued

| Example No. | 228 | 229 | 230 | 231 | 232 | 233 | 234 | 235 | 236 | 237 | 238 |
|---|---|---|---|---|---|---|---|---|---|---|---|
| Others | 1.308 | 1.020 | 1.910 | 2.415 | 4.738 | 3.325 | 7.889 | 1.257 | 2.793 | 1.201 | 1.290 |
| MEA Conversion, % | 24.85 | 19.33 | 30.93 | 34.91 | 53.54 | 39.67 | 63.95 | 21.61 | 34.98 | 17.69 | 16.70 |
| DETA Conversion, % | 12.74 | 9.41 | 15.20 | 17.07 | 25.63 | 19.50 | 32.65 | 9.10 | 17.26 | 8.05 | 7.29 |
| Acyclic(N4), % | 97.56 | 97.67 | 96.88 | 96.55 | 94.09 | 95.39 | 91.54 | 97.62 | 96.58 | 97.64 | 96.94 |
| Acyclic(N5), % | 93.71 | 100.00 | 92.95 | 92.97 | 89.29 | 92.45 | 88.36 | 100.00 | 94.22 | 54.59 | 70.75 |
| $\Sigma(N5)/\Sigma(N4)$, weight ratio | 0.26 | 0.18 | 0.38 | 0.41 | 0.61 | 0.47 | 0.70 | 0.18 | 0.38 | 0.24 | 0.15 |
| Acyclic(N4)/cyclic ($<=$N4), weight ratio | 10.21 | 10.19 | 8.53 | 7.40 | 4.96 | 6.13 | 3.92 | 9.70 | 7.96 | 9.58 | 8.47 |

TABLE XXI

| | Example No. | | | | | | | | | |
|---|---|---|---|---|---|---|---|---|---|---|
| | 239 | 240 | 241 | 242 | 243 | 244 | 245 | 246 | 247 | 248 |
| Composition Type | U | U | U | U | U | U | U | U | U | U |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 250.7 | 260.9 | 265.9 | 275.6 | 270.7 | 280.7 | 255.9 | 266.0 | 250.0 | 250.0 |
| Time on organics, hrs. | 24 | 28 | 48 | 52 | 72 | 76 | 96 | 100 | 119 | 143 |
| Duration of run, hrs. | 2 | 2 | 2 | 2 | 2 | 2 | 2 | 2 | 2 | 2 |
| MEA SV, gmol/hr/kgcat | 5.63 | 5.74 | 3.32 | 5.65 | 5.42 | 5.49 | 5.53 | 5.57 | 5.89 | 5.93 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.903 | 1.402 | 1.768 | 2.544 | 1.835 | 3.073 | 0.888 | 1.294 | 0.515 | 0.506 |
| MEA | 25.752 | 20.894 | 16.605 | 12.576 | 17.830 | 10.281 | 26.167 | 20.923 | 27.453 | 29.003 |
| PIP | 0.219 | 0.362 | 0.507 | 0.711 | 0.498 | 0.901 | 0.187 | 0.353 | 0.106 | 0.103 |
| DETA | 50.036 | 46.155 | 42.553 | 38.126 | 43.798 | 37.053 | 51.456 | 47.042 | 54.880 | 54.395 |
| AEEA | 1.893 | 2.170 | 2.124 | 1.446 | 1.873 | 1.003 | 2.038 | 2.036 | 1.893 | 1.661 |
| AEP | 0.352 | 0.501 | 0.668 | 0.969 | 0.662 | 1.189 | 0.334 | 0.490 | 0.278 | 0.267 |
| HEP | 0.000 | 0.000 | 0.000 | 0.000 | 0.000 | 0.000 | 0.000 | 0.000 | 0.000 | 0.000 |
| TAEA | 1.345 | 1.686 | 1.782 | 1.715 | 1.776 | 1.699 | 1.361 | 1.719 | 1.214 | 1.039 |
| 1-TETA | 9.150 | 11.543 | 12.441 | 12.696 | 11.873 | 12.762 | 8.128 | 10.831 | 7.041 | 5.981 |
| DAEP | 0.123 | 0.212 | 0.297 | 0.536 | 0.298 | 0.703 | 0.088 | 0.187 | 0.057 | 0.051 |
| PEEDA | 0.063 | 0.115 | 0.173 | 0.315 | 0.175 | 0.078 | 0.051 | 0.100 | 0.035 | 0.035 |
| DPE | 0.076 | 0.135 | 0.211 | 0.313 | 0.079 | 0.133 | 0.082 | 0.072 | 0.048 | 0.060 |
| AE-TAEA | 1.447 | 2.123 | 2.635 | 3.323 | 2.723 | 3.556 | 1.164 | 2.237 | 0.691 | 0.565 |
| 1-TEPA | 2.439 | 3.738 | 4.737 | 6.407 | 4.814 | 6.968 | 1.786 | 3.880 | 0.956 | 0.711 |
| AE-DAEP | 0.033 | 0.115 | 0.343 | 0.446 | 0.192 | 0.758 | 0.000 | 0.081 | 0.000 | 0.000 |
| AE-PEEDA | 0.000 | 0.048 | 0.132 | 0.326 | 0.068 | 0.357 | 0.000 | 0.045 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.062 | 0.077 | 0.106 | 0.119 | 0.091 | 0.112 | 0.000 | 0.000 | 0.000 | 0.000 |
| BPEA | 0.198 | 0.376 | 0.163 | 0.712 | 0.593 | 0.257 | 0.112 | 0.102 | 0.000 | 0.000 |
| Others | 1.859 | 3.207 | 5.566 | 8.060 | 4.576 | 10.826 | 1.993 | 3.228 | 1.156 | 1.187 |
| MEA Conversion, % | 30.00 | 43.32 | 54.48 | 65.46 | 51.49 | 72.02 | 28.58 | 43.01 | 25.09 | 19.91 |
| DETA Conversion, % | 19.37 | 25.78 | 30.84 | 37.92 | 29.36 | 40.22 | 16.74 | 24.04 | 11.23 | 10.95 |
| Acyclic(N4), % | 97.54 | 96.61 | 95.41 | 92.51 | 96.10 | 94.03 | 97.71 | 97.19 | 98.32 | 97.94 |
| Acyclic(N5), % | 92.96 | 90.47 | 90.82 | 85.91 | 88.84 | 87.63 | 96.33 | 96.38 | 100.00 | 100.00 |
| $\Sigma(N5)/\Sigma(N4)$, weight ratio | 0.38 | 0.47 | 0.54 | 0.72 | 0.59 | 0.78 | 0.31 | 0.49 | 0.19 | 0.17 |
| Acyclic(N4)/cyclic ($<$ = N4), weight ratio | 12.56 | 9.96 | 7.65 | 5.06 | 7.95 | 4.80 | 12.76 | 10.41 | 15.69 | 13.56 |

TABLE XXII

| | Example No. | | | | | | | | | |
|---|---|---|---|---|---|---|---|---|---|---|
| | 249 | 250 | 251 | 252 | 253 | 254 | 255 | 256 | 257 | 258 |
| Composition Type | V | V | V | V | V | V | V | V | V | V |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 250.9 | 260.9 | 265.9 | 275.6 | 270.7 | 280.7 | 255.9 | 266.0 | 250.0 | 250.0 |
| Time on organics, hrs. | 24 | 28 | 48 | 52 | 72 | 76 | 96 | 100 | 119 | 143 |
| Duration of run, hrs. | 2 | 2 | 2 | 2 | 2 | 2 | 2 | 2 | 2 | 2 |
| MEA SV, gmol/hr/kgcat | 5.32 | 5.25 | 5.18 | 5.19 | 5.09 | 5.20 | 5.18 | 5.12 | 5.39 | 5.47 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.592 | 1.050 | 1.170 | 2.045 | 1.486 | 2.547 | 0.696 | 1.188 | 0.456 | 0.452 |
| MEA | 27.184 | 23.113 | 22.344 | 15.162 | 21.294 | 13.368 | 28.286 | 24.782 | 31.286 | 31.867 |
| PIP | 0.127 | 0.270 | 0.291 | 0.551 | 0.372 | 0.660 | 0.135 | 0.269 | 0.080 | 0.076 |
| DETA | 53.615 | 49.172 | 48.478 | 41.150 | 47.716 | 39.980 | 54.059 | 50.590 | 55.663 | 57.022 |
| AEEA | 2.106 | 2.326 | 2.191 | 1.866 | 2.144 | 1.559 | 1.968 | 2.123 | 1.530 | 1.495 |
| AEP | 0.280 | 0.388 | 0.415 | 0.715 | 0.489 | 0.840 | 0.283 | 0.381 | 0.235 | 0.239 |
| HEP | 0.000 | 0.000 | 0.000 | 0.000 | 0.000 | 0.000 | 0.000 | 0.000 | 0.000 | 0.000 |
| TAEA | 1.264 | 1.608 | 1.571 | 1.888 | 1.686 | 1.837 | 1.171 | 1.430 | 0.801 | 0.757 |
| 1-TETA | 7.794 | 10.144 | 9.823 | 12.185 | 10.176 | 11.968 | 6.606 | 8.234 | 4.501 | 4.245 |
| DAEP | 0.076 | 0.137 | 0.147 | 0.347 | 0.166 | 0.413 | 0.062 | 0.105 | 0.035 | 0.000 |

TABLE XXII-continued

| | Example No. | | | | | | | | | |
|---|---|---|---|---|---|---|---|---|---|---|
| | 249 | 250 | 251 | 252 | 253 | 254 | 255 | 256 | 257 | 258 |
| PEEDA | 0.034 | 0.074 | 0.089 | 0.211 | 0.099 | 0.086 | 0.039 | 0.063 | 0.029 | 0.000 |
| DPE | 0.045 | 0.094 | 0.134 | 0.118 | 0.156 | 0.130 | 0.066 | 0.108 | 0.000 | 0.000 |
| AE-TAEA | 0.814 | 0.589 | 1.649 | 2.952 | 1.965 | 3.233 | 0.758 | 1.349 | 0.372 | 0.000 |
| 1-TEPA | 1.274 | 2.726 | 2.848 | 5.423 | 3.349 | 5.930 | 1.123 | 2.132 | 0.504 | 0.000 |
| AE-DAEP | 0.000 | 0.000 | 0.086 | 0.479 | 0.108 | 0.545 | 0.000 | 0.031 | 0.000 | 0.000 |
| AE-PEEDA | 0.000 | 0.000 | 0.029 | 0.188 | 0.035 | 0.201 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.073 | 0.100 | 0.119 | 0.079 | 0.126 | 0.000 | 0.070 | 0.000 | 0.000 |
| BPEA | 0.000 | 0.199 | 0.189 | 0.565 | 0.277 | 0.243 | 0.000 | 0.169 | 0.000 | 0.000 |
| Others | 1.237 | 2.368 | 2.867 | 7.018 | 3.114 | 8.624 | 1.140 | 2.109 | 1.021 | 1.114 |
| MEA Conversion, % | 26.02 | 37.12 | 38.74 | 58.74 | 41.99 | 63.48 | 22.75 | 32.08 | 14.00 | 12.93 |
| DETA Conversion, % | 13.50 | 20.70 | 21.21 | 33.62 | 22.94 | 35.25 | 12.48 | 17.80 | 9.30 | 7.64 |
| Acyclic(N4), % | 98.30 | 97.45 | 96.84 | 95.40 | 96.55 | 95.63 | 97.87 | 97.21 | 98.79 | 100.00 |
| Acyclic(N5), % | 100.00 | 94.05 | 91.70 | 86.09 | 91.37 | 89.13 | 100.00 | 92.76 | 100.00 | 0.000 |
| Σ(N5)/Σ(N4), weight ratio | 0.22 | 0.38 | 0.41 | 0.65 | 0.47 | 0.71 | 0.23 | 0.37 | 0.16 | 0.000 |
| Acyclic(N4)/cyclic (<= N4), weight ratio | 16.04 | 12.16 | 10.56 | 7.23 | 9.23 | 6.47 | 13.23 | 10.42 | 13.92 | 15.87 |

TABLE XXIII

| | Example No. | | | | | | | | | |
|---|---|---|---|---|---|---|---|---|---|---|
| | 259 | 260 | 261 | 262 | 263 | 264 | 265 | 266 | 267 | 268 |
| Composition Type | W | W | W | W | W | W | W | W | W | W |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.8 | 249.5 | 259.9 | 264.3 | 274.1 | 270.2 | 279.2 | 254.5 | 264.3 | 251.7 |
| Time on organics, hrs. | 4 | 24 | 28 | 48 | 52 | 72 | 72 | 96 | 100 | 120 |
| Duration of run, hrs.. | 2 | 2 | 2 | 2 | 2 | 2 | 2 | 2 | 2 | 2 |
| MEA SV, gmol/hr/kgcat | 6.01 | 5.76 | 6.31 | 6.08 | 6.51 | 6.27 | 6.51 | 6.20 | 6.03 | 6.22 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.761 | 0.624 | 1.038 | 1.221 | 1.948 | 1.583 | 2.362 | 0.611 | 1.025 | 0.465 |
| MEA | 25.622 | 26.514 | 24.098 | 23.576 | 16.694 | 20.651 | 13.560 | 28.634 | 23.574 | 29.808 |
| PIP | 0.313 | 0.180 | 0.319 | 0.354 | 0.596 | 0.466 | 0.712 | 0.136 | 0.289 | 0.092 |
| DETA | 51.757 | 52.135 | 49.333 | 49.050 | 42.503 | 46.442 | 40.240 | 54.507 | 48.715 | 53.735 |
| AEEA | 2.271 | 2.049 | 2.327 | 2.321 | 1.938 | 2.152 | 1.499 | 1.953 | 2.175 | 1.635 |
| AEP | 0.469 | 0.304 | 0.391 | 0.428 | 0.713 | 0.549 | 0.914 | 0.271 | 0.386 | 0.235 |
| HEP | 0.000 | 0.000 | 0.000 | 0.000 | 0.000 | 0.000 | 0.000 | 0.000 | 0.000 | 0.000 |
| TAEA | 1.249 | 1.216 | 1.449 | 1.478 | 1.706 | 1.601 | 1.752 | 1.109 | 1.439 | 0.776 |
| 1-TETA | 8.948 | 8.159 | 9.767 | 9.512 | 11.779 | 10.430 | 12.550 | 6.599 | 9.395 | 4.640 |
| DAEP | 0.121 | 0.097 | 0.148 | 0.142 | 0.316 | 0.196 | 0.455 | 0.057 | 0.152 | 0.074 |
| PEEDA | 0.067 | 0.063 | 0.086 | 0.097 | 0.232 | 0.028 | 0.325 | 0.033 | 0.091 | 0.000 |
| DPE | 0.039 | 0.054 | 0.073 | 0.086 | 0.203 | 0.141 | 0.249 | 0.054 | 0.069 | 0.000 |
| AE-TAEA | 1.082 | 1.193 | 1.621 | 1.608 | 2.838 | 2.237 | 3.225 | 0.711 | 1.419 | 0.310 |
| 1-TEPA | 2.014 | 2.188 | 2.900 | 2.766 | 5.279 | 3.962 | 6.363 | 1.162 | 2.409 | 0.421 |
| AE-DAEP | 0.000 | 0.000 | 0.066 | 0.041 | 0.429 | 0.137 | 0.501 | 0.000 | 0.000 | 0.000 |
| AE-PEEDA | 0.000 | 0.000 | 0.000 | 0.000 | 0.162 | 0.052 | 0.290 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.083 | 0.071 | 0.078 | 0.546 | 0.099 | 0.570 | 0.264 | 0.111 | 0.000 |
| BPEA | 0.000 | 0.140 | 0.190 | 0.225 | 0.601 | 0.329 | 0.696 | 0.000 | 0.132 | 0.000 |
| Others | 1.401 | 1.373 | 1.963 | 2.198 | 5.197 | 3.367 | 6.347 | 1.172 | 1.892 | 0.943 |
| MEA Conversion, % | 30.38 | 28.05 | 34.69 | 35.69 | 54.79 | 43.71 | 63.20 | 22.55 | 34.28 | 15.16 |
| DETA Conversion, % | 16.63 | 16.13 | 20.74 | 20.69 | 31.77 | 24.95 | 35.27 | 12.60 | 19.49 | 9.33 |
| Acyclic(N4), % | 97.81 | 97.75 | 97.31 | 97.11 | 94.71 | 97.04 | 93.27 | 98.14 | 97.18 | 98.64 |
| Acyclic(N5), % | 100.00 | 93.80 | 93.22 | 92.68 | 82.34 | 90.92 | 82.32 | 87.61 | 93.99 | 100.00 |
| Σ(N5)/Σ(N4), weight ratio | 0.29 | 0.37 | 0.42 | 0.41 | 0.69 | 0.54 | 0.75 | 0.27 | 0.36 | 0.13 |
| Acyclic(N4)/cyclic (<= N4), weight ratio | 10.08 | 13.38 | 10.99 | 9.89 | 6.53 | 8.70 | 5.38 | 13.91 | 10.95 | 13.46 |

TABLE XXIV

| | Example No. | | | |
|---|---|---|---|---|
| | 269 | 270 | 271 | 272 |
| Composition Type | X | X | X | X |
| Composition weight, gm | 50 | 50 | 50 | 50 |
| Pressure, psig | 600 | 600 | 600 | 600 |
| Temperature, °C. | 249.8 | 264.3 | 274.1 | 270.2 |
| Time on organics, hrs. | 4 | 37 | 40 | 61 |
| Duration of run, hrs. | 2 | 2 | 2 | 2 |
| MEA SV, gmol/hr/kgcat | 5.86 | 5.73 | 5.94 | 5.40 |
| DETA/MEA mole ratio | 0.99 | 0.99 | 0.99 | 0.99 |
| NH3/MEA mole ratio | 5.98 | 5.98 | 5.98 | 5.98 |
| Crude product composition, wt. % | | | | |
| EDA | 1.024 | 1.195 | 2.071 | 1.604 |
| MEA | 26.663 | 25.244 | 19.405 | 22.346 |
| PIP | 0.296 | 0.293 | 0.530 | 0.392 |
| DETA | 50.089 | 49.881 | 43.746 | 46.459 |
| AEEA | 1.810 | 1.985 | 1.764 | 1.910 |
| AEP | 0.383 | 0.382 | 0.629 | 0.466 |
| HEP | 0.000 | 0.000 | 0.000 | 0.000 |
| TAEA | 1.335 | 1.526 | 1.657 | 1.567 |

TABLE XXIV-continued

| | Example No. | | | |
|---|---|---|---|---|
| | 269 | 270 | 271 | 272 |
| 1-TETA | 7.810 | 8.794 | 10.168 | 9.213 |
| DAEP | 0.119 | 0.111 | 0.244 | 0.145 |
| PEEDA | 0.083 | 0.063 | 0.147 | 0.090 |
| DPE | 0.049 | 0.091 | 0.211 | 0.141 |
| AE-TAEA | 1.264 | 1.525 | 2.605 | 1.943 |
| 1-TEPA | 2.012 | 2.274 | 4.356 | 3.093 |
| AE-DAEP | 0.000 | 0.000 | 0.377 | 0.094 |
| AE-PEEDA | 0.057 | 0.000 | 0.155 | 0.035 |
| iAE-PEEDA | 0.000 | 0.000 | 0.000 | 0.000 |
| AE-DPE | 0.076 | 0.077 | 0.546 | 0.097 |
| BPEA | 0.038 | 0.166 | 0.533 | 0.257 |
| Others | 1.245 | 2.056 | 5.068 | 3.030 |
| MEA Conversion, % | 25.98 | 31.20 | 47.33 | 37.71 |
| DETA Conversion, % | 17.56 | 19.41 | 29.62 | 23.22 |
| Acyclic(N4), % | 97.31 | 97.48 | 95.14 | 96.61 |
| Acyclic(N5), % | 95.00 | 93.96 | 81.20 | 91.22 |
| $\Sigma(N5)/\Sigma(N4)$, weight ratio | 0.36 | 0.38 | 0.68 | 0.49 |
| Acyclic(N4)/cyclic ($\leq$ N4), weight ratio | 9.81 | 10.94 | 6.70 | 8.72 |

TABLE XXV

| | Example No. | | | | | | | | | |
|---|---|---|---|---|---|---|---|---|---|---|
| | 273 | 274 | 275 | 276 | 277 | 278 | 279 | 280 | 281 | 282 |
| Composition Type | Y | Y | Y | Y | Y | Y | Y | Y | Y | Y |
| Composition weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.8 | 249.5 | 259.9 | 264.3 | 274.1 | 270.2 | 279.2 | 254.5 | 264.3 | 251.7 |
| Time on organics, hrs. | 4 | 24 | 28 | 48 | 52 | 72 | 72 | 96 | 100 | 120 |
| Duration of run, hrs. | 2 | 2 | 2 | 2 | 2 | 2 | 2 | 2 | 2 | 2 |
| MEA SV, gmol/hr/kgcat | 5.10 | 4.90 | 5.23 | 5.17 | 5.39 | 5.13 | 5.44 | 5.16 | 5.11 | 5.35 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.960 | 0.781 | 1.286 | 1.404 | 2.490 | 1.935 | 2.792 | 0.714 | 1.281 | 0.493 |
| MEA | 25.276 | 26.501 | 22.272 | 21.316 | 14.838 | 19.716 | 11.330 | 27.403 | 22.785 | 27.477 |
| PIP | 0.268 | 0.204 | 0.383 | 0.358 | 0.742 | 0.540 | 0.837 | 0.168 | 0.348 | 0.103 |
| DETA | 50.594 | 51.409 | 47.463 | 45.857 | 40.344 | 44.583 | 37.401 | 53.232 | 47.558 | 54.912 |
| AEEA | 2.227 | 2.171 | 2.322 | 2.246 | 1.783 | 2.068 | 1.362 | 2.040 | 2.125 | 1.779 |
| AEP | 0.365 | 0.314 | 0.469 | 0.481 | 0.878 | 0.612 | 1.085 | 0.294 | 0.441 | 0.273 |
| HEP | 0.000 | 0.000 | 0.000 | 0.000 | 0.000 | 0.000 | 0.000 | 0.000 | 0.000 | 0.000 |
| TAEA | 1.233 | 1.224 | 1.587 | 1.506 | 1.615 | 1.578 | 1.689 | 1.266 | 1.424 | 1.095 |
| 1-TETA | 9.272 | 8.238 | 10.975 | 10.156 | 11.821 | 10.601 | 12.728 | 7.741 | 9.232 | 6.746 |
| DAEP | 0.116 | 0.088 | 0.175 | 0.175 | 0.394 | 0.229 | 0.599 | 0.075 | 0.153 | 0.071 |
| PEEDA | 0.072 | 0.059 | 0.117 | 0.170 | 0.031 | 0.173 | 0.376 | 0.041 | 0.100 | 0.028 |
| DPE | 0.061 | 0.053 | 0.092 | 0.124 | 0.233 | 0.160 | 0.305 | 0.047 | 0.090 | 0.000 |
| AE-TAEA | 1.263 | 1.061 | 1.872 | 2.256 | 3.087 | 2.494 | 3.494 | 0.922 | 1.714 | 0.435 |
| 1-TEPA | 2.381 | 1.850 | 3.306 | 4.088 | 5.984 | 4.457 | 6.930 | 1.552 | 2.925 | 0.540 |
| AE-DAEP | 0.000 | 0.000 | 0.049 | 0.183 | 0.533 | 0.160 | 0.701 | 0.000 | 0.039 | 0.000 |
| AE-PEEDA | 0.000 | 0.000 | 0.000 | 0.202 | 0.312 | 0.063 | 0.374 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.076 | 0.000 | 0.077 | 0.648 | 0.544 | 0.112 | 0.581 | 0.000 | 0.112 | 0.000 |
| BPEA | 0.118 | 0.075 | 0.262 | 0.540 | 0.639 | 0.399 | 0.995 | 0.049 | 0.240 | 0.000 |
| Others | 1.481 | 1.265 | 2.484 | 2.761 | 6.684 | 3.550 | 7.622 | 1.247 | 2.245 | 1.490 |
| MEA Conversion, % | 31.15 | 27.16 | 39.53 | 42.00 | 59.71 | 45.84 | 69.02 | 25.71 | 36.32 | 24.24 |
| DETA Conversion, % | 18.31 | 16.23 | 23.60 | 26.03 | 35.07 | 27.41 | 39.37 | 14.45 | 21.21 | 10.25 |
| Acyclic(N4), % | 97.67 | 97.91 | 97.01 | 96.12 | 95.31 | 95.57 | 91.83 | 98.20 | 96.87 | 98.74 |
| Acyclic(N5), % | 94.93 | 97.48 | 93.01 | 80.11 | 81.72 | 90.42 | 79.71 | 98.02 | 92.20 | 100.00 |
| $\Sigma(N5)/\Sigma(N4)$, weight ratio | 0.35 | 0.30 | 0.43 | 0.65 | 0.78 | 0.60 | 0.83 | 0.27 | 0.45 | 0.12 |
| Acyclic(N4)/cyclic ($\leq$ N4), weight ratio | 11.88 | 13.13 | 10.13 | 8.90 | 5.89 | 7.09 | 4.49 | 14.33 | 9.39 | 16.44 |

TABLE XXVI

| | Example No. | | | | | | | |
|---|---|---|---|---|---|---|---|---|
| | 283 | 284 | 285 | 286 | 287 | 288 | 289 | 290 |
| Composition Type | Z | Z | Z | Z | Z | Z | Z | Z |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 5.47 | 5.89 | 6.03 | 6.26 | 6.37 | 6.13 | 6.30 | 5.74 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 0.720 | 0.471 | 0.905 | 1.039 | 1.480 | 1.147 | 1.920 | 2.426 |
| MEA | 22.009 | 25.260 | 20.953 | 20.030 | 12.865 | 18.327 | 11.062 | 10.395 |
| PIP | 0.236 | 0.148 | 0.320 | 0.360 | 0.596 | 0.411 | 0.716 | 0.888 |
| DETA | 49.471 | 53.904 | 50.021 | 50.155 | 43.606 | 48.889 | 42.722 | 43.690 |
| AEEA | 2.596 | 2.713 | 2.960 | 3.007 | 2.400 | 2.930 | 1.997 | 1.666 |
| AEP | 0.369 | 0.293 | 0.450 | 0.511 | 0.832 | 0.592 | 1.018 | 1.209 |
| HEP | 0.000 | 0.000 | 0.000 | 0.000 | 0.000 | 0.000 | 0.000 | 0.000 |
| TAEA | 1.431 | 1.225 | 1.593 | 1.658 | 1.845 | 1.669 | 1.892 | 1.745 |

TABLE XXVI-continued

| | Example No. | | | | | | | |
|---|---|---|---|---|---|---|---|---|
| | 283 | 284 | 285 | 286 | 287 | 288 | 289 | 290 |
| 1-TETA | 9.494 | 7.564 | 9.777 | 9.875 | 11.583 | 9.862 | 11.226 | 10.431 |
| DAEP | 0.148 | 0.096 | 0.184 | 0.198 | 0.402 | 0.207 | 0.439 | 0.480 |
| PEEDA | 0.122 | 0.090 | 0.106 | 0.123 | 0.320 | 0.113 | 0.034 | 0.294 |
| DPE | 0.066 | 0.055 | 0.069 | 0.086 | 0.155 | 0.046 | 0.133 | 0.167 |
| AE-TAEA | 1.452 | 0.810 | 1.783 | 1.741 | 3.025 | 1.768 | 3.034 | 2.823 |
| 1-TEPA | 2.655 | 1.402 | 3.149 | 3.152 | 5.660 | 3.141 | 5.502 | 5.191 |
| AE-DAEP | 0.000 | 0.000 | 0.000 | 0.048 | 0.304 | 0.056 | 0.503 | 0.535 |
| AE-PEEDA | 0.000 | 0.000 | 0.000 | 0.000 | 0.217 | 0.036 | 0.192 | 0.219 |
| iAE-PEEDA | 0.000 | 0.000 | 0.000 | 0.000 | 0.000 | 0.000 | 0.000 | 0.000 |
| AE-DPE | 0.085 | 0.000 | 0.106 | 0.088 | 0.532 | 0.055 | 0.161 | 0.144 |
| BPEA | 0.089 | 0.000 | 0.224 | 0.200 | 0.722 | 0.287 | 0.763 | 0.720 |
| Others | 1.049 | 1.041 | 2.233 | 2.823 | 5.516 | 3.315 | 7.516 | 7.487 |
| MEA Conversion, % | 37.93 | 30.47 | 42.95 | 45.73 | 64.84 | 49.30 | 69.45 | 71.21 |
| DETA Conversion, % | 17.29 | 12.04 | 19.27 | 19.45 | 29.37 | 19.83 | 30.06 | 28.28 |
| Acyclic(N4), % | 97.00 | 97.30 | 96.93 | 96.58 | 93.85 | 96.91 | 95.57 | 92.81 |
| Acyclic(N5), % | 95.91 | 100.00 | 93.70 | 93.55 | 83.01 | 91.86 | 84.03 | 83.18 |
| $\Sigma$(N5)/$\Sigma$(N4), weight ratio | 0.38 | 0.24 | 0.44 | 0.43 | 0.73 | 0.44 | 0.74 | 0.73 |
| Acyclic(N4)/cyclic ($<=$N4), weight ratio | 11.57 | 12.82 | 10.05 | 9.01 | 5.82 | 8.40 | 5.59 | 4.00 |

TABLE XXVII

| | Example No. | | | | | | | |
|---|---|---|---|---|---|---|---|---|
| | 291 | 292 | 293 | 294 | 295 | 296 | 297 | 298 |
| Composition Type | AA | AA | AA | AA | AA | AA | AA | AA |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 6.04 | 5.42 | 5.91 | 6.40 | 6.54 | 6.13 | 6.74 | 5.98 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.243 | 0.400 | 0.619 | 0.453 | 0.613 | 0.354 | 0.525 | 0.580 |
| MEA | 29.356 | 33.017 | 31.776 | 32.605 | 30.780 | 32.217 | 30.493 | 31.003 |
| PIP | 0.484 | 0.185 | 0.304 | 0.266 | 0.441 | 0.244 | 0.428 | 0.540 |
| DETA | 54.083 | 59.592 | 58.373 | 59.235 | 57.284 | 58.765 | 57.084 | 56.943 |
| AEEA | 1.249 | 0.742 | 1.272 | 1.184 | 1.363 | 1.159 | 1.500 | 1.300 |
| AEP | 0.395 | 0.262 | 0.352 | 0.330 | 0.422 | 0.301 | 0.428 | 0.482 |
| HEP | 0.000 | 0.000 | 0.000 | 0.000 | 0.000 | 0.000 | 0.000 | 0.000 |
| TAEA | 0.704 | 0.276 | 0.427 | 0.390 | 0.510 | 0.276 | 0.503 | 0.480 |
| 1-TETA | 3.680 | 1.530 | 2.245 | 1.887 | 2.609 | 1.462 | 2.595 | 2.425 |
| DAEP | 0.102 | 0.032 | 0.065 | 0.120 | 0.082 | 0.000 | 0.088 | 0.070 |
| PEEDA | 0.057 | 0.000 | 0.034 | 0.066 | 0.054 | 0.000 | 0.087 | 0.097 |
| DPE | 0.044 | 0.000 | 0.026 | 0.000 | 0.026 | 0.000 | 0.035 | 0.000 |
| AE-TAEA | 0.259 | 0.000 | 0.096 | 0.057 | 0.153 | 0.000 | 0.230 | 0.182 |
| 1-TEPA | 0.507 | 0.000 | 0.236 | 0.106 | 0.469 | 0.000 | 0.673 | 0.501 |
| AE-DAEP | 0.000 | 0.000 | 0.000 | 0.000 | 0.000 | 0.000 | 0.000 | 0.000 |
| AE-PEEDA | 0.133 | 0.000 | 0.000 | 0.000 | 0.000 | 0.000 | 0.067 | 0.000 |
| iAE-PEEDA | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.299 | 0.000 |
| BPEA | 0.000 | 0.000 | 0.000 | 0.000 | 0.000 | 0.000 | 0.000 | 0.000 |
| Others | 2.796 | 1.200 | 1.868 | 1.546 | 1.758 | 1.067 | 1.606 | 1.461 |
| MEA Conversion, % | 18.40 | 9.46 | 13.61 | 11.72 | 15.52 | 8.49 | 16.54 | 14.42 |
| DETA Conversion, % | 10.89 | 3.12 | 5.92 | 4.92 | 6.79 | 4.03 | 7.37 | 6.82 |
| Acyclic(N4), % | 95.54 | 98.24 | 95.49 | 92.41 | 95.03 | 100.00 | 93.59 | 94.56 |
| Acyclic(N5), % | 85.20 | 0.00 | 100.00 | 100.00 | 100.00 | 0.00 | 71.12 | 100.00 |
| $\Sigma$(N5)/$\Sigma$(N4), weight ratio | 0.19 | 0.00 | 0.11 | 0.06 | 0.18 | 0.00 | 0.38 | 0.22 |
| Acyclic(N4)/cyclic ($<=$N4), weight ratio | 4.04 | 3.76 | 3.41 | 2.90 | 3.03 | 3.18 | 2.89 | 2.44 |

TABLE XXVIII

| | Example No. | | | | | | | |
|---|---|---|---|---|---|---|---|---|
| | 299 | 300 | 301 | 302 | 303 | 304 | 305 | 306 |
| Composition Type | BB | BB | BB | BB | BB | BB | BB | BB |
| Composition weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 4.89 | 4.52 | 5.00 | 4.97 | 5.03 | 4.67 | 5.18 | 4.59 |
| DETA/MEA mole ratio | 0.99 | 0.99 | 0.99 | 0.99 | 0.99 | 0.99 | 0.99 | 0.99 |

TABLE XXVIII-continued

| | Example No. | | | | | | | |
|---|---|---|---|---|---|---|---|---|
| | 299 | 300 | 301 | 302 | 303 | 304 | 305 | 306 |
| NH₃/MEA mole ratio | 5.98 | 5.98 | 5.98 | 5.98 | 5.98 | 5.98 | 5.98 | 5.98 |
| Crude product composition, wt. % | | | | | | | | |
| EDA | 0.361 | 0.219 | 0.411 | 0.545 | 0.946 | 0.691 | 1.268 | 1.591 |
| MEA | 30.065 | 31.539 | 30.198 | 28.886 | 25.101 | 27.183 | 22.856 | 21.265 |
| PIP | 0.191 | 0.101 | 0.235 | 0.344 | 0.686 | 0.468 | 0.951 | 1.183 |
| DETA | 57.915 | 60.816 | 59.141 | 58.453 | 55.105 | 56.245 | 52.509 | 52.661 |
| AEEA | 1.844 | 1.669 | 2.173 | 2.351 | 2.319 | 2.307 | 2.115 | 1.849 |
| AEP | 0.299 | 0.245 | 0.312 | 0.391 | 0.627 | 0.461 | 0.842 | 1.032 |
| HEP | 0.000 | 0.000 | 0.000 | 0.000 | 0.000 | 0.000 | 0.000 | 0.000 |
| TAEA | 0.476 | 0.214 | 0.406 | 0.515 | 0.745 | 0.564 | 0.870 | 0.894 |
| 1-TETA | 2.817 | 1.483 | 2.555 | 3.157 | 4.703 | 3.517 | 5.428 | 5.629 |
| DAEP | 0.066 | 0.000 | 0.066 | 0.077 | 0.144 | 0.104 | 0.191 | 0.220 |
| PEEDA | 0.077 | 0.000 | 0.030 | 0.063 | 0.138 | 0.033 | 0.212 | 0.248 |
| DPE | 0.000 | 0.000 | 0.000 | 0.033 | 0.039 | 0.000 | 0.060 | 0.066 |
| AE-TAEA | 0.102 | 0.000 | 0.108 | 0.157 | 0.411 | 0.199 | 0.708 | 0.582 |
| 1-TEPA | 0.142 | 0.000 | 0.113 | 0.379 | 1.210 | 0.590 | 2.108 | 1.711 |
| AE-DAEP | 0.000 | 0.000 | 0.000 | 0.000 | 0.041 | 0.000 | 0.126 | 0.089 |
| AE-PEEDA | 0.000 | 0.000 | 0.000 | 0.000 | 0.037 | 0.000 | 0.098 | 0.085 |
| iAE-PEEDA | 0.000 | 0.000 | 0.000 | 0.000 | 0.000 | 0.000 | 0.000 | 0.000 |
| AE-DPE | 0.000 | 0.000 | 0.311 | 0.284 | 0.170 | 0.250 | 0.050 | 0.078 |
| BPEA | 0.000 | 0.000 | 0.000 | 0.000 | 0.000 | 0.000 | 0.101 | 0.096 |
| Others | 0.939 | 0.839 | 1.295 | 1.748 | 2.458 | 1.973 | 3.578 | 3.552 |
| MEA Conversion, % | 16.32 | 13.59 | 17.86 | 21.73 | 30.80 | 24.34 | 36.90 | 40.66 |
| DETA Conversion, % | 4.44 | 1.22 | 4.64 | 6.11 | 9.94 | 7.19 | 14.06 | 12.88 |
| Acyclic(N4), % | 95.83 | 100.00 | 96.82 | 95.45 | 94.40 | 96.74 | 93.13 | 92.40 |
| Acyclic(N5), % | 100.00 | 0.00 | 41.61 | 65.36 | 86.70 | 75.90 | 88.18 | 86.75 |
| Σ(N5)/Σ(N4), weight ratio | 0.07 | 0.00 | 0.17 | 0.21 | 0.32 | 0.24 | 0.47 | 0.37 |
| Acyclic(N4)/cyclic (< = N4), weight ratio | 5.19 | 4.88 | 4.59 | 4.03 | 3.32 | 3.82 | 2.78 | 2.37 |

Although the invention has been illustrated by certain of the preceding examples. it is not to be construed as being limited thereby; but rather, the invention encompasses the generic area as hereinbefore disclosed. Various modifications and embodiments can be made without departing from the spirit and scope thereof.

We claim:

1. A process for making amines which comprises (i) contacting one or more high surface area metal oxides with one or more amino compounds, glycol compounds or mixtures thereof at a temperature and pressure sufficient to provide a first vicinal di(hetero)alkylene organometalate compound, (ii) contacting said first vicinal di(hetero)alkylene organometalate compound with one or more amino compounds or mixtures thereof at a temperature and pressure sufficient to provide a second vicinal di(hetero)alkylene organometalate compound, and (iii) displacing the amine from said second vicinal di(hetero)alkylene organometalate compound.

2. A process for making amines which comprises (i) contacting one or more high surface area metal oxides with one or more alkanolamines, alkyleneamines, alkylene glycols or mixtures thereof at a temperature and pressure sufficient to provide a first vicinal di(hetero)alkylene organometalate compound, (ii) contacting said first vicinal di(hetero)alkylene organometalate compound with one or more alkanolamines, alkyleneamines or mixtures thereof at a temperature and pressure sufficient to provide a second vicinal di(hetero)alkylene organometalate compound, and (iii) displacing the amine from said second vicinal di(hetero)alkylene organometalate compound.

3. The process of claim 1 wherein the one or more high surface area metal oxides comprise one or more Group IIIB metal oxides. Group VB metal oxides, Group VIB metal oxides, Group VIIB metal oxides, Group VIII metal oxides, Group IIIA metal oxides, Group IV metal oxides, Group VA metal oxides, Group VIA metal oxides, Group IVB metal oxides or mixtures thereof.

4. The process of claim 3 wherein the one or more high surface area metal oxides comprise one or more oxides of scandium, yttrium, lanthanum, cerium, gadolinium, lutetium, ytterbium, iron, titanium, zirconium, hafnium, boron, aluminum, gallium, indium. silicon, germanium, tin, lead, arsenic, antimony, bismuth or mixtures thereof.

5. The process of claim 3 wherein the one or more high surface area metal oxides comprise a Group IVB metal oxide, a Group IVA metal oxide, a Group VIB metal oxide or mixtures thereof.

6. The process of claim 5 wherein the Group IVB metal oxide comprises a high surface area titanium oxide or zirconium oxide and the Group IVA metal oxide comprises high surface area silica.

7. The process of claim 5 wherein the Group VIB metal oxide comprises a high surface area tungsten oxide.

8. The process of claim 1 wherein the one or more metal oxides have a surface area greater than about 25 m²/gm.

9. The process of claim 6 wherein the titanium oxide comprises titanium dioxide and the zirconium oxide comprises zirconium dioxide.

10. The process of claim 5 wherein the one or more metal oxides comprise a mixture of titanium oxide, tungsten oxide and silica.

11. The process of claim 6 wherein the Group IVB metal oxide has a surface area greater 12. The process of claim 7 wherein the Group VIB metal oxide has a surface area greater than about 25 m²/gm.

13. The process of claim 1 wherein the one or high surface area more metal oxides are associated with a support material.

14. The process of claim 13 wherein the support comprises an alumina material or an alumina-silica material.

15. The process of claim 13 wherein the support comprises a silica material or a silica-alumina material.

16. The process of claim 13 wherein the support comprises from about 2 to about 60 percent by weight of the one or more high surface area metal oxides.

17. The process of claim 1 wherein the one or more high surface area metal oxides contain a performance moderator that enhances product selectivity of the process.

18. The process of claim 17 wherein the performance moderator comprises one or more metal oxides.

19. The process of claim 18 wherein the performance moderator comprises one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, Group IVB metal oxides or mixtures thereof.

20. The process of claim 19 wherein the performance moderator comprises one or more oxides of scandium, yttrium, lanthanum, cerium, gadolinium, lutetium, ytterbium, niobium, tantalum, chromium, molybdenum, tungsten, titanium, zirconium, hafnium, iron, cobalt, nickel, zinc, cadmium, boron, aluminum, gallium, indium, silicon, germanium, tin, lead, arsenic, antimony and bismuth 21. The process of claim 17 wherein the performance moderator comprises one or more metallic phosphates having a cyclic structure or an acyclic structure, metallic polyphosphates having a condensed structure, metallic metaphosphimates, metallic phosphoramidates, metallic amidophosphates, metallic imidophosphates or mixtures thereof.

22. The process of claim 21 wherein the performance moderator comprises a metallic orthophosphate, a metallic metaphosphate, a metallic pyrophosphate, a metallic polyphosphate, a metallic ultraphosphate, a metallic metaphosphimate, a metallic phosporamidate, a metallic amidophosphate, a metallic imidophosphate or mixtures thereof.

23. The process of claim 17 wherein the performance moderator comprises a mineral acid or a compound derived from a mineral acid.

24. The process of claim 23 wherein the performance moderator comprises phosphoric acid or a salt of phosphoric acid.

25. The process of claim 23 wherein the performance moderator comprises hydrogen fluoride, hydrofluoric acid or a fluoride salt.

26. The process of claim 23 wherein the performance moderator comprises sulfuric acid or a salt of sulfuric acid.

27. The process of claim 1 wherein the one or more high surface area metal oxides are associated with an oxyacid having a divalent or polyvalent anion or a divalent or polyvalent metal salt of an oxyacid or mixtures thereof.

28. The process of claim 27 wherein the oxyacid having a divalent or polyvalent anion or a divalent or polyvalent metal salt of an oxyacid comprise phosphoric acid, sulfuric acid, tungstic acid, molybdic acid, telluric acid, selenic acid, tungstophophoric acid, silicotungstic acid, ammonium metatungstate, sodium tetraborate or mixtures thereof.

29. The process of claim 1 wherein the one or more metal oxides comprise a mixed oxide of a Group IVB metal oxide and one or more other metal oxides.

30. The process of claim 29 wherein the other metal oxide comprises one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, other Group IVB metal oxides or mixtures thereof.

31. The process of claim 29 wherein the metal oxide comprises one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

32. The process of claim 1 wherein the one or more high surface area metal oxides comprise from about 25 weight percent to about 99 weight percent of the weight of the vicinal di(hetero)alkylene organometalate compound 33. The process of claim 1 wherein the amino compound comprises an alkyleneamine.

34. The process of claim 1 wherein the amino compound comprises ammonia in association with an alcohol.

35. The process of claim 34 wherein the alcohol comprises an alkanolamine

36. The process of claim 35 wherein the alkanolamine comprises aminoethylethanolamine.

37. The process of claim 1 wherein the amino compound comprises a mixture of monoethanolamine and ethylenediamine.

38. The process of claim 1 wherein the amino compound comprises a mixture of monoethanolamine and diethylenetriamine.

39. The process of claim 1 wherein the amino compound comprises a mixture of monoethanolamine, ethylenediamine and ammonia 40. The process of claim 1 wherein the amino compound comprises a mixture of monoethanolamine, diethylenetriamine and ammonia.

41. The process of claim 1 wherein the amino compound comprises a mixture of aminoethylethanolamine and ethylenediamine.

42. The process of claim 1 wherein the amino compound comprises a mixture of aminoethylethanolamine and diethylenetriamine.

43. The process of claim 1 wherein the amino compound comprises a mixture of aminoethylethanolamine, ethylenediamine and ammonia.

44. The process of claim 1 wherein the amino compound comprises a mixture of aminoethylethanolamine, diethylenetriamine and ammonia.

45. The process of claim 1 wherein the glycol compound comprises an alkylene glycol.

46. The process of claim 45 wherein the alkylene glycol comprises ethylene glycol, propylene glycol or 1,3-propane diol.

47. The process of claim 1 wherein the amines product has a TETA+TAEA to PIP+AEP+PEEDA+DAEP+DPE weight ratio of greater than about 0.5 and a TETA to TAEA weight ratio of greater than about 6.0.

48. The process of claim 1 in which the amines product comprises, based on 100 percent of the weight of the product and exclusive of any water and/or ammonia present, greater than about 3.0 weight percent of the combination of TETA and TEPA,
b) greater than about 0.1 weight percent of TEPA.
c) greater than about 3.0 weight percent of TETA,
d) less than about 90.0 weight percent of DETA and/or EDA,
e) less than about 90.0 weight percent of MEA and/or AEEA,
f) less than about 12.5 weight percent of the combination of PIP and AEP,
g) less than about 15.0 weight percent of other polyalkylene polyamines,
h) a TETA+TAEA to PIP+AEP+PEEDA+DAEP+DPE weight ratio of greater than about 0.5,
i) a TEPA+AETAEA to PIP+AEP+PEEDA+DAEP+DPE+AEPEEDA+iAEPEEDA+AEDAEP+AEDPE+BPEA weight ratio of greater than about 0.5,
j) a TETA to TAEA weight ratio of greater than about 6.0, and
k) a TEPA to AETAEA weight ratio of greater than about 1.0.

49. A process for making polyalkylene polyamines which comprises (i) contacting one or more high surface area metal oxides with one or more alkyleneamines at a temperature and pressure sufficient to provide a first vicinal di(hetero)alkylene organometalate compound, (ii) contacting said first vicinal di(hetero)alkylene organometalate compound with one or more alkanolamines at a temperature and pressure sufficient to provide a second vicinal di(hetero)alkylene organometalate compound, and (iii) displacing the polyalkylene polyamine from said second vicinal di(hetero)alkylene organometalate compound.

50. A process for making polyalkylene polyamines which comprises (i) contacting one or more high surface area metal oxides with one or more alkanolamines at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the polyalkylene polyamine from said second vicinal di(hetero)alkylene organometalate compound.

51. A process for making polyalkylene polyamines which comprises (i) contacting one or more high surface area metal oxides with one or more alkyleneamines at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the polyalkylene polyamine from said second vicinal di(hetero)alkylene organometalate compound.

52. A process for making alkanolamines which comprises (i) contacting one or more metal oxides with one or more alkanolamines at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the alkanolamine from said second vicinal di(hetero)alkylene organometalate compound.

53. A process for making alkanolamines which comprises (i) contacting one or more metal oxides with one or more alkyleneamines at a temperature and pressure sufficient to provide a first vicinal di(hetero)alkylene organometalate compound, (ii) contacting said first vicinal di(hetero)alkylene organometalate compound with one or more alkanolamines at a temperature and pressure sufficient to provide a second vicinal di(hetero)alkylene organometalate compound, and (iii) displacing the alkanolamine from said second vicinal di(hetero)alkylene organometalate compound.

54. A process for making alkanolamines which comprises (i) contacting one or more metal oxides with one or more alkanolamines at a temperature and pressure sufficient to provide a first vicinal di(hetero)alkylene organometalate compound, (ii) contacting said first vicinal di(hetero)alkylene organometalate compound with one or more alkanolamines at a temperature and pressure sufficient to provide a second vicinal di(hetero)alkylene organometalate compound, and (iii) displacing the alkanolamine from said second vicinal di(hetero)alkylene organometalate compound.

55. A process for making alkanolamines which comprises (i) contacting one or more metal oxides with one or more alkylene glycols at a temperature and pressure sufficient to provide a first vicinal di(hetero)alkylene organometalate compound, (ii) contacting said first vicinal di(hetero)alkylene organometalate compound with one or more alkanolamines at a temperature and pressure sufficient to provide a second vicinal di(hetero)alkylene organometalate compound, and (iii) displacing the alkanolamine from said second vicinal di(hetero)alkylene organometalate compound.

56. A process for making alkanolamines which comprises (i) contacting one or more metal oxides with one or more alkylene glycols at a temperature and pressure sufficient to provide a first vicinal di(hetero)alylene organometalate compound, (ii) contacting said first vicinal di(hetero)alkyulene organometalate compound with one or more alkyleneamines at a temperature and pressure sufficient to provide a second vicinal di(hetero)alkylene organometalate compound, and (iii) displacing the alkanolamine from said second vicinal di(hetero)alkylene organometalate compound.

57. A process for making alkyleneamines which comprises (i) contacting one or more high surface area metal oxides with one or more alkylene glycols at a temperature and pressure sufficient to provide a first vicinal di(hetero)alkylene organometalate compound, (ii) contacting said first vicinal di(hetero)alkylene organometalate compound with one or more alkyleneamines at a temperature and pressure sufficient to provide a second vicinal di(hetero)alkylene organometalate compound, and (iii) displacing the alkyleneamine from said second vicinal di(hetero)alkylene organometalate compound.

58. The process of claim 1 wherein the amino compound comprises ethylenediamine in association with ethylene glycol or diethylenetriamine in association with ethylene glycol.

59. The process of claim 1 wherein the amino compound comprises a mixture of diethanolamine and ethylenediamine or a mixture of diethanolamine and diethylenetriamine.

60. The process of claim 1 wherein the amino compound comprises a mixture of dihydroxyethylethylenediamine and ethylenediamine or a mixture of dihydroxyethylethylenediamine and diethylenetriamine.

61. The process of claim 1 wherein the amino compound comprises a mixture of hydroxyethyldiethylenetriamine and ethylenediamine or a mixture of hydroxyethyldiethylenetriamine and diethylenetriamine.

62. The process of claim 1 wherein the amino compound comprises a mixture of hydroxyethyltriethylenetetramine and ethylenediamine or a mixture of hydroxyethyltriethylenetetramine and diethylenetriamine.

63. The process of claim 1 which is effected in the liquid phase, vapor phase, supercritical liquid phase or mixtures thereof.

64. The process of claim 1 wherein the first vicinal di(hetero)alkylene organometalate compound comprises a compound having the formula selected from:

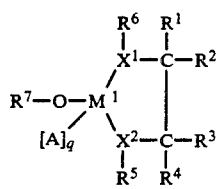

and

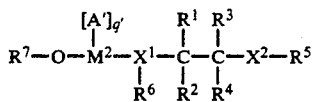

wherein:
A is independently an oxygen-containing substituent which fills the remaining valencies (g) of $M^1$;
g is independently a value of from 0 to about 4;
$M^1$ is independently a polyvalent metal having a functional positive oxidation state of w wherein the absolute value of w equals the absolute value of (g+2) or (g+3);
A' is independently an oxygen-containing substituent which fills the remaining valencies (g') of $M^2$;
g' is independently a value of from 0 to about 5;
$M^2$ is independently a polyvalent metal having a functional positive oxidation state of w' wherein the absolute value of w' equals the absolute value of (g'+2);
$X^1$ and $X^2$ are the same or different and are oxygen or nitrogen;
$R^1$, $R^2$, $R^3$ and $R^4$ are the same or different and are hydrogen or a substituted or unsubstituted hydrocarbyl substituent having from 1 to about 20 carbon atoms;
$R^5$ and $R^6$ are the same or different and are hydrogen, a substituted or unsubstituted hydrocarbyl substituent having from 1 to about 20 carbon atoms or a heteroatom-containing alkylene substituent; and
$R^7$ is independently hydrogen, a monovalent metal, a polyvalent metal-containing substituent, a heteroatom-containing alkylene substituent or a vicinal di(hetero)alkylene organometalate substituent having the formula selected from:

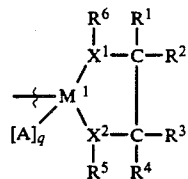

and

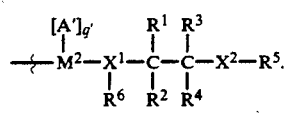

65. The process of claim 1 wherein the second vicinal di(hetero)alkylene organometalate compound comprises a compound comprises a compound having the formula selected from:

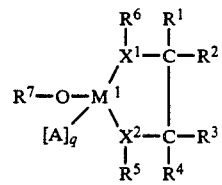

and

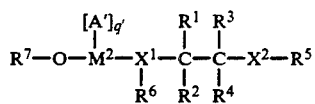

wherein:
A is independently an oxygen-containing substituent which fills the remaining valencies (g) or $M^1$;
g is independently a value of from 0 to about 4;
$M^1$ is independently a polyvalent metal having a functional positive oxidation state of w wherein the absolute value of w equals the absolute value of (g+2) or (g+3);
A' is independently an oxygen-containing substituent which fills the remaining valencies (g') of $M^2$;
g' is independently a value of from 0 to about 5;
$M^2$ is independently a polyvalent metal having a functional positive oxidation state of w' wherein the absolute value of w' equals the absolute value of (g'+2);
$X^1$ and $X^2$ are the same or different and are oxygen or nitrogen;
$R^1$, $R^2$, $R^3$ and $R^4$ are the same or different and are hydrogen or a substituted or unsubstituted hydrocarbyl substituent having from 1 to about 20 carbon atoms;
$R^5$ and $R^6$ are the same or different and are hydrogen, a substituted or unsubstituted hydrocarbyl substituent having from 1 to about 20 carbon atoms or a heteroatom-containing alkylene substituent; and
$R^7$ is independently hydrogen, a monovalent metal, a polyvalent metal-containing substituent, a heteroatom-containing alkylene substituent or a vicinal di(hetero)alkylene organometalate substituent having the formula selected from:

81
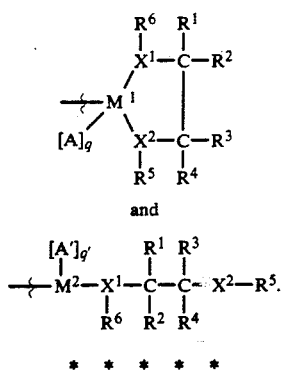
and
82
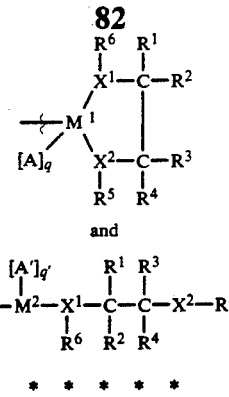
and
* * * * *

UNITED STATES PATENT AND TRADEMARK OFFICE
CERTIFICATE OF CORRECTION

PATENT NO. : 5,101,074

DATED : Mar. 31, 1992

INVENTOR(S) : Stephen W. King, et al.

It is certified that error appears in the above-identified patent and that said Letters Patent is hereby corrected as shown below:

On the Title page, item [54], "DI(HETRO)" should read --DI(HETERO)--.

Col. 8, line 31, for "(g+2) or (g+3)" read --(q+2) or (q+3)--.

Col. 8, line 64, for "(g')" read --(q')--.

Col. 8, line 67, for "(g'+2)" read --(q'+2)--.

Col. 9, lines 12, 13, for "(g')" read --(q')--.

Col. 9, line 16, for "(g'+2)" read --(q'+2)--.

Col. 9, line 47, for "(g) of $M^1$, g" read --(q) of $M^1$, q--.

Col. 9, lines 50-51, for "(g+2) or (g+3)" read --(q+2) or (q+3)--.

Col. 10, line 67, after "AEP+" read --PEEDA + DAEP+ --.

Col. 11, line 9, for "1 0" read -- 1.0 --.

Col. 12, line 13, for "(g)" read --(q)--.

Col. 12, line 14, for "g" read --q--.

Col. 12, line 52, for "(g') of $M^2$, g'" read --(q') of $M^2$, q'--.

Col. 12, line 67, for "(g')" read --(q')--.

Col. 12, line 68, for "g'" read --q'--.

Col. 13, line 3, for "(g'+2)" read --(q'+2)--.

Col. 13, line 35, for "(g) of $M^1$, g" read --(q) of $M^1$, q--.

UNITED STATES PATENT AND TRADEMARK OFFICE
CERTIFICATE OF CORRECTION

PATENT NO. : 5,101,074
DATED : Mar. 31, 1992
INVENTOR(S) : Stephen W. King, et al.

It is certified that error appears in the above-identified patent and that said Letters Patent is hereby corrected as shown below:

Col. 13, lines 38-39, for "(g+2) or (g+3)" read --(q+2) or (q+3)--.

Col. 13, line 43, for "(g)" read --(q)--.

Col. 14, line 24, for "(g')" read --(q')--.

Col. 15, line 13, for "(g+2) or (g+3)" read --(q+2) or (q+3)--.

Col. 15, line 14, for "(g+2)" read --(q+2)--.

Col. 15, line 15, for "(g+3)" read --(q+3)--.

Col. 15, line 19, for 'w' read --w'--.

Col. 15, line 20, for "(g+2)" read --(q+2)--.

Col. 20, line 46, delete "7".

Col. 20, line 46, start a new line beginning with " b) ..."

Col. 20, line 55, before "less" read --(g)--.

Col. 37, line 8, for "(1 71)" read --(1.71)--.

Col. 79, line 40, for "(g)" read --q--.

Col. 79, line 45, for "(g+2) or (g+3)" read --(q+2) or (q+3)--.

Col. 79, line 47, 48, for "(g') of $M^2$ ; g'" read --(q') of $M^2$ ; q'--.

Col. 79, line 52, for "(g'+2)" read --(q'+2)--.

Col. 80, line 39, for "(g)" read --q--.

UNITED STATES PATENT AND TRADEMARK OFFICE
CERTIFICATE OF CORRECTION

PATENT NO. : 5,101,074

DATED : Mar. 31, 1992

INVENTOR(S) : Stephen W. King et al.

It is certified that error appears in the above-identified patent and that said Letters Patent is hereby corrected as shown below:

Col. 80, line 45, for "(g+2) or (g+3)" read --(q+2) or (q+3)--.

Col. 80, line 47, 48, for "(g') of $M^2$ ; g'" read --(q') of $M^2$ ; q'--.

COL. 80. line 52, "g'+2" should read --(q'+2)--.

Signed and Sealed this

Twentieth Day of July, 1993

Attest:

MICHAEL K. KIRK

*Attesting Officer*        *Acting Commissioner of Patents and Trademarks*